US012275971B2

(12) United States Patent
Danquah et al.

(10) Patent No.: US 12,275,971 B2
(45) Date of Patent: *Apr. 15, 2025

(54) BIOLOGICAL DEGRADATION OF LOW-RANK COALS

(71) Applicant: Tenfold Technologies, LLC, Pilot Point, TX (US)

(72) Inventors: Michael K. Danquah, Humble, TX (US); Robert D. Chisholm, McKinney, TX (US); Allana K. Welsh, Danton, TX (US); Leslie M. Perry, Fort Worth, TX (US); Maud A. W. Hinchee, Little Elm, TX (US); Smrithi Rajagopal, Frisco, TX (US); Josh J. Redublo, Corpus Christi, TX (US)

(73) Assignee: TENFOLD TECHNOLOGIES, LLC, Pilot Point, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/498,656

(22) Filed: Oct. 31, 2023

(65) Prior Publication Data

US 2024/0060106 A1    Feb. 22, 2024

Related U.S. Application Data

(63) Continuation of application No. 17/298,786, filed as application No. PCT/US2019/064039 on Dec. 2, 2019.
(Continued)

(51) Int. Cl.
C05F 17/20 (2020.01)
C05F 11/02 (2006.01)
(Continued)

(52) U.S. Cl.
CPC .............. *C12P 17/188* (2013.01); *C05F 11/02* (2013.01); *C05F 17/20* (2020.01); *C05F 17/957* (2020.01);
(Continued)

(58) Field of Classification Search
CPC ........... C12P 17/188; C12P 7/50; C12P 39/00; C05F 11/02; C05F 17/20; C05F 17/957; C05G 5/23; A01C 21/00
See application file for complete search history.

(56) References Cited

U.S. PATENT DOCUMENTS 1,606,015 A    11/1926  Blackwell
3,398,186 A     8/1968  Schwartz
(Continued)

FOREIGN PATENT DOCUMENTS

AU    2010297937 A1    5/2012
EP       1797190 A1    6/2007
(Continued)

OTHER PUBLICATIONS

Xiao, Chunqiao, et al. "Rock phosphate solubilization by four yeast strains." Annals of Microbiology 63.1 (2013): 173-178. (Year: 2013).*
(Continued)

*Primary Examiner* — Jennifer A Smith
(74) *Attorney, Agent, or Firm* — WILSON SONSINI GOODRICH & ROSATI

(57) ABSTRACT

Methods and processes for producing aerobic digestion products, such as organic acids, from a low-rank coal substrate are provided. Also provided are multistage bioreactor systems for carrying out the described methods and processes. In another aspect, product compositions comprising organic acids produced by the described methods and processes are provided, as well as methods for their use,
(Continued)

including for the improvement of soil quality and/or plant growth.

26 Claims, 22 Drawing Sheets

Related U.S. Application Data

(60) Provisional application No. 62/773,541, filed on Nov. 30, 2018.

(51) Int. Cl.
| | |
|---|---|
| C05F 17/957 | (2020.01) |
| C05G 5/23 | (2020.01) |
| C12P 7/50 | (2006.01) |
| C12P 17/18 | (2006.01) |
| C12P 39/00 | (2006.01) |
| A01C 21/00 | (2006.01) |

(52) U.S. Cl.
CPC ............ *C05G 5/23* (2020.02); *C12P 7/50* (2013.01); *C12P 39/00* (2013.01); *A01C 21/00* (2013.01)

(56) References Cited

U.S. PATENT DOCUMENTS

| | | | |
|---|---|---|---|
| 3,674,649 A | 7/1972 | Formisano et al. | |
| 4,698,090 A | 10/1987 | Marihart | |
| 4,846,964 A * | 7/1989 | Scott | C10G 1/00 210/627 |
| 5,670,345 A | 9/1997 | Srivastava et al. | |
| 5,854,032 A | 12/1998 | Srivastava et al. | |
| 5,906,960 A | 5/1999 | Sanjay et al. | |
| 6,143,692 A | 11/2000 | Sanjay et al. | |
| 7,771,504 B1 | 8/2010 | Samani | |
| 8,614,165 B2 | 12/2013 | Goodwin | |
| 9,011,577 B2 | 4/2015 | Walia et al. | |
| 9,485,991 B2 | 11/2016 | Hanson et al. | |
| 10,035,736 B2 | 7/2018 | Goodwin | |
| 10,730,807 B2 | 8/2020 | Uchrin | |
| 2006/0070938 A1 * | 4/2006 | McWhirter | C02F 11/02 210/202 |
| 2008/0216534 A1 * | 9/2008 | Karr | C05F 11/02 71/9 |
| 2016/0023960 A1 | 1/2016 | Goodwin | |
| 2016/0297722 A1 | 10/2016 | Littmann | |
| 2017/0112127 A1 | 4/2017 | Hanson et al. | |
| 2022/0033868 A1 | 2/2022 | Danquah et al. | |

FOREIGN PATENT DOCUMENTS

| | | |
|---|---|---|
| IL | 85808 A | 6/1991 |
| WO | WO-2006000073 A1 | 1/2006 |
| WO | WO-2011038389 A2 | 3/2011 |
| WO | WO-2013056084 A2 | 4/2013 |
| WO | WO-2020113226 A1 | 6/2020 |

OTHER PUBLICATIONS

Pokorný, Richard, et al. "Characterization of microorganisms isolated from lignite excavated from the Záhorie coal mine ( southwestern Slovakia)." Research in microbiology 156.9 (2005): 932-943. (Year: 2005).*

Kertesz, M. A., and A. Kawasaki. "Hydrocarbon-degrading sphingomonads: Sphingomonas, sphingobium, novosphingobium, and sphingopyxis." Handbook of hydrocarbon and lipid microbiology. 2010. (Year: 2010).*

Wikipedia. 2022. "Leonardite" Wikimedia Foundation. Sep. 6, 2017 <https://en.wikipedia.org/wiki/Leonardite> (Year: 2017).*

Almendros, G. et al., Depolymerization and Degradation of Humic Acids with Sodium Perborate, Geoderma, vol. 39, (1987):235-247.

Amon, R.M.W. et al., Bacterial utilization of different size classes of dissolved organic matter, Limnol. Oceanogr., vol. 41, 1 (1996):41-51.

Asing, J. et al., Optimization of extraction method and characterization of humic acid derived from coals and composts, J. Trop. Agric. and Fd. Sc., vol. 37, 2 (2009):211-223.

Atiyeh, R., et al., The influence of humic acids derived from earthworm-processed organic wastes on plant growth, Bioresource Technology, vol. 84, 1 (2002):7-14.

Badis, A. et al., Characterization and biodegradation of soil humic acids and preliminary identification of decolorizing actinomycetes at Mitidja plain soils, African Journal of Microbiology Research, vol. 3, 13 (2009):997-1007.

Bai, Y. et al., Aerobic degradation of pyridine by a new bacterial strain, Shinella zoogloeoides BC026. Journal of industrial microbiology & biotechnology, vol. 36, 11 (2009):1391-400.

Basta, T. et al., Structural and replicative diversity of large plasmids from sphingomonads that degrade polycyclic aromatic compounds and xenobiotics, Microbiology, vol. 151, (2005):2025-2037.

Basu, A. et al., Preferential utilization of aromatic compounds over Glucose by Pseudomonas putida CSV86, Applied and Environmental Microbiology, vol. 72, 3 (2006):2226-2230.

Baylon, M.G. et al., Bio-solubilization of the untreated low rank coal by alkali-producing bacteria isolated from soil, Korean J. Chem. Eng., vol. 34, (2017):105-109.

Biala, S. et al., Biodegradation of 4-aminobenzenesulfonate by indigenous isolate Shinella yambaruensis SA1 and its validation by genotoxic analysis, Biotechnol and Bioprocess Engin., vol. 10, (2014):1034-1041.

Billingham, K., Humic Products—Potential or presumption for agriculture, 2012.

Bowman, J.P. et al., Revised taxonomy of the methanotrophs: description of *Methylobacter* gen. nov., emendation of Methylococcus, validation of *Methylosinus* and *Methylocystis* species, and a proposal that the family Methylococcaceae includes only the group I methanotrophs, IJSEM, vol. 43, (1993):735-753.

Calvo, P. et al., Agricultural uses of plant biostimulants, Plant Soil, vol. 383, (2014):3-41.

Cubillos-Hinojosa, J.G. et al., Assessment of a low rank coal inoculated with coal solubilizing bacteria as an organic amendment for a saline-sodic soil, Chem. Biol. Technol. Agric. vol. 2, 21 (2015):1-10.

David, J. et al., The physico-chemical properties and biostimulative activities of humic substances regenerated from lignite, SpringerPlus, vol. 3, (2014):156.

David, Y. et al., Screening of Microoganisms able to Degrade Low-rank Coal in Aerobic Conditions: Potential Coal Biosolubilization Mediators from Coal to Biochemicals, Biotechnology and Bioprocess Engineering, vol. 22, (2017):178-185.

De Melo, B.A.G. et al., Humic acids: Structural properties and multiple functionalities for novel technological developments, Materials Science & Engineering. C, Materials for Biological Applications, vol. 62, (2016):967-974.

Derecho, I. et al., Characterization of Hydrogen Peroxide-Resistant *Acinetobacter* Species Isolated during the Mars Phoenix Spacecraft Assembly, Astrobiology, vol. 14, 10 (2014):837-847.

Dong, H. et al., Rhamnolipids Produced by Indigenous Acinetobacter junii from Petroleum Reservoir and its Potential in Enhanced Oil Recovery, Frontiers in Microbiology, vol. 7, 1710 (2016).

Dong, L. et al., Changes of chemical properties of humic acids from crude and fungal transformed lignite, Fuel, vol. 85, (2006):2402-2407.

Engesser, K. et al., Microbial degradation of model compounds of coal and production of metabolites with potential commercial value, Fuel Processing Technology, vol. 40, (1994):217-226.

Enkh-Oyun, T. et al., Isolation of Bioactive Substance from Pure Mumie, Journal of Agricultural Sciences, vol. 11, 2 (2013):33-35.

Fakoussa, R.M. et al., Biotechnology and microbiology of coal degradation, Appl. Microbiol Biotechnol., vol. 52, (1999):25-40.

(56) References Cited

OTHER PUBLICATIONS

Fernandez-Escobar, R. et al., Response of olive trees to foliar application of humic substances extracted from leonardite, Scientia Horticulturae, vol. 66, (1996):191-200.
Fiorentino, N. et al., Giant reed growth and effects on soil biological fertility in assisted phytoremediation of an industrial polluted soil, Science of The Total Environment, vol. 575, (2017):1375-1383.
Gan, D. et al., Evaluation of a spectro-photometric method for practical and cost effective quantification of fulvic acid, Annals of Environmental Science, vol. 1, (2007):11-15.
Gao, T. et al., Biodegradation of Leonardite by an Alkali-producing bacterial community and characterization of the degraded products, Appl. Microbiol. Biotechnol., vol. 93, (2012):2581-2590.
Gao, T.G. et al., Nodulation characterization and proteomic profiling of Bradyrhizobium liaoningenese CCBAU05525 in Response to Water-Soluble Humic Materials, Scientific Reports, vol. 5, (2015):10836.
Garcia, A.C. et al., Involvement of Hormone-and ROS-signaling pathways in the Beneficial Action of Humic Substances on Plants Growing under Normal and Stressing Conditions, BioMed Research International, (2016):1-13.
Garcia, A.C. et al., Structure-Property-Function relationship in humic substances to explain the biological activity in plants, Scientific Reports, vol. 6, (2016): 20798.
Georgieva, T. et al., Comparative study of the efficacy of chemically and biologically extracted humic substances from various materials on the development of Poinsettia, Geophysical Research Abstracts, vol. 19, (2017):17606.
Ghabbour, E.A. et al., Spectrophotometric analysis of fulvic acid solutions—a second look, Annals of Environmental Science, vol. 3, (2009):131-138.
Ghosal, D. et al., Current state of knowledge in Microbial Degradation of Polycyclic Aromatic Hydrocarbons (PAHs): A review, Frontiers in Microbiology, vol. 7, (2016):1369.
Gonzalo, G. et al., Bacterial enzymes involved in lignin degradation, Journal of Biotechnology, vol. 236, (2016):110-119.
Gramss, G. et al., Degradation of Soil Humic Extract by Wood-and-Soil-Associated Fungi, Bacteria, and Commercial Enzymes, Microbial Ecology, vol. 37, (1999):140-151.
Grasset, L. et al., Structure of humin and humic acid from an acid soil as revealed by phase transfer catalyzed hydrolysis, Org. Geochem., vol. 29, 4 (1998):881-891.
Han, R., Phthalate biodegradation: gene organization, regulation and detection, 2008.
Helal, A.A. et al., Characterization of different humic materials by various analytical techniques, Arabian Journal of Chemistry, vol. 4, (2011):51-54.
Hesham, A. et al., Biodegradation ability and catabolic genes of petroleum-degrading Sphingomonas koreensis Strain ASU-06 isolated form Egyptian oily soil, BioMed Res Int., 2014 (2014): 127674.
Hofrichter, M. et al., Microbial Degradation and Modification of Coal, (2005):393-407.
International Preliminary Report on Patentability issued in PCT/US2019/064039, dated May 25, 2021.
International Search Report and Written Opinion issued in PCT/US2019/064039, mailed Mar. 19, 2020.
Kallenbach, C.M. et al., Direct evidence for microbial-derived soil organic matter formation and its ecophysiological controls, Nature Communications, vol. 7, (2016):1-10.
Kampfer, P. et al., *Camelimonas lactis* gen. nov., sp. nov., isolated from the milk of camels, International Journal of Evolutionary Microbiology, vol. 60, (2010):2382-2386.
Kulikova, N.A. et al., Label distribution in tissues of wheat seedlings cultivated with tritium-labeled leonardite humic acid, Scientific Reports, vol. 6, (2016):1-10.
Kussow, W., Humate and Humic Acid, Horticulture Update, 2002.
Ladino-Orjuela, G. et al., Metabolic pathways for degradation of aromatic hydrocarbons by bacteria, Reviews of Environmental Contamination and Toxicology, vol. 237, (2016):105-121.
Lamar, R.T. et al., A new standardized method for quantification of humic and fulvic acids in humic ores and commercial products, Journal of AOAC International, vol. 97, 3 (2014):721-730.
Lee, J.S. et al., *Sphingomonas aquatilis* sp. nov., *Sphingomonas koreensis* sp. nov. and *Sphingomonas taejonensis* sp. nov., yellow-pigmented bacteria isolated from natural mineral water, International Journal of Systematic and Evolutionary Microbiology, vol. 51, (2001):1491-1498.
Lukehurst, C.T. et al., Utilisation of digestate from biogas plants as biofertiliser, Digestate Brochure, 2010.
Lv, D. et al., Experimental Study on Micro-Biological Degradation of 1, 3, 5-TMB in Groundwater, J of Clean Energy Technol, vol. 2, 2 (2014): 183-186.
Mackowiak, C.L. et al., Beneficial Effects of Humic Acid on Micronutrient Availability to Wheat, Soil Sci. Soc. Am. J., vol. 65, (2001):1744-1750.
Malik, A. et al., Intergeneric coaggregations among *Oligotropha carboxidovorans* and *Acinetobacter* species present in activated sludge, FEMS microbiology letters, vol. 224, 1 (2003):23-28.
Moreno, J.L. et al., Compost, leonardite, and zeolite impacts on soil microbial community under barley crops, Journal of Soil Science and Plant Nutrition, vol. 17, 1 (2017):214-230.
Nardi, S. et al., Plant biostimulants: physiological responses induced by protein hydrolyzed-based products and humic substances in plant metabolism, Scientia Agricola, vol. 73, 1 (2016):18-23.
Nemec, A. et al., *Acinetobacter beijerinckii* sp. nov. and *Acinetobacter gyllenbergii* sp. nov., haemolytic organisms isolated from humans, International journal of systematic and evolutionary microbiology, vol. 59, Pt 1 (2009):118-124.
No Author, Utilization of Lignite, 1 page.
Ohadi, M. et al., Isolation, characterization, and optimization of biosurfactant production by an oil-degrading Acinetobacter junii B6 isolated from an Iranian oil excavation site. Biocatalysis and Agricultural Biotechnology, vol. 12, (2017):1-9.
Orlov, D.S. et al., Soil organic matter and protective functions of humic substances in the biosphere, Use of Humic Substances to Remediate Polluted Environments: From Theory to Practice, chapter 2, 2017.
Petrov, D. et al., Molecular dynamics simulations of the standard leonardite humic acid: microscopic analysis of the structure and dynamics, Environ. Sci. Technol., vol. 51, (2017):5414-5424.
Poehlein, A. et al., Genome sequence of *Shinella* sp. strain DD12, isolated from homogenized guts of starved Daphnia magna, Stand in Genomic Sci, vol. 11, 14 (2016).
Qiu, J. et al., A Novel (S)-6-Hydroxynicotine Oxidase Gene from *Shinella* sp. Strain HZN7, Appl Environ Microbiol., vol. 80, 18 (2014):5552-5560.
Qiu, J. et al., The Complete Genome Sequence of the Nicotine-Degrading Bacterium *Shinella* sp. HZN7, Frontiers Microbiol., vol. 7, 1348 (2016).
Ramunni, A. et al., Decomposition of humic acids by incubation in a soil water-extract under various conditions of oxygen availability, Plant and Soil, vol. 97, (1987):15-23.
Ramunni, A. et al., Humin susceptibility to microbial decomposition in a mollic vitrandept soil by "in vitro" experiments, The Science of the Total Environment, vol. 62, (1987):413-417.
Ricca, G. et al., Structural investigations of humic acid from leonardite by spectroscopic methods and thermal analysis, Geoderma, vol. 57, (1993):263-274.
Romanowska, I. et al., Biosolubilization of Polish brown coal by Gordonia alkanivorans S7 and Bacillus mycoides NS1020, Fuel Processing Technology, vol. 131, (2015):430-436.
Rose, M.T. et al., Chapter Two—A Meta-Analysis and Review of Plant-Growth Response to Humic Substances: Practical Implications for Agriculture, Advances in Argonomy, vol. 124, (2014):37-89.
Saisa-Ard, K. et al., Isolation and characterization of biosurfactants-producing bacteria isolated from palm oil industry and evaluation for biosurfactants production using low-cost substrates, BioTechnologia. Journal of Biotechnology Computational Biology and Bionanotechnology, vol. 94, 3(2013):275-284.

(56) References Cited

OTHER PUBLICATIONS

Saito, B. et al., Alkaline extraction of humic substances from pear applied to organic-mineral fertilizer production, Brazilian Journal of Chemical Engineering, vol. 31, 3 (2014):675-685.
Schaeffer, A. et al., From humic substances to soil organic matter-microbial contributions. In honour of Konrad Haider and James P. Martin for their outstanding research contribution to soil science, Journal of Soils and Sediments, vol. 15, (2015):1865-1881.
Schnitzer, M., Principles and Processes, Organic Matter, 2005.
Sen, I.K. et al., Structural and immunological studies of an exopolysaccharide from Acinetobacter junii BB1A, Carbohydrate Polymers, vol. 101, (2014):188-195.
Sharma, H.S.S. et al., Physicochemical analyses of plant biostimulant formulations and characterisation of commercial products by instrumental techniques, Chem. Biol. Technol. Agric., vol. 3, 13 (2016):1-17.
Silva, G., Soybean yield response to foliar applied humic acid and fungicide, Michigan State University field study, 2017.
Tahir, M.M. et al., Lignite-derived humic acid effect on growth of wheat plants in different soils, Pedosphere, vol. 21, 1 (2011):124-131.
Tikhonov, V.V. et al., Effects of Humic Acids on the Growth of Bacteria, Eurasian Soil Science, vol. 43, 3 (2010):305-313.
Tirandaz, H. et al., *Pseudorhodoplanes sinuspersici* gen. nov., sp. nov., isolated from oil-contaminated soil, IJSEM, vol. 65, (2015):4743-4748.
Ueno, A. et al., Anaerobic decomposition of humic substances by Clostridium from the deep subsurface, Scientific Reports, vol. 6, (2016):18990.
Ueno, A. et al., Supplementary Information: Anaerobic decomposition of humic substances by Clostridium from the deep subsurface, (2016):1-9.
Valero, N. et al., Production of humic substances through coal-solubilizing bacteria, Brazilian Journal of Microbiology, vol. 45, 3 (2014):911-918.
Vamsee-Krishna, C. et al., Bacterial degradation of phthalate isomers and their esters, Indian J. Microbiol., vol. 48, (2008):19-34.
Vaz-Moreira, I. et al., *Shinella fusca* sp. nov., isolated from domestic waste compost, IJSEM, vol. 6, (2010):144-148.
Wang, L. et al., Diverse bacteria with Lignin degrading potentials isolated from two ranks of coal, Frontiers in Microbiology, vol. 7, 1428 (2016).
Wu, H. et al., Biodegradation mechanism of 1H-1,2,4-triazole by a newly isolated strain *Shinella* sp. NJUST26, Scientific Reports, vol. 6, (2016).
Yuan, H. et al., Production of alkaline materials, surfactants and enzymes by Penicillium decumbens strain P6 in association with lignite degradation/solubilization, Fuel, vol. 85, (2006):1378-1382.
Zadow, R., The real dirt on Humic Substances, Maximum Yield Canada, 2009.
Zelibor, J.L. et al., Comparative analysis of the chemical composition of mixed and pure cultures of green algae and their decomposed residues by C nuclear magnetic resonance spectroscopy, Applied and Environmental Microbiology, vol. 54, 4 (1988):1051-1060.
Zhang, C. et al., Current Progress on Butyric Acid Production by Fermentation, Curr. Microbiol., vol. 59, (2009):656-663.
Zhang, D. et al., Humin as an electron donor for enhancement of multiple microbial reduction reactions with different redox potentials in a consortium, Journal of Bioscience and Bioengineering, vol. 119, 2 (2015):188-94.
Zhang, Y. et al., Extracellular polymeric substances govern the development of biofilm and mass transfer of polycyclic aromatic hydrocarbons for improved biodegradation, Bioresource Technology, vol. 193, (2015):274-280.
Klucakova, Martina, et al., Size and Charge Evaluation of Standard Humic and Fulvic Acids as Crucial Factors to Determine Their Environmental Behavior and Impact. Frontiers in chemistry 6:1-8 (2018).
U.S. Appl. No. 17/298,786 Office Action dated Feb. 26, 2024.
U.S. Appl. No. 17/298,786 Office Action dated Jul. 18, 2024.
U.S. Appl. No. 17/298,786 Office Action dated Feb. 21, 2025.

* cited by examiner

BIOLOGICAL DEGRADATION OF LOW-RANK COALS

CROSS-REFERENCE TO RELATED APPLICATIONS

This application is a continuation of U.S. application Ser. No. 17/298,786, filed on Jun. 1, 2021, which is a national phase application under 35 U.S.C. § 371 of PCT Application No. PCTUS2019/064039, filed Dec. 2, 2019, which claims priority to U.S. Provisional Application No. 62/773,541, filed on Nov. 30, 2018, which are hereby incorporated by reference in their entirety.

FIELD

The disclosure is generally related to biological methods of degrading low-rank coals to produce aerobic degradation products, including organic acids. The disclosure also provides related multiphase bioreactor systems for use in the biological methods.

BACKGROUND

Humic organic substances, such as organic acids, are complex organic molecules that occur in the environment (e.g., soils, sediments, and water). Humic organic acids such as humic, fulvic, ulmic acids, and aliphatic organic acids positively affect the uptake of nutrients by plants, bind metal ions, and support microbial survival within the soil environment. In particular, the humic-base organic acids increase nutrient availability in the soil. For example, humic and fulvic acids increase the availability of phosphorus and nitrogen in both calcareous soils and acidic soils. Humic molecules also increase the sorption of micronutrients (e.g., zinc and copper). Given the scarce levels of micronutrients in the soil, the ability of humic organic acids to promote the bioavailability of micronutrients provides significant benefits to soil nutrient properties in areas proximate to the plants.

Low-ranked coals, such as the upper sub-surface layer leonardite, are sources of humic organic acids. Leonardite is an oxidized lignite coal, containing about 55% carbon content. The nature of the leonardite has an effect on the quality of its humic substances due to variable decomposition rates and geochemical formations in the underground soil environment.

Conventional physicochemical methods for the production of humic organic acids from leonardite employ extraction methods using high-concentration alkaline and acid treatments of leonardite facilitated by exothermic heat from the process. Conventional extraction processes routinely result in low conversion rates to free humic organic acids, loss of molecular and functional integrity of the extracted humic organic acid, significant environmental issues, and high cost. For example, during alkaline-acid treatment, a strong caustic solution (which includes sodium hydroxide, potassium hydroxide, and/or calcium hydroxide) is used to extract humic organic acids from leonardite. The extraction is followed by acid precipitation of the extracted humic organic acids using a strong mineral acid. Such methods are accompanied by a number of concerns, including the necessary use of highly caustic solutions, low extraction efficiency (<8 wt %), and low recovery rate. These extraction methods typically result in low concentrations of free organic acids, and limited ability to control the humic organic acid composition. Moreover, products resulting from conventional approaches are often high in humin, dark solid particulates from humic substances. The high humin content makes such products highly viscous, with major handling issues in agricultural applications. Further, the humic organic acids produced in these conventional chemical extraction methods have relatively low free organic acid moieties. It can be inferred that these conventional methods generate organic acids either bound in a carbon matrix, ketonized in the process through covalent assembly, or bound strongly on a polyvalent metal ion, making the acids unavailable for chelation or cation exchange in formulations and soil environments.

Other methods used in the production of humic organic acids include cross-linking with aldehydes and cross-linking with polyvalent cations. The cross-linking takes place via the carboxylic groups and the phenolic OH groups present in the structure of humic acid. Humates from divalent metals such as calcium, magnesium, and barium are mostly water insoluble, whereas sodium and potassium humates are soluble. The humates from low-rank coal are mainly insoluble.

When humic organic acids are extracted with an aqueous solution of sodium hydroxide, humates that contain humic organic acids are first dissolved in the extracting solution and separated from insoluble tailings. The extracts from the humates are then acidified to precipitate the humic organic acids. For example, liquid alkali metal humic acid salt (e.g., Humasorb-L®) can be extracted from lignite, and humic acids in a solid form (e.g., Humasorb-S®) are soluble only at higher pH values and are obtained by precipitation of Humosorb-L® with HCl and then by purification. See, e.g., U.S. Pat. Nos. 5,906,960 and 6,143,692.

However, this approach is extremely inefficient at extracting humic organic acids, as less than 8% of humic acids can be dissolved in even strongly caustic solutions. The low volume of soluble humic organic acid in the solution would subsequently lead to even smaller amounts of humic organic acid that can be precipitated from the solution. Furthermore, the humic organic acids produced in these processes are either bound in carbon matrix, ketonized in the process through covalent assembly, or bound strongly on a polyvalent metal ion, making them unavailable for chelation or cation exchange in formulations and soil environments.

SUMMARY

In a first aspect, described herein are methods and processes for producing aerobic digestion products from a low-rank coal substrate and/or a consortium of low-rank coal-degrading microbes. The aerobic digestion products include, for example, organic acids, low-rank coal derivatives (i.e., low-rank coal digestion products that are not organic acids), and primary and secondary microbial metabolites. In certain embodiments, the methods comprise combining a low-rank coal substrate, water, a rock phosphate, and yeast to form an aqueous mixture, incubating the aqueous mixture under aerobic conditions, and collecting a fraction of the aqueous mixture comprising aerobic digestion products and/or the consortium of low-rank coal-degrading microbes. In some embodiments, the incubating step occurs in two or more stages.

In some embodiments, the incubation step occurs at a temperature from 15° C. to 50° C.

In some embodiments, the incubating step occurs in a multistage bioreactor system. In some embodiments, the multistage bioreactor system comprises two or more bioreactors. In some embodiments, the aqueous mixture is recycled within the two or more bioreactors at least once. In some embodiments, the incubation of the aqueous mixture occurs in one or more reactors selected from: a fluidized bed reactor; a plug flow fluidized bed reactor; and a combination thereof.

In some embodiments, additional yeast is incorporated into the aqueous mixture at least once during the incubation step.

In some embodiments, the methods further comprise collecting at least one intermediate fraction of the aqueous mixture, wherein the at least one intermediate fraction of the aqueous mixture is collected at an earlier time point than a final fraction.

In some embodiments, the methods further comprise recovering aerobic digestions products by separating a supernatant phase from a floc phase, wherein the supernatant phase comprises desired aerobic digestion products and the floc phase comprises solids and dense humic substances.

In some embodiments, the supernatant phase and the floc phase separate by gravity in a settling tank, or by centrifugation. In some embodiments, the settling tank is not substantially aerated or is not aerated.

In some embodiments, the methods further comprise concentrating the final fraction of the aqueous mixture or the intermediate fraction of the aqueous mixture comprising the aerobic digestion products.

In some embodiments, the final fraction of the aqueous mixture or the intermediate fraction of the aqueous mixture comprising the aerobic digestion products is concentrated by at least one method selected from evaporation, thin film evaporation, electro-coagulation, magnetic separation, and nanofiltration. In some embodiments, the supernatant phase is concentrated.

In some embodiments, the methods further comprise separating the produced aerobic digestion products according to molecular weight.

In some embodiments, the methods further comprise monitoring an E4/E6 ratio, a zeta potential, a chelation capacity, or a combination thereof during the incubation step. In some embodiments, the incubation step is continued until a preselected E4/E6 ratio is attained, a preselected zeta potential is attained, a preselected chelation capacity is attained, or a combination thereof.

In some embodiments, the incubation step is continued until a first preselected E4/E6 ratio is attained, a first preselected zeta potential is attained, a first preselected chelation capacity is attained, or a combination thereof, at which time a first intermediate fraction of the aqueous mixture is collected, and wherein the incubation step is continued following collection of the first intermediate fraction of the aqueous mixture until at least one other preselected E4/E6 ratio is attained, one other preselected zeta potential is attained, one other preselected chelation capacity is attained, or a combination thereof, at which time an additional intermediate fraction of the aqueous mixture is collected or the final fraction of the aqueous mixture is collected.

In some embodiments, monitoring chelation capacity comprises: a) applying a sample of the aqueous mixture to a target agricultural soil; b) drying the sample-target agricultural soil mixture; c) incubating the dried mixture with a standardized ion solution; d) separating target agricultural soil from supernatant by centrifugation and filtration; measuring ion concentration in the supernatant; e) calculating ions remaining in treated target agricultural soil; 0 calculating chelation capacity on a mass chelated ion per unit quantity of aqueous mixture basis.

In some embodiments, the low-rank coal substrate has a particle size of 0.001 mm to 0.1 mm. In some embodiments, the low-rank coal substrate is selected from: peat, lignite; leonardite; subbituminous coal; or a mixture thereof.

In some embodiments, the methods further comprise pretreating the low-rank coal substrate. In some embodiments, the low-rank coal substrate is pretreated with an alkaline solution.

In some embodiments, the alkaline solution has a concentration of 0.05 M or less.

In some embodiments, the methods further comprise incorporating an exogenous microbial stock solution into the aqueous mixture. The microbial stock solution includes microbes capable of degrading a low-rank coal, such as leonardite or peat. In some embodiments, the microbial stock solution comprises microbes capable of growing on alkalinized leonardite media (ALM).

In some embodiments, the microbial stock solution comprises one or more bacteria selected from: *Shinella* spp., *Sphingomonas* spp., *Camelimonas* spp., *Sphingopyxis* spp., *Acinetobacter* spp., *Microbacterium* spp., *Methylocystis* spp., and *Pseudorhodoplanes* spp.

In some embodiments, the aerobic digestion products include organic acids, wherein the organic acids are humic acids, ulmic acids, fulvic acids, or a combination thereof. In addition to organic acids, aerobic digestion products have also been shown to contain esters, alcohols, phenols, amines, and phthalates.

In a second aspect, provided herein are product compositions comprising one or more aerobic digestion products produced by the methods and processes described herein, and methods for their use. In certain embodiments, the aerobic digestion products have a zeta potential lower than −10 mV. In some embodiments, the product composition is a liquid fertilizer.

In a third aspect, provided herein are methods for improving plant growth and/or soil quality, the method including applying a composition comprising aerobic digestion products produced by the methods described herein to a plant, to a soil, or to both a plant and a soil. In some embodiments, the composition is applied to the soil where a plant grows or will grow, to seeds of a plant, or to a plant. The composition can be applied in-furrow, as a foliar spray, in the vicinity of roots of the plant, to parts of the plant, to a rooting zone, to an area proximate to the plant, or a combination thereof. In some embodiments, the composition is applied at a rate of about 0.5 quarts per acre to about 10 quarts per acre. In some embodiments, the composition can include at least 0.01 ppm of the aerobic digestion products.

In a fourth aspect, provided herein is a selective bacterial growth media comprising leonardite treated with an alkaline solution. In some embodiments, the alkaline solution is potassium hydroxide. The potassium hydroxide may be about 0.03M potassium hydroxide. Optionally, the selective bacterial growth media comprises one or more of a salt solution, a trace mineral solution, and noble agar.

In a fifth aspect, provided herein is a method for selecting one or more low-rank coal-degrading microbes. In some embodiments, the method includes growing a consortium of bacteria on a selective bacterial growth media described herein, and selecting one or more microbes capable of growing on the selective bacterial growth media.

In a sixth aspect, provided herein are multistage bioreactor systems for carrying out the described methods and processes. In some embodiments, the multistage bioreactor systems comprise two or more bioreactors. In some embodiments, the bioreactors of the multistage bioreactor systems are fluidized bed reactors or plug flow fluidized bed reactors.

BRIEF DESCRIPTION OF THE DRAWINGS

FIG. 5A) and the supernatant phase of the system product (FIG. 5B) from a bioreactor system according to an embodiment of the present disclosure. LC-MS of a commercial product is included for comparison (FIG. 5C).

DETAILED DESCRIPTION

Figure 1:
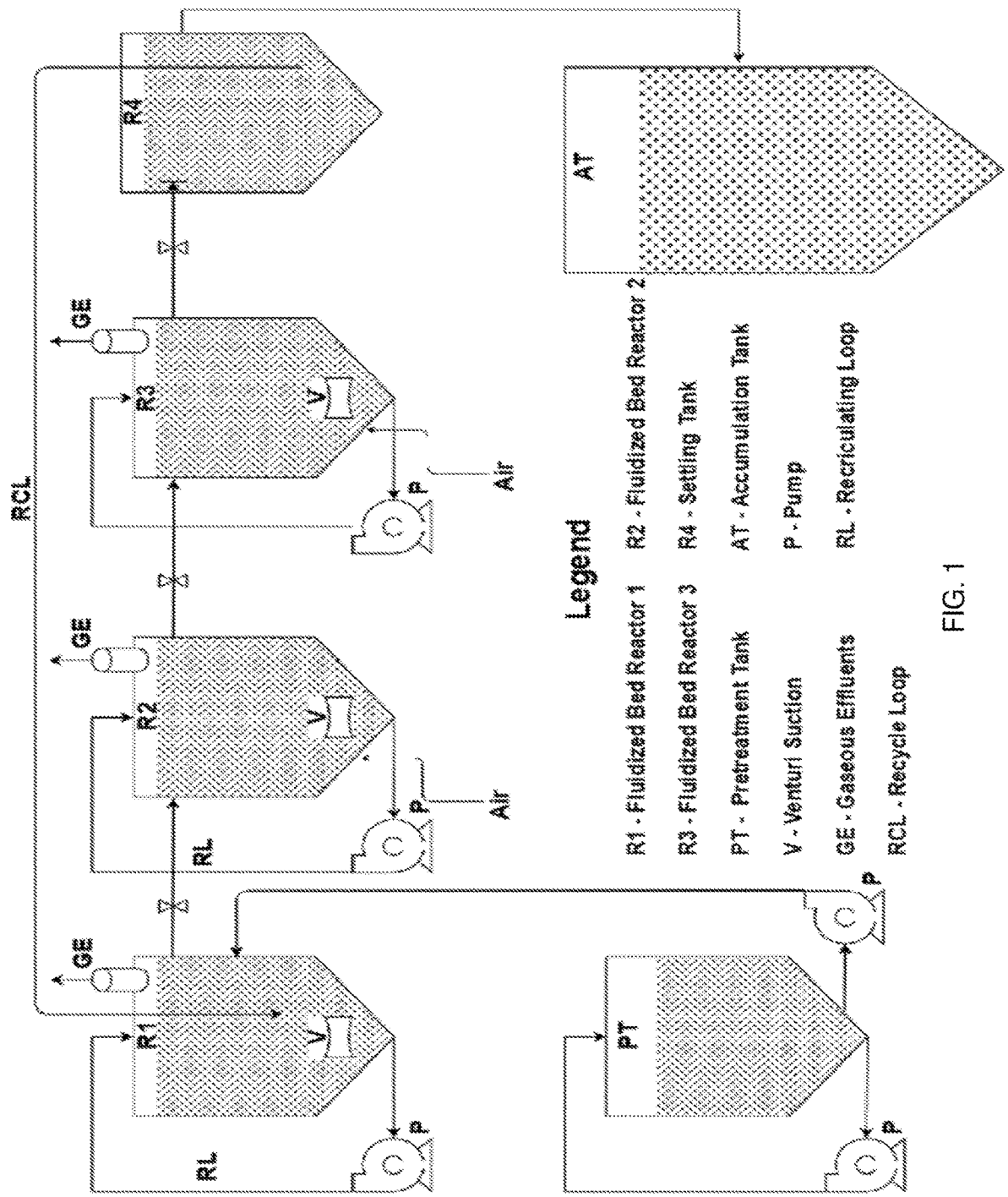
FIG. 1 is a diagram illustrating a bioreactor system according to one embodiment of the present disclosure.

While the disclosed subject matter is amenable to various modifications and alternative forms, specific embodiments are described herein in detail. The intention, however, is not to limit the disclosure to the particular embodiments described. On the contrary, the disclosure is intended to cover all modifications, equivalents, and alternatives falling within the scope of the disclosure as defined by the appended claims.

Similarly, although illustrative methods may be described herein, the description of the methods should not be interpreted as implying any requirement of, or particular order among or between, the various steps disclosed herein. However, certain embodiments may require certain steps and/or certain orders between certain steps, as may be explicitly described herein and/or as may be understood from the nature of the steps themselves (e.g., the performance of some steps may depend on the outcome of a previous step).

Definitions

Unless defined otherwise, all technical and scientific terms used herein shall have their same meaning as commonly understood by one of ordinary skill in the art to which this disclosure pertains.

In this specification and in the claims that follow, reference will be made to a number of terms that shall be defined to have the following meanings.

The terminology used herein is for the purpose of describing particular embodiments only and is not intended to be limiting of the disclosure. As used herein, the singular forms "a," "an," and "the" are intended to include the plural forms as well, unless the context clearly indicates otherwise.

A "set," "subset," or "group" of items may include one or more items, and, similarly, a subset or subgroup of items may include one or more items. A "plurality" means more than one.

All numerical designations, e.g., pH, temperature, time, concentration, amounts, and molecular weight, including ranges, are approximations which are varied by +/−10%, 1%, or 0.1%, as appropriate. It is to be understood, although not always explicitly stated, that all numerical designations may be preceded by the term "about." It is also to be understood, although not always explicitly stated, that the reagents described herein are merely exemplary and that equivalents of such are known in the art.

As the terms are used herein with respect to ranges, "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error, differences in measurement and/or manufacturing equipment calibration, human error in reading and/or setting measurements, adjustments made to optimize performance and/or structural parameters in view of differences in measurements associated with other components, particular implementation scenarios, imprecise adjustment and/or manipulation of objects by a person or machine, and/or the like. The term "about," when used before a numerical designation, e.g., temperature, time, amount, concentration, and such others, including a range, indicates approximations which may vary by +/−10%, 5%, 1%, or any subrange or subvalue therebetween. Preferably, the term "about" when used with regard to an amount of a compound or composition amount means that the amount may vary by +/−10%.

As used herein, the term "effective amount" refers to an amount of a composition capable of achieving a desirable result, which include but are not limited to promoting plant growth, improving soil quality, or removing or sequestering heavy metals. The precise effective amount will vary based on the type of plants, the type of metals to be removed, pH, and/or the types of leonardite or other low rank coal substrates.

As used herein, the term "plant" or "plants" means, in a broad sense, not only herbaceous varieties, including but not limited to crops, vegetables, flowers, foliage plants, turf grasses, and fruits, but also trees, shrubs, and the like. Non-limiting examples of crops include corn, rice, wheat, barley, rye, oat, sorghum, cotton, soybean, peanut, buckwheat, beet, rapeseed, sunflower, sugar cane, marijuana, and tobacco. Non-limiting examples of vegetables include solanaceous vegetables (eggplant, tomato, pimento, pepper, potato, etc.), cucurbitaceous vegetables (cucumber, pumpkin, zucchini, watermelon, melon, squash, etc.), cruciferous vegetables (Japanese radish, white turnip, horseradish, kohlrabi, Chinese cabbage, cabbage, leaf mustard, broccoli, cauliflower, etc.), asteraceous vegetables (burdock, crown daisy, artichoke, lettuce, etc.), liliaceous vegetables (green onion, onion, garlic, and asparagus), ammiaceous vegetables (carrot, parsley, celery, parsnip, etc.), chenopodiaceous vegetables (spinach, Swiss chard, etc.), lamiaceous vegetables (*Perilla frutescens*, mint, basil, etc.), strawberry, sweet potato, *Dioscorea japonica*, and *colocasia*. The non-limiting examples of fruits include pomaceous fruits (apple, pear, Japanese pear, Chinese quince, quince, etc.), stone fleshy fruits (peach, plum, nectarine, *Prunus* mume, cherry fruit, apricot, prune, etc.), citrus fruits (Citrus unshiu, orange, lemon, rime, grapefruit, etc.), nuts (chestnuts, walnuts, hazelnuts, almond, pistachio, cashew nuts, macadamia nuts, etc.), berries (blueberry, cranberry, blackberry, raspberry, etc.), grape, kaki fruit, olive, Japanese plum, banana, coffee, date palm, avocado, and coconuts. Non-limiting examples of trees include fruit trees, tea, mulberry, flowering plant, and roadside trees (ash, birch, dogwood, *Eucalyptus, Ginkgo biloba*, lilac, maple, *Quercus*, poplar, Judas tree, *Liquidambar formosana*, plane tree, *Zelkova*, Japanese arborvitae, fir wood, hemlock, juniper, *Pinus, Picea*, and *Taxus* cuspidate). The term "plant" or "plants" refers to both native and genetically engineered aforementioned varieties.

The term "organic acid" refers to any acidic compound that comprises one or more carbon atoms. In one embodiment, the organic acid comprises a free organic acid. Non-limiting examples of organic acids include fulvic acid, humic acid, and ulmic acid. The term also includes aliphatic organic acids.

As used herein, the term "free organic acid" refers to an organic acid having active moieties that are readily available for chelation through electrostatic binding and/or metal ion coordination. The term "chelate" or "chelation" refers to the binding of a metal ion to a ligand (e.g., a free organic acid) by coordinating a covalent bond. Free organic acids, in some embodiments, are capable of chelating ions (e.g., cations) in the soil.

As used herein, the term "humic acid" refers to an acidic aromatic compound with a high molecular weight. In some embodiments, the molecular weight is in the range of from about 300 g/mol to about 300,000 g/mol, about 1,000 g/mol to about 200,000 g/mol, or about 2,000 g/mol to about 100,000 g/mol. The humic acid can be obtained from plant decomposition, such as coal. The humic acids often comprise carbonyl, lactone, carboxylic, and phenolic groups. Humic substances are generally not soluble in water, particularly under acidic conditions (e.g., pH<2), but the solubility increases at higher pH values. The ratio of C:O:H varies in different humic acids. In one embodiment, the ratio of C:O:H is approximately 2.4-3.0:1:1.

As used herein, the term "humate" refers to the products of natural flocculation or precipitation in sand deposits, or humic substances that were derived from leaching of decaying plants and animal materials (humus). The term, as used herein, includes both humate and humic acids found in humate. Humate has been used as plant fertilizer or animal food supplement.

The term "cation exchange capacity" or "CEC" refers to the quantity of negatively charged sites on soil surfaces that can bond with cations at a predefined pH. Common protocols for testing soil cation exchange capacity use a pH of 7 or 8.2. In one embodiment, CEC is related to various negative charges on particle surfaces, especially those of clay minerals and soil organic matter. In addition, organic matter can influence cation exchange capacity, due to its large number of charged functional groups. CEC varies at different layers in the soil. In one embodiment, CEC is higher near the soil surface, where organic matter content is highest, and declines with depth. In one embodiment, the CEC refers to the amount of cations held in soil. Given that several nutrients, e.g., $K^+$, $NH^{4+}$, $Ca^{2+}$, are positive in plant-available forms, the CEC is indicative of the capability of soil to hold nutrients.

Figure 6:
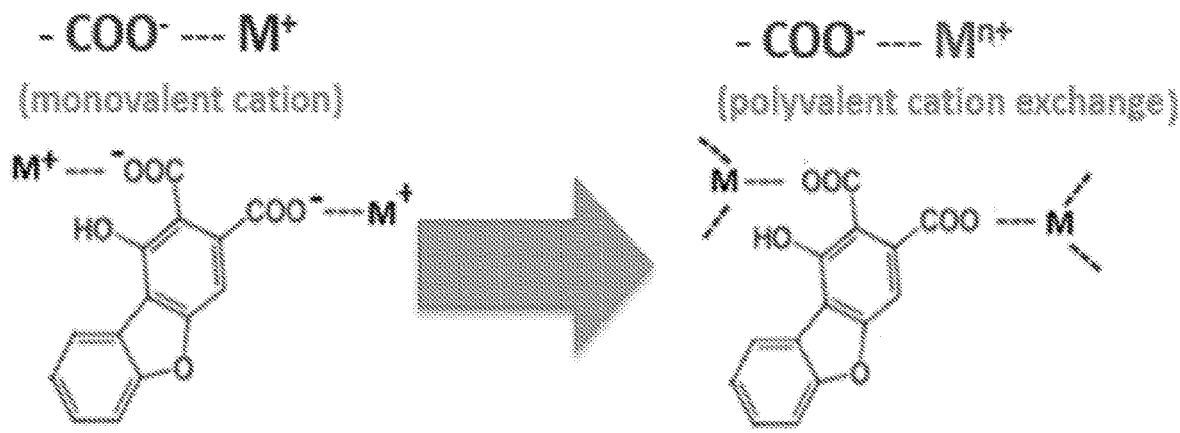
FIG. 6 is a schematic depicting humic acid cation exchange chemistry.
Figure 7:
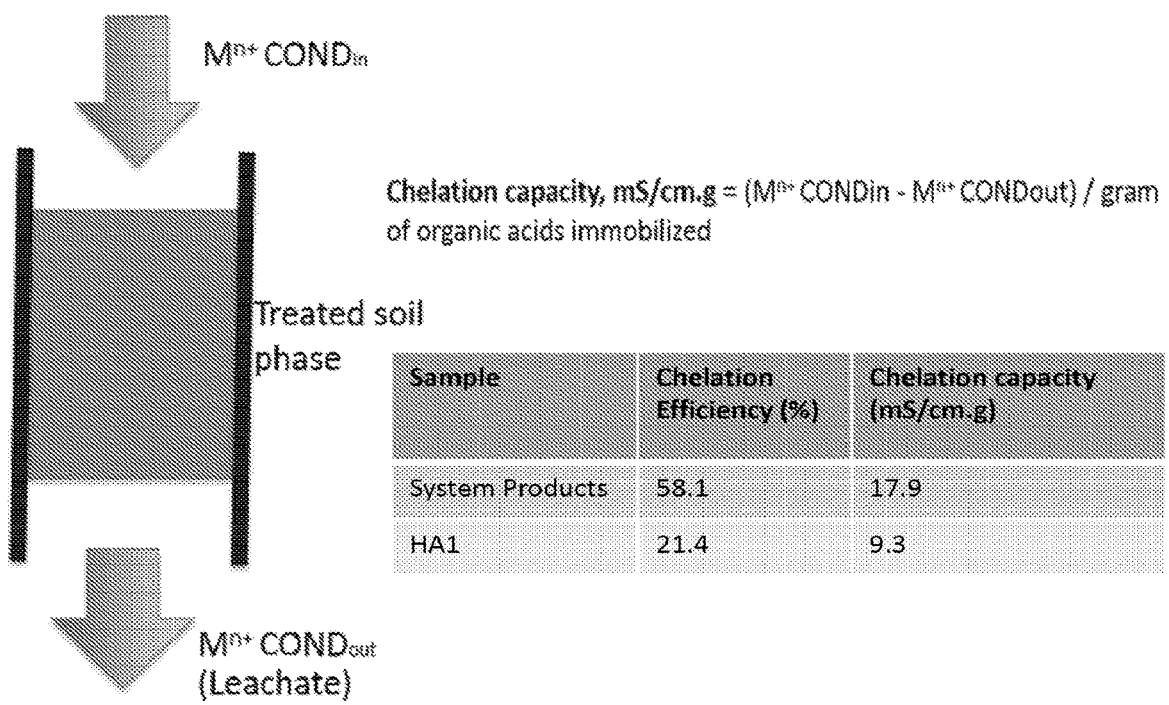
FIG. 7 presents the chelation capacities of a system product per gram organic acid from a bioreactor system according to an embodiment of the present disclosure relative to commercially available humic acid products.

The CEC, in one embodiment, is measured by the amount of positive charge that can be exchanged per mass of soil, usually measured in cmolc/kg, meq/100 g, meq/kg, meq/g, or other similar or equivalent units. For example, a cation exchange capacity of 10 $cmol_c$/kg may mean that 10 cmol of $Na^+$ cations (with 1 unit of charge per cation—"monovalent") can be held in a kilogram of soil, or only 5 cmol $Ca^{2+}$ (2 units of charge per cation—"polyvalent"). This is illustrated by FIG. 6.

A compound's CEC may be influenced by pH in the environment or soil, particularly for CEC of organic compounds. In some embodiments, an acidic pH increases this variable charge and therefore also increases the cation exchange capacity.

"Chelation capacity" refers to the amount of metal ions (from a single ion species solution) in moles or grams that can be chelated (bound) by chelants, like the free organic acids described herein, in solution on a per unit mass basis. Methods for determining chelation capacity are provided herein, for example, at Example 2.

"Chelation efficiency" refers to the percentage of metal ions in the soil compartment at native soil pH and at equilibrium with a supernatant created from the washed soil. See Example 2.

As used herein, the term "low-rank coal" refers to lignite, subbituminous coal, and the coal precursor peat. "Lignite," also called "brown coal," includes "leonardite," an oxidized form of lignite containing high levels of humic organic acids.

Aerobic Digestion Products of Low-Rank Coal

Humic acids are found in the brown organic matter of soils, peats, manure, and lignite. Humic acid does not have a single unique structure but is a mixture of intermediate chemical products resulting from the decomposition and conversion of lignin and other plant materials to coal. Humic acids can be produced by the degradation of organic matters (plant tissues) or other secondary processes (e.g., polymerization of polyphenols; and condensation of phenols, quinones, and proteins from soil microorganisms and small animals on soil carbohydrates).

Humic organic acids such as humic acids, fulvic acids, ulmic acids, and aliphatic organic acids are important to the uptake of nutrients by plants and the binding of metal ions in soil, as well as playing a role in supporting microbial survival within the soil environment. These attributes have resulted in humic substances being used as soil media, solid and liquid fertilizers, soil biostimulants, and chelation agents, resulting in high demands of humic substances and humic organic acids for agricultural applications.

Published research reports have evaluated different physicochemical functionalities of humic organic acids in enhancing soil fertility and plant growth. For example, humic substances can impact morphological features and yields of *Arnica montana* grown on sandy soils. Loading rates of leonardite, a low-rank coal rich in humic organic acids, have been positively correlated with soil quality, enzymatic activities of dehydrogenases, acid phosphatase, urease, and protease, as well as chemical properties of the soil. A noticeable improvement in plant growth was observed after treating less fertile soils with humic acids. For example, humic acids were used to treat industrially contaminated soils to successfully grow *Arundo donax*. This may be a result of direct and/or indirect effect. Direct improvement in plant growth may relate to enhanced uptake and transport of humic substances into plant tissues and indirect effects relate to improvements in soil properties such as structure, water retention, porosity, hormonal activities, growth of microbial materials, mineralization of organic matters, and cation and anion exchange capacity.

Leonardite, an upper sub-surface layer, low-ranked coal, is a reliable source of humic organic acids. Leonardite is an oxidized lignite coal containing humic substances.

Described herein are methods and systems capable of harnessing the ability of microorganisms to degrade low-rank coal directly to liberate bound humic organic acids and produce lower molecular weight organic acids. In some embodiments, the method includes continuous microbial release of aerobic digestion products (e.g., organic acids) from low-rank coal with simultaneous enrichment of the low-rank coal-degrading (e.g., leonardite-degrading) microbial communities and minimal waste production. Additionally, the methods described herein produce a flowable aqueous composite of low-rank coal-degrading microbial communities and aerobic digestion products, including free humic organic acids from the low-rank coal, low-rank coal derivatives (i.e., low-rank coal digestion products that are not organic acids), and primary and secondary microbial metabolites. The methods described herein further provide for customized humic organic acid production, wherein humic organic acids having specific, desired organic acid properties (e.g., E4/E6 ratio, chelation capacity, zeta potential) can be produced by altering processing parameters. In certain embodiments, the extraction of humic organic acids from low-rank coal is driven by preferential biological release (bio-leaching) of free and available organic acids from low-rank coals by creating a biophysical environment that allows organic acid moieties with high aqueous solubility to diffuse from a solid matrix into a liquid phase.

The described methods and systems provide for simultaneous enrichment of low-rank coal-degrading microbial consortia and continuous biological release of aerobic digestion products from low-rank coal. In particular, described herein are (1) microbial-driven biochemical processes for producing aerobic digestion products from low-rank coal, including biological release of aerobic digestion products from low-rank coal, production of low-rank coal derivatives, and production of primary and secondary microbial metabolites; (2) aerobic digestion products, including organic acids, low-rank coal derivatives, and primary and secondary microbial metabolites produced by the microbial-driven methods and processes; (3) compositions comprising flowable aqueous composite of low-rank coal-degrading microbial communities, humic-based organic acids from low-rank coal, low-rank coal derivatives, and/or primary and secondary microbial metabolites; (4) systems for continuous enrichment of low-rank coal-degrading microbial communities, simultaneous biological release of humic organic acids and low-rank coal derivatives, and production of primary and secondary microbial metabolites; (5) methods for improving plant growth; and (6) methods for removing and/or sequestering heavy metals from a soil or other environment.

The compositions and humic organic acids produced by the described methods and systems have improved chelation and cation exchange capacities per unit mass of humic organic acid relative to available humic organic acid products, and can be used, for example, for (1) reducing escape of beneficial cations from the soil environment by hindering the formation of insoluble complexes with soil anions; (2) enabling easy formulation of compositions with high cation exchange capacity and/or salt content; (3) introducing specialty metal ions to the soil for plant uptake, e.g., zinc and iron ions; (4) functioning as a vehicle to deliver a variety of highly plant-available micronutrients to the soil for plant uptake; (5) enhancing plants' resistance to salt stress through direct chelation of metal ions and redistribution across the soil bed; and (6) remediating soils with heavy metal contamination.

Methods and Processes for the Biological Release of Aerobic Digestion Products from Low-Rank Coal In a first aspect, provided herein are methods and processes for the biological release of aerobic digestion products from low-rank coal. The methods and processes are microbially-driven biological processes resulting in the degradation of the low-rank coal and release of the aerobic digestion products. The methods and processes described herein enrich microbial communities that break down high molecular weight humic substances and heavy organic acids into lower weight organic acids (e.g., fulvic acids and aliphatic organic acids), produce beneficial primary and secondary microbial metabolites, and generate low-rank coal derivatives.

The phased low-rank coal degradation process described herein offers the opportunity to harness the generation of different molecular weight organic acids over a wide spectrum, including humic, ulmic, and fulvic acids from one bioreactor to the other. The decreased aromaticity of the working solution from a first bioreactor to subsequent bioreactors suggests the microbial conversion of heavy humic substances into lighter ones. This creates a unique product development opportunity of tailoring the level of aromaticity and other product characteristics in product output. Such characteristics are unique to the methods, processes, and systems of the present disclosure. The processes described herein further generate unique low-rank coal derivatives, as well as primary and secondary microbial metabolites.

In certain embodiments, the method comprises combining a low-rank coal substrate with water, a phosphorous source, and yeast to form an aqueous mixture (i.e., working solution). The aqueous mixture is then incubated, and a fraction of the aqueous mixture comprising aerobic digestion products is collected.

In certain embodiments, the methods, processes, and related systems enhance the release of free and available humic organic acids from the low-rank coal substrate through the exploitation of the relative solubilities of the organic acid moieties in aqueous solution. Free organic acid molecules are highly soluble and have readily available sites for chelation and cation exchange.

In certain embodiments, the low-rank coal substrate is lignite (i.e., brown coal), leonardite, subbituminous coal, peat, or any combination of these. In certain embodiments, the low-rank coal substrate is leonardite. Often associated with near-surface lignite deposits, leonardite is an oxidation product of lignite.

In certain embodiments, the low-rank coal substrate is crushed, milled, or otherwise reduced to an appropriate size for processing. In some embodiments, particles of the low-ranked coal substrate have a size from about 0.001 mm to about 0.15 mm. In some embodiments, particles of the low-ranked coal substrate have a size from about 0.020 mm (635 mesh) to about 0.140 mm (100 mesh).

In certain embodiments, the water is tap water.

In certain embodiments, suitable sources of phosphorous include those sources capable of solubilization by low-rank coal-degrading microorganisms (e.g., those microorganisms capable of growing on alkalinized leonardite media (ALM)). For example, in certain embodiments, the phosphorous source is a rock phosphate. The phosphorous source has a suitable phosphorous pentoxide content. In certain embodiments, the phosphorous source has a phosphorous pentoxide content of about 4% to about 20% or may be enriched to a content of at least 28%. In certain embodiments, the rock phosphate has a phosphorous pentoxide content of about 4% to about 20% or is enriched to a phosphorous pentoxide content of at least 28%. In some embodiments, the rock phosphate is a source of micronutrients for low-rank coal-degrading microorganisms.

In certain embodiments, the yeast is *Saccharomyces cerevisiae*.

In certain embodiments, the low-rank coal substrate is pretreated with a low concentration alkaline solution prior to being mixed with the water, phosphorous source, and/or yeast. Pretreating leonardite, for example, with the low concentration alkaline solution may break down the waxy hydrophobic outer layer of leonardite, making the low-rank coal substrate more susceptible to microbial interaction in the aqueous mixture. Examples of low concentration alkaline solutions useful for pretreating the low-rank coal substrate include, but are not limited to, sodium hydroxide, potassium hydroxide, magnesium hydroxide, and calcium carbonate. Low concentration alkaline treatment of low rank coal substrate for the purposes of this document will be designated as "alkaline-treated low rank coal (or leonardite)". Lowering the concentration or the amount of the alkaline solution used for pretreatment of the low-rank coal substrate is important to avoid common problems associated with traditional chemical-based humic organic acid extraction methods. As the pretreatment process is not intended to completely break down the low-rank coal substrate, the concentrations of alkaline solution useful for pretreatment according to the methods described herein are lower than those used for conventional chemical extraction. In certain embodiments, the alkaline solution used to pretreat the low-rank coal substrate has a concentration of 0.01 M or less, 0.025 M or less, 0.05 M or less, or 0.1 M or less. In certain embodiments, the alkaline solution has a concentration greater than 0 and equal to or less than 0.05 M.

The alkaline-treated low-rank coal substrate and water are combined to form an aqueous mixture in a pretreatment tank. The phosphorous source and yeast may be added to the aqueous mixture in a first bioreactor. For example, in some embodiments, the low-rank coal substrate and water are combined in a pretreatment tank, and the phosphorous source and yeast are added to the alkaline-treated low-rank coal substrate and water in a bioreactor, resulting in an aqueous mixture. In some embodiments, the alkaline-treated low-rank coal substrate and water are combined in a pretreatment tank, the phosphorous source is added to the alkaline-treated low-rank coal substrate and water in a first bioreactor, and the yeast is added to the alkaline-treated low-rank coal substrate, water, and phosphorous source in a second bioreactor. In other embodiments, the alkaline-treated low-rank coal substrate, water, phosphorous source, and yeast are combined in the same tank. In other embodiments, the alkaline-treated low-rank coal substrate, water, and phosphorous source are combined in a first tank.

In certain embodiments, the entirety of the incubation of the aqueous mixture occurs in a single bioreactor (i.e., a single step). Where the incubation occurs in a single bioreactor, the aqueous mixture may be circulated within the bioreactor, and/or aerated.

In certain embodiments, the incubation of the aqueous mixture occurs in two or more stages. In some embodiments, each stage of the incubation occurs in a separate bioreactor. Thus, in some embodiments, the incubation of the aqueous mixture takes place in a multistage bioreactor system. An example of a multistage bioreactor system is depicted by FIG. 1. In certain embodiments, the multistage bioreactor system includes two or more bioreactors. In some embodiments, the multistage bioreactor system comprises 2-10 bioreactors. In certain embodiments, the multistage bioreactor system comprises 4 bioreactors. In addition to bioreactors, in certain embodiments, a multistage bioreactor system may include one or more pretreatment tanks, one or more settling tanks, one or more collection tanks, or any combination of at least two of these types of tanks.

In certain embodiments, the bioreactors of the multistage bioreactor systems are fluidized bed reactors, plug flow fluidized bed reactors, or a combination of these types of reactors. Multistage bioreactor systems useful in the methods provided herein are described herein in further detail.

In certain embodiments, at least a portion of the aqueous mixture is recycled amongst the bioreactors of a multistage bioreactor system at least once. For example, at least some of the aqueous mixture taken from the final bioreactor of the multistage bioreactor system is recycled to a bioreactor positioned earlier in the line of bioreactors. The recycled aqueous mixture continues the incubation process as it passes through consecutive bioreactors until it again reaches the final bioreactor, where it can be recycled again, or transferred to, for example, a settling tank. In some embodiments, at least some of the aqueous mixture is taken from the final bioreactor and recycled back to the first bioreactor in the system.

In some embodiments, the entirety of the aqueous mixture is recycled at least once to a bioreactor occurring earlier in the line of bioreactors. In other embodiments, only a portion of the aqueous mixture is recycled. Where the entirety of the aqueous mixture is recycled, the low-rank coal substrate will be given more time to be degraded by low-rank coal degrading microorganisms. The methods provided herein result in the enrichment of microorganisms capable of degrading the low-rank coal substrate. Thus, upon recirculating the aqueous mixture, the enriched population of low-rank coal-degrading microorganisms further degrade the low-rank coal substrate. Where only a portion of the aqueous mixture is recycled, the enriched population of low-rank coal-degrading microorganisms in that portion supports the degradation of low-rank coal substrate in fresh aqueous mixture introduced into the multistage bioreactor system. The recycling of under-processed low-rank coal substrate within the system promotes the overall efficiency of the system, while simultaneously inoculating fresh alkaline-treated low-rank coal substrate with an enriched microbial community that further enhances process conversion efficiency.

In certain embodiments, incubation of the aqueous mixture, whether occurring in a single bioreactor or in a multistage bioreactor system, occurs at ambient temperatures. In certain embodiments, incubation occurs at temperatures between about 15° C. and 50° C. In some embodiments, incubation occurs at temperatures between about 20° C. and 45° C. In some embodiments, incubation occurs at temperatures between about 20° C. and 30° C.

In certain embodiments, the aqueous mixture is incubated for a time sufficient to allow for low-rank coal-degrading microorganisms to at least partially degrade the low-rank coal substrate. Degradation of the low-rank coal substrate results in the release of aerobic digestion products such as, for example, humic organic acids from the low-rank coal's carbon matrix. In certain embodiments, the aqueous mixture is incubated for a total of about 1 hour to about 20 days. In some embodiments, the aqueous mixture is incubated for a total of about 3 days to about 14 days. In some embodiments, the aqueous mixture is incubated for a total of about 7 days. In some embodiments, the entirety of the aqueous mixture is incubated for the same period of time. In other embodiments, such as when only a portion of the aqueous mixture is recycled to an earlier bioreactor, portions of aqueous mixture introduced to the multistage bioreactor system at the same time will be incubated for varying amounts of time. In certain embodiments, portions of aqueous mixture are incubated for about 1 hour to about 20 days. In some embodiments, portions of aqueous mixture are incubated for about 3 days to about 14 days. In some embodiments, portions of aqueous mixture are incubated for about 7 days.

In certain embodiments, the aqueous mixture is incubated in a single bioreactor of the bioreactor system for about 1 hour to about 48 hours before the aqueous mixture or a portion of the aqueous mixture is transferred to the subsequent bioreactor in the bioreactor system. In certain embodiments, the incubation time is different in separate bioreactors of the bioreactor system.

In certain embodiments, incubation of the aqueous mixture, whether occurring in a single bioreactor or in a multistage bioreactor system, occurs at least partially under aerobic conditions. In some embodiments, a bioreactor is considered to be "aerobic" if it includes a dissolved oxygen concentration of about 2 ppm oxygen or greater.

Following incubation, a fraction of the aqueous mixture comprising aerobic digestion products is collected. In certain embodiments, the fraction is collected from any one of the bioreactors of a multistage bioreactor system. For example, in a four-bioreactor system, a fraction of the aqueous mixture can be collected from the first, second, third, or fourth bioreactor. In certain embodiments, the fraction is collected from the last bioreactor of the system. In the above example, the fraction would be collected from the fourth bioreactor. In certain embodiments where a single bioreactor is used, the fraction is similarly collected following sufficient incubation.

Figure 12:
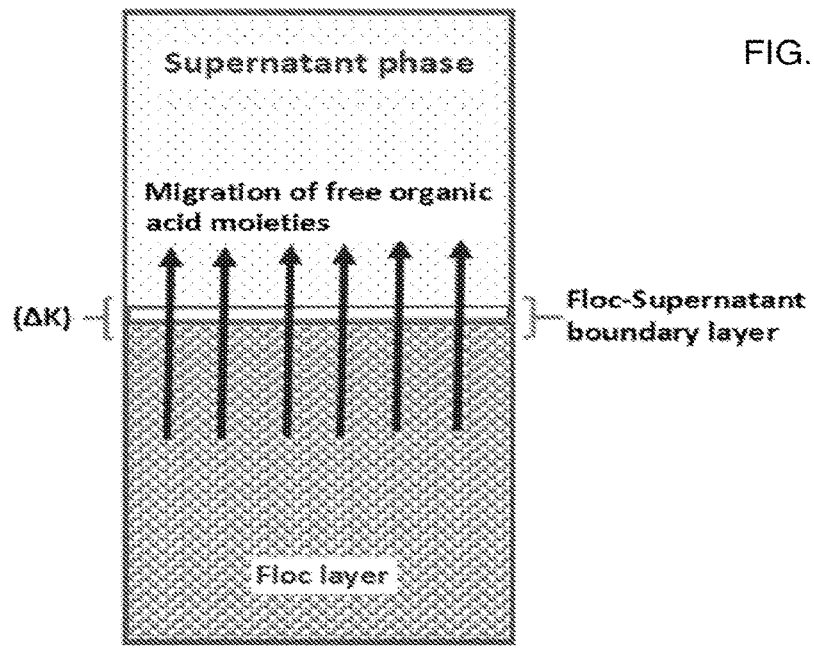
FIG. 12 is an illustration depicting the mass transfer of soluble and free organic acid moieties during phase separation from the bottom floc to the supernatant phase through the interface boundary layer (AK) driven by the concentration gradient of active organic acid molecules between the two phases.

In certain embodiments, a portion or the entirety of the aqueous mixture from a bioreactor is separated into a supernatant phase and a floc phase (see FIG. 12). The supernatant phase comprises at least a portion of the aerobic digestion products (e.g., humic organic acids) and is the collected fraction. Aerobic digestion products such as humic organic acids can thus be recovered from the collected supernatant phase. The floc phase comprises solids, including remaining low-rank coal substrate, and dense humic substances.

In some embodiments, low-rank coal-degrading microbes may be found dispersed throughout both the supernatant phase and the floc phase, and may be recovered from one or both of these phases. Similarly, in some embodiments, primary and secondary microbial metabolites may be found dispersed throughout both the supernatant phase and the floc phase, and may be recovered from one or both of these phases.

Figure 2A:
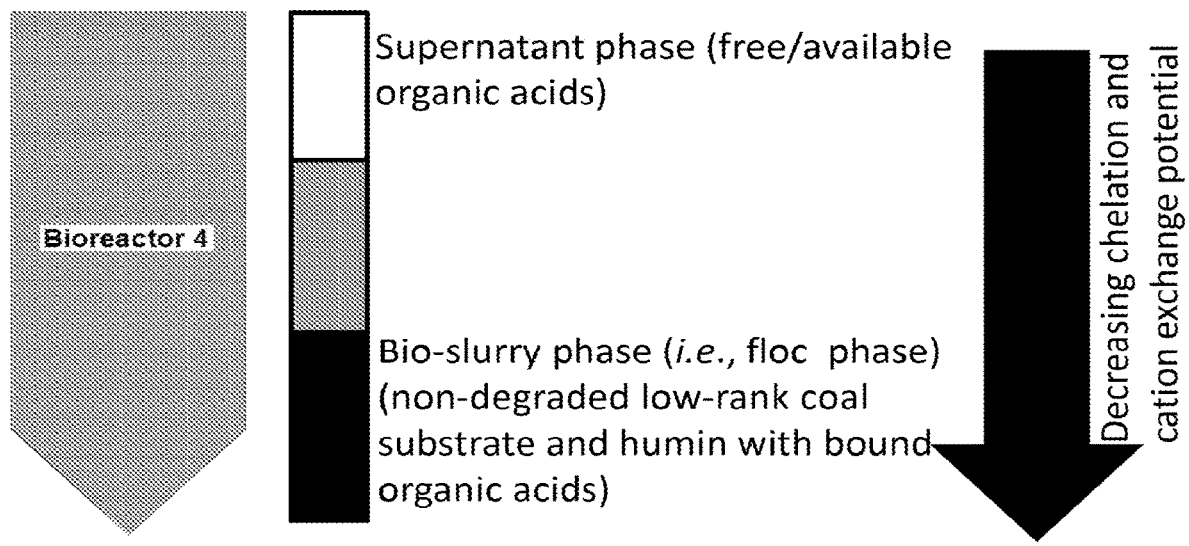
FIG. 2A is a diagram illustrating the contents in a final reactor of the system depicted in FIG. 1.
Figure 2B:
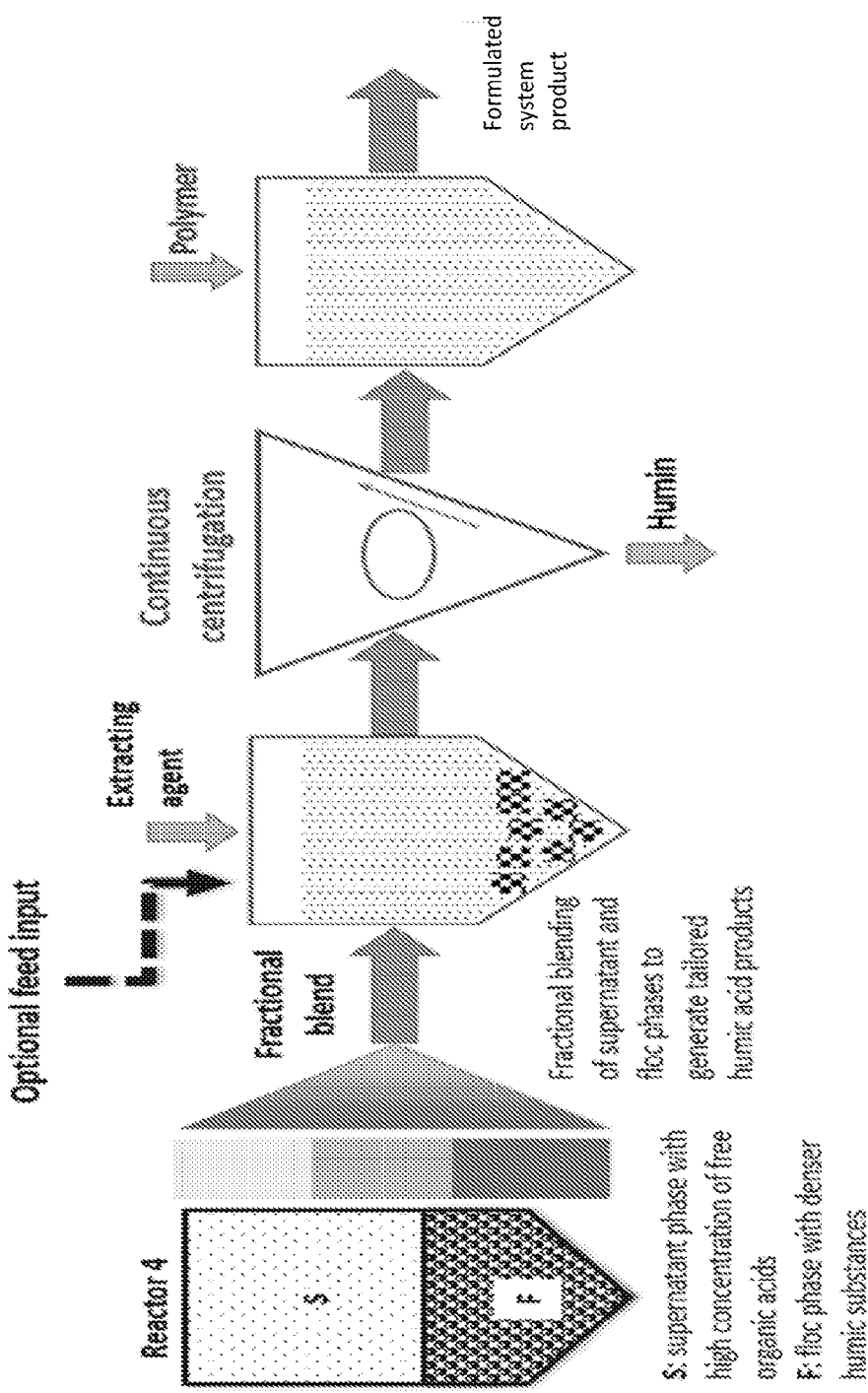
FIG. 2B illustrates downstream processing of products produced by the methods and processes described herein, according to one embodiment of the present disclosure.

In certain embodiments, through the process of enrichment of low-rank coal-degrading microbial communities and breakdown of low-rank coal substrate, the microbial communities tend to form aggregates of the substrate, or 'floc'. Floc formation is catalyzed by adhesive extracellular polymeric substrates from the microorganisms that act as flocculants to precipitate the low-rank coal substrate and/or humic particles. The process of biological release of aerobic digestion products exploits the relative solubility of different organic moieties existing in the low-rank coal substrate or humin to facilitate the transport of highly soluble organic acid moieties to the surrounding aqueous phase. The floc, upon reaching the last bioreactor of the multistage bioreactor system, sinks due to lack of recirculation and greater density, and collects at the bottom of the bioreactor (also termed a 'settling tank'). The supernatant phase is the solution or phase with few or no suspended solids, which is located above the floc phase (FIGS. 2A and 2B). In certain embodiments, the collected floc is recycled back into a previous bioreactor. In certain embodiments, the supernatant is continuously transferred to an accumulation tank.

Unused floc can be repurposed for use as, for example, a fertilizer coating.

In certain embodiments, aerobic digestion products such as free organic acids are contained in the supernatant phase of the last bioreactor in a series of bioreactors, or the last few bioreactors in a series of bioreactors.

In certain embodiments, a portion or the entirety of the aqueous mixture from a bioreactor is separated into a supernatant phase and a floc phase by a liquid-solid separation process. Such processes include, but are not limited to, gravity separation, centrifugation, and filter separation. FIG. 12 depicts mass transfer of soluble and free organic acid moieties during gravity phase separation from the bottom floc to the supernatant phase through the interface boundary layer (ΔK) driven by the concentration gradient of active organic acid molecules between the two phases. In certain embodiments, the aqueous mixture is transferred to a settling tank, and separation of the supernatant and floc phases occurs via gravity separation. In some embodiments, the settling tank is not aerated or is not substantially aerated. This can allow for the enriched microbial communities to go into a dormant state, where sporulation may occur.

In certain embodiments, following separation into supernatant and floc phases, the supernatant is concentrated (i.e., dewatered). Methods for concentrating the supernatant phase include, but are not limited to, evaporation, thin film evaporation, electro-coagulation, magnetic separation, and nanofiltration. In certain embodiments, the resulting concentrated supernatant phase comprises the humic organic acids. In certain embodiments, the supernatant phase is not concentrated. The resulting aerobic digestion products (e.g., humic organic acids) are recovered as a concentrated or non-concentrated supernatant. In certain embodiments, the supernatant phase can be further processed (e.g., fractionation by molecular weight), and the aerobic digestion products isolated.

In addition to aerobic digestion products, the supernatant phase also comprises microorganisms capable of degrading the low rank coal substrate. In certain embodiments, the supernatant phase is concentrated, but retains a population of microorganisms. In certain embodiments the supernatant phase is not concentrated. The collected supernatant phase, whether concentrated or not, therefore comprises aerobic digestion products and a population of microorganisms.

In certain embodiments, the floc phase can be reincorporated into a bioreactor of a multistage bioreactor system, or the bioreactor of a single bioreactor system. In certain embodiments, the floc phase, in addition to un- or partially degraded low-rank coal substrate and dense humic substances, further comprises low-rank coal-degrading microorganisms. Thus, similarly to those embodiments wherein the aqueous mixture or a portion thereof is recycled back into the incubation, recirculating the floc back into the incubation will result in the remaining low-rank coal substrate and dense humic substances having additional time to be broken down and will provide the system with a population of microorganisms capable of degrading the low-rank coal substrate.

In certain embodiments, properties of humic organic acids are monitored at one or more times throughout the incubation. In certain embodiments, one or more of the chelation capacity, zeta ($\zeta$) potential, and E4/E6 ratio of the humic organic acids is determined. The E4/E6 ratio is a measure of relative levels of aromaticity of a solution (see Grasset and Ambles, "Structure of humin and humic acid from an acid soil as revealed by phase transfer catalyzed hydrolysis" Organic Geochemistry, vol 29, no. 4, pp. 881-891, 1998). In certain embodiments, when humic organic acids attain a preselected value for one or more of the determined properties, the humic organic acids are recovered. In certain embodiments, the incubation step is continued until a preselected value for one or more of chelation capacity, zeta potential, and E4/E6 ratio is attained by the resulting humic organic acids.

In certain embodiments, the incubation step is continued until a preselected chelation capacity of the humic organic acids is achieved. The chelation capacity indicates the number of relevant organic moieties with available active sites capable of participating in chelation. Chelation capacity is determined per unit quantity of organic acid. In certain embodiments, chelation capacity is determined as described in Example 2. A higher chelation capacity is indicative of more active sites capable of participating in chelation. The number of active sites capable of participating in chelation increases with process/incubation times and/or number of bioreactors. In certain embodiments, the incubation period is continued until a desired and predetermined chelation capacity is achieved.

While the number of active sites capable of participating in chelation generally increases with process/incubation times and/or number of bioreactors, left for too long, low rank coal-degrading microbes of the systems and methods described herein may break down the organic acids into smaller molecular weight acids having a lower chelation capacity. As the organic acids are released from the carbon matrix of the low rank coal, the number of active sites increases as more polycyclic aromatic hydrocarbons are biodegraded and converted to catechols, salicylic acid, phthalic acid, etc. However, should these biodegradation products enter the tricarboxylic acid (TCA) cycle, at least some active sites may be lost. Thus, in certain embodiments, the organic acids are recovered before entering the TCA cycle. In some embodiments, the composition of the organic acids being produced is monitored by determining the E4/E6 ratio of the organic acids. Once the desired E4/E6 ratio is attained, the organic acids are collected.

In certain embodiments, the incubation period is continued until a preselected zeta potential of the humic organic acids is achieved. The zeta potential indicates the number of available sites for electrostatic chelation of metal ions, and the stability of the humic organic acids as a colloidal material. Zeta potential is a measure of the electrokinetic potential in dispersed colloidal suspensions based on the electrical potential existing between the double layer interfaces of a particle relative to the bulk medium and is measured in millivolts (mV). The electrokinetic potential of a colloidal system is a unique property, which can be used to evaluate the stability of the suspension. Colloidal suspensions with high electronegative or electropositive zeta potentials are more stable, while low zeta potentials (low electronegativity or electropositivity, i.e., closer to zero) result in agglomeration of dispersed particles due to reduced interparticulate electrostatic repulsion. It is expected that for a given low-rank coal substrate undergoing a controlled biodegradation process, an increase in the zeta potential (i.e., increased electronegativity) of the soluble phase represents an increase in free organic acid content. In certain embodiments, the number of sites available for chelation of metal ions increases with process times and/or number of bioreactors. In certain embodiments, the incubation period is continued until a zeta potential more negative than −10 mV, more negative than −20 mV, more negative than −30 mV, more negative than −40 mV, more negative than −50 mV, or more negative than −60 mV is achieved.

In certain embodiments, the incubation period is continued until a preselected E4/E6 ratio of the humic organic acids is achieved. The degree of degradation of high molecular weight humic substances is a direct function of process time and/or number of reactors and can be monitored using E4/E6 ratio analysis. Higher E4/E6 ratios, indicative of low molecular weight humic organic acids, can be achieved through extended sequential biodegradation, as provided by the methods described herein. For example, the first reactor may have a E4/E6 of 2.197 while the last reactor may have a ratio of 4.988, indicating that aromaticity is decreasing from the first reactor to the last reactor. In certain embodiments, the incubation period is continued until an E4/E6 ratio of about 3 to about 30, about 5 to about 30, about 10 to about 30, about 15 to about 30, or about 20 to about 30 is achieved.

In certain embodiments, parameters such as incubation time, temperature, and microorganism concentration can be varied to generate different aerobic digestion products, such as humic organic acids, across the entire incubation, or even in different bioreactors. That is, parameters for each bioreactor of a multistage bioreactor system can be manipulated to generate different aerobic digestions products (e.g., different humic organic acids).

In certain embodiments, at least one of the chelation capacity, the zeta potential, and the E4/E6 ratio is determined at multiple time points in order to establish an incubation time necessary to achieve an organic acid output having a desired property (i.e., chelation capacity, zeta potential, E4/E6 ratio, or combination thereof). In certain embodiments, at least one of the chelation capacity, the zeta potential, and the E4/E6 ratio is monitored at one or more intermediate time points during the incubation period. In some embodiments, at least one of the chelation capacity, the zeta potential, and the E4/E6 ratio is determined at an intermediate time point during the incubation period, and when the desired organic acid properties are achieved, a volume of the aqueous mixture is collected and the organic acids therein are recovered. In such embodiments, the remaining aqueous mixture continues through the incubation step until an additional intermediate collection is taken, or until the final preselected values for at least one of the chelation capacity, the zeta potential, and the E4/E6 ratio is achieved. This allows for the collection and recovery of organic acids having different properties from the same multistage bioreactor system. In some embodiments, no intermediate collection and recovery occurs, and all the aqueous mixture is incubated for the same period of time.

In other embodiments, low-rank coal derivative production and/or primary or secondary microbial metabolite production is monitored at one or more intermediate timepoints during the incubation period. When the desired low-rank coal derivative and/or primary or secondary microbial metabolite is detected, or achieves a desired concentration, a volume of the aqueous mixture is collected and the low-rank coal derivative(s) and/or primary or secondary microbial metabolites therein are recovered. In such embodiments, the remaining aqueous mixture continues through the incubation step until an additional intermediate collection is taken, or until the incubation is complete. This allows for the collection and recovery of different aerobic digestion products with various biochemical characteristics from the same multistage bioreactor system. In some embodiments, no intermediate collection and recovery occurs, and all the aqueous mixture is incubated for the same period of time.

In certain embodiments, the methods and processes are continuous. That is, as aqueous mixture is moved from one bioreactor to the next, new aqueous mixture is introduced into the multistage bioreactor system, resulting in a continuous process. In those embodiments where portions of the aqueous mixture and/or floc phase are recycled within the system, the amount of new aqueous mixture added to the system can be appropriately adjusted. In some embodiments, the quantitative rate of new feedstock (i.e., low-rank coal substrate and water, or aqueous solution) addition into a first bioreactor is the same or similar to the rate of movement of solution from the first bioreactor to the second bioreactor, and each subsequent bioreactor.

Low-Rank Coal-Degrading Microorganisms

In the methods and processes described herein, microorganisms capable of degrading low-rank coal cause the release of humic organic acids and other aerobic digestion products from the low-rank coal substrate. In certain embodiments, the microorganisms capable of degrading the low-rank coal substrate naturally reside in or on the low-rank coal substrate, or in or on the phosphorous source (e.g., rock phosphate). In certain embodiments, the addition of yeast is useful in the methods described herein to aid the growth of low-rank coal-degrading microorganisms.

Microorganisms capable of degrading low-rank coal are defined as those capable of growing on alkalinized leonardite media (ALM). ALM includes leonardite pre-treated with a dilute solution of KOH (e.g., about 1.0 g/ml to about 10.0 g/ml leonardite treated with 0.03M KOH). In some embodiments, the microbial nutrient media includes pre-treated leonardite (15% v/v), M9 salts (10% v/v of a 5× stock, Sigma M6030), a trace mineral solution (0.1% v/v of solution (in 1 L): $MgSO_4$ 0.25 g, KCl 0.25 g, $KH_2PO_4$ 0.5 g, Fe$_2$(SO$_4$)$_3$·6H$_2$O 0.15 mg, MnSO$_4$×H$_2$O 5.0 mg, CuSO$_4$·5H$_2$O 0.16 mg), CaSO$_4$ (0.01%) and Noble agar (18% w/v, Sigma A5431).

In certain embodiments, the low-rank coal substrate and/or phosphorous source is a source of one or more of *Shinella* spp., *Sphingomonas* spp., *Camelimonas* spp., *Sphingopyxis* spp., *Acinetobacter* spp., *Microbacterium* spp., *Methylocystis* spp., and *Pseudorhodoplanes* spp.

In some embodiments, the enriched low-rank coal-degrading microbial communities produced by the systems and methods described herein are collected. Such a microbial composition can be used, for example, as the microbial stock solution described below, and can be introduced back into the system to increase or improve aerobic digestion of the low-rank coal substrate. In other embodiments, the collected low-rank coal-degrading microbes can form their own product; that is, they can be packaged for use separately from the system from which they were collected. The low-rank coal-degrading microbes can be used, for example: in a separate low-rank coal degrading system as an exogenous microbial stock solution to provide additional low-rank coal-degrading microbes to the system; as a fertilizer additive, where the fertilizer includes a low-rank coal particulate fraction and/or a humic acid fraction; or as a separate product to be applied in conjunction with a fertilizer that includes a low-rank coal particulate fraction and/or a humic acid fraction.

In certain embodiments, the methods and processes described herein further comprise incorporating a microbial stock solution to the aqueous mixture. In some embodiments, the microbial stock solution comprises low-rank coal-degrading microorganisms. In some embodiments, the microbial stock solution consists solely of low-rank coal-degrading microorganisms. Supplementing the aqueous mixture of low-rank coal substrate, a phosphorous source, and yeast with an exogenous microbial stock solution can enhance the degradation of the low-rank coal substrate in the presently described process systems and can improve the yield and physicochemical properties of the resulting humic organic acids.

In certain embodiments, an exogenous microbial stock solution comprises one or more of *Shinella* spp., *Sphingomonas* spp., *Camelimonas* spp., *Sphingopyxis* spp., *Acinetobacter* spp, *Microbacterium* spp., *Methylocystis* spp., and *Pseudorhodoplanes* spp.

In certain embodiments, the phosphorous source (e.g., rock phosphate) and yeast act as nutrient sources for the low-rank coal-degrading microorganisms, regardless of whether the microorganisms are innate to the low-rank coal substrate and/or phosphorous source or are supplied via an exogenous microbial stock solution.

See Example 6 for further description of the low-rank coal-degrading microorganisms.

Aerobic Digestion Products Produced by the Methods and Processes Described Herein In an aspect of the present disclosure, provided herein are aerobic digestion products produced by the methods and processes described herein, including organic acids, low-rank coal derivatives, and primary and secondary microbial metabolites.

The methods and processes described herein result in the production of organic acids including, but not limited to, humic acids, ulmic acids, fulvic acids, and combinations thereof. The methods and processes described herein allows for monitoring and controlling the degree of degradation of the low-rank coal substrate, and thus control, for example, the relative amounts of organic acids produced, the molecular weight of the organic acids produced, and the physicochemical properties of the organic acids produced.

In certain embodiments, the recovered organic acids can be further purified, separated according to molecular weight, or otherwise further processed. In certain embodiments, the recovered organic acids are fractionated according to molecular weight via a membrane separation process.

In certain embodiments, the recovered aerobic digestion products, including organic acids, can be incorporated or formulated into a product composition. Product compositions comprising the recovered organic acids can be used, for example, to (1) reduce escape of beneficial cations from a soil environment through the formation of insoluble complexes with soil anions; (2) formulate complex fertilizers with reduced precipitation of 'fall out' through effective chelation and cation exchange; (3) introduce specialty metal ions to a soil environment for plant uptake (e.g., zinc and iron ions); (4) functioning as a vehicle to deliver a variety of high payload micronutrients to the soil for plant uptake; (5) enhancing plant resistance to salt stress through direct chelation of metal ions and redistribution across the soil bed; and (6) remediating soils with heavy metal contamination.

In certain embodiments, a product composition comprises organic acids recovered at different phases or time points of the described methods and processes. Resulting product compositions will comprise a variety of distinct organic acids, having different molecular weights and chelation potentials. Because of the ability to selectively produce and recover organic acids having certain desired physicochemical properties, the methods and processes described herein provide a unique opportunity to generate different organic acid profiles and to establish tailored product characteristics.

In certain embodiments, the organic acids produced by the methods and processes described herein demonstrate a high cation exchange capacity ("CEC"), which is indicative of the free active sites on the organic acids that are available to chelate metal ions. The CEC refers to the amount of negative charges available on the surface of soil particles, so it also indicates the potential of the soil to hold plant nutrients. In other words, as the soil CEC increases, the amount of a soil-applied fertilizer needed to provide optimal amounts of cations for plant nutrition is reduced. Examples of cations in the agricultural soils include but are not limited to K$^+$, Ca$^{2+}$, Mg$^{2+}$, Na$^+$, Al$^{3+}$, H$^+$, NH4$^+$, Fe$^{2+}$, Mn$^{2+}$, and Cu$^{2+}$. Cations can either be bound to the soil surfaces or exist in the soil solution. The exchangeable cations, which are bound to the soil surfaces, are in equilibrium with a soil solution that contains only a small portion of plant nutrients. The CEC, therefore, provides a reservoir of nutrients to replenish those removed by plant uptake or leached out of the root zone.

The CEC is, in some embodiments, influenced by pH or the type of metal ion in the environment or soil, particularly for CEC in organic matters. In some embodiments, the pH (i.e., decreasing the concentration of H$^+$ cations) increases this variable charge, and therefore also increases the cation exchange capacity.

In certain embodiments, the organic acids produced by the methods and processes described herein are free organic acids. In some embodiments, the organic acids comprise humic acid and fulvic acid. In some embodiments, the CEC for the organic acids ranges from 0.1 meq/g to about 100 meq/g, 0.5 meq/g to about 50 meq/g, 1 meq/g to about 31 meq/g, or 5 meq/g to about 31 meq/g. In some embodiments, the CEC is at least 5 meq/g. In some embodiments, the CEC ranges from 5 meq/g to about 31 meq/g. See Example 4.

Aqueous Composites Produced by the Methods and Processes Described Herein

In an aspect of the present disclosure, provided herein are aqueous composites produced by the methods and processes describe herein, wherein the aqueous composites comprise low-rank coal-degrading microbial communities, organic acids, low-rank coal derivatives, primary and secondary microbial metabolites, or a combination thereof.

The methods and processes provided herein provides the ability to tailor product compound characteristics to support various technologies relating to the development of high-concentration free organic acid-based (e.g., humic and fulvic acids) products with sustained homogeneity and integrity. In certain embodiments, such products are fertilizer formulations.

A major challenge associated with conventional humic acid products in fertilizer formulations is high solid content (i.e., humin particulate) which 'falls out' from formulation, creating significant handling issues, including application issues by the grower. The present methods and processes address these issues by continuously concentrating and separating the humin particles.

In certain embodiments, the aqueous composites can be incorporated or formulated into a product composition. Product compositions comprising the aqueous composites can be used similarly to those product compositions comprising the recovered organic acids. In some embodiments, product compositions comprising an aqueous composite may further benefit from effects resulting from the presence of the microbial communities and/or the primary and secondary microbial metabolites.

In certain embodiments, the floc phase comprises humic particles and bound organic acids having desirous properties. In certain embodiments, floc phase is incorporated into product compositions comprising aerobic digestion products from the supernatant phase and/or the enriched microorganisms. In some embodiments, the presence of the floc increases the humic acid content of the product composition without the need to add low-rank coal (e.g., leonardite) to the composition.

As depicted in FIG. 2B, downstream processing can produce various custom product technologies comprising the organic acids produced by the methods and processes described herein and the resulting floc can be created with optional addition of feed and extracting agent(s) to concentrate the amount of organic acids without compromising the physical characteristics of the humic acid product in various agrochemical formulations. In certain embodiments, the present methods and processes makes use of a centrifugation process that continuously removes humin particles from the process to deliver a uniform product that is further stabilized with a biopolymer to enhance homogeneity. At least 90% of humin particles can be removed to generate homogenous organic acid products with specific characteristics (e.g., chelation capacity, zeta potential, E4/E6 ratio) without compromising the functionality of the product.

FIG. 2B depicts downstream processing of the products produced by the methods and processes described herein to generate various humic product technologies with tailored characteristics and applications.

In certain embodiments, a product composition comprises about 0.5-30% humic organic acids, and negligible humin content. In some embodiments, the product composition comprises about 0.5-2% humic organic acids. In some embodiments the product composition comprises about 10-25% humic organic acids. In some embodiments, the product composition further comprises chemically extracted leonardite. The chemically extracted leonardite further contributes to the humic organic acid content of the product composition. In some embodiments, the humic acid-enriched supernatant is centrifuged to remove residual humins. In some embodiments, the product composition further comprises low-rank coal (e.g., leonardite) and/or floc from the floc phase. In some embodiments, polymers, such as polyacrylic acid (PAA) can be added to increase the suspension of the high molecular weight organic acids.

In some embodiments, an aerobic digestion product described herein is used as an added ingredient in a fertilizer formulation. The aerobic digestion products can, for example, be added to a fertilizer formulation to provide or enhance salt tolerance-inducing characteristics of the formulation, provide or enhance nutrient uptake-inducing characteristics of the formulation, improve plant response to stress condition, improve cation exchange capacity and/or chelation capacity, and/or enhance microbial interactions at the rhizosphere. That is, aerobic digestion products described herein may be included in formulations to provide or enhance the properties of the formulation, providing or enhancing those properties or characteristics that the aerobic digestion products are described herein to possess.

Systems for Continuous Enrichment of Low-Rank Coal-Degrading Microbial Communities and Simultaneous Biological Release of Aerobic Digestion Products In an aspect of the present disclosure, provided herein are systems for continuous enrichment of low-rank coal-degrading microbial communities and simultaneous biological release of aerobic digestion products. The systems are designed to operate continuously, and generate aerobic digestion products (e.g., organic acids, microbial metabolites) at a constant rate.

In certain embodiments, the system is a multistage bioreactor system. In certain embodiments, the multistage bioreactor system includes two or more interconnected bioreactors. In some embodiments, the multistage bioreactor system comprises 2-20 bioreactors. In certain embodiments, the multistage bioreactor system comprises at least 4 bioreactors. In addition to bioreactors, in certain embodiments, a multistage bioreactor system may include one or more pretreatment tanks, one or more settling tanks, one or more collection tanks, or any combination of at least two of these types of tanks.

In certain embodiments, the bioreactors of the multistage bioreactor systems are fluidized bed reactors, plug flow fluidized bed reactors, or a combination of these types of reactors.

Fluidization in the fluidized bed reactors can be achieved by different means, e.g., pumps, stirrers, or gassing the substrate. When air is used to fluidize the carriers, the air is pumped into the bioreactors by any effective means, e.g., from the bottom of the bioreactor. To avoid sudden increase of pressure resulting from the introduced gas, the reactor, in one embodiment, comprises an outlet to release the gaseous effluents from the bioreactor or the system.

In plug flow fluidized bed reactors, plug flow of the aqueous mixture (i.e., working solution) is achieved via hydraulic displacement of the aqueous mixture using controlled volumetric addition of new aqueous mixture into the first bioreactor of a multistage bioreactor system, resulting in an equal amount of output from the bioreactor.

In certain embodiments, one or more bioreactors of the multistage bioreactor system comprise a scaffold. In some embodiments, the scaffold provides a surface for the formation of a biofilm. Biofilms can promote better biophysical interactions with the working solution (i.e., aqueous mixture). In some embodiments, the scaffold is a permeable body, such as a matrix, a permeable body, a packed bed of growth bodies, or a combination thereof. The scaffold provides a three-dimensional support structure for biofilm formation.

In certain embodiments, the multistage bioreactor system comprises a recycle loop. In some embodiments, the recycle loop allows for recycling of a portion or all of the aqueous mixture from a bioreactor to another bioreactor of the system, and or a portion or all of the floc phase from a bioreactor or, for example, a settling tank, to another bioreactor of the system.

In certain embodiments, each bioreactor of the multistage bioreactor system comprises a recirculation loop, which provides for recirculation of aqueous mixture within the bioreactor.

In certain embodiments, the multistage bioreactor system comprises one or more pumps. The pumps function to circulate the system contents throughout the various components of the system, as well as within individual bioreactors.

In some embodiments, the pump is a fluidization pump that is attached to the bottom portion of a bioreactor to increase suspension of particles in the bioreactor. In some embodiments, the pump means can be a chemical feed pump, a microbial feed pump, or a recirculating pump that promotes the recirculation in the same reactor or between different bioreactors through the recirculation loop, or a recycle pump. In some embodiments, the multi stage bioreactor system's recirculation pumps will be equipped with venturi suction aeration to increase dissolved oxygen content in the working solution. In some embodiments, for the recirculation within the same reactor, a recirculation pump has an inlet attached to the bottom portion of a reactor and an outlet attached to the top portion of the reactor. In another embodiment, the recycle pump has an inlet connected from one reactor and an outlet connected from another reactor. The two reactors can be connected with a recycle loop.

In certain embodiments, working solution is circulated or recycled among the bioreactors via a pump means, via gravity, or a combination of pumps and gravity.

In certain embodiments, the bioreactors are connected via a transfer line, a recycling loop, or by other means. In some embodiments, the final reactor is not connected to the recycling loop, and thus functions as a settling tank.

In certain embodiments, each bioreactor can have a size between 0.1 gallons and 10,000 gallons. In some embodiments, the size of a bioreactor is selected from 0.1 gallon, 0.5 gallon, 1 gallon, 2 gallons, 3 gallons, 5 gallons, 6 gallons, 7 gallons, 8 gallons, 9 gallons, 10 gallons, 11 gallons, 12 gallons, 13 gallons, 15 gallons, 20 gallons, 25 gallons, 30 gallons, 35 gallons, 40 gallons, 45 gallons, 50 gallons, 100 gallons, 1000 gallons and 10,000 gallons. The dimensions of the bioreactors can be scaled-up with constant aspect ratios and mass transfer conditions in order to increase the hydraulic loading.

In certain embodiments, the multistage bioreactor system comprises an accumulation tank. Once the supernatant in one of the bioreactors is separated from the floc, the supernatant phase comprising the produced organic acids can be transferred to the accumulation tank for temporary storage and/or further stabilization.

An example of a multistage bioreactor system is depicted in FIG. 1. FIG. 1 depicts a multistage bioreactor system having a pretreatment tank (PT), four bioreactors (R1, R2, R3, and R4), and an accumulation tank (AT). Low-rank coal substrate is pretreated as described herein in the pretreatment tank. The aqueous solution comprising the low-rank coal substrate (i.e., feedstock) is the transferred to the first bioreactor (R1). In R1, rock phosphate and yeast can be added to produce the aqueous mixture, if not already included in the aqueous solution. In some embodiments, only the rock phosphate is added in R1, and the yeast is added in the second bioreactor (R2). As new feedstock is transferred to R1, an equal volume of the aqueous mixture is transferred to R2, R3, and R4, resulting in plug flow. R1, R2, and R3 each include a recirculation loop to provide for recirculation of a bioreactor's contents within the bioreactor, a means for escape for gaseous effluents, and a venturi suction device, which functions to facilitate the movement of fluid within a bioreactor or between the bioreactors. R4 lacks the recirculation loop, means for escape for gaseous effluents, and venture suction device. As illustrated, R2 and R3 are aerated, while R4 is not aerated or is at least not substantially aerated. This results in R4 functioning as a settling tank, where the floc phase comprising non-degraded low-rank coal substrate and humic substances settles to the bottom, while the supernatant phase comprising the organic acids remains suspended above the floc phase as illustrated in FIGS. 2A and 2B. As depicted, R4 includes a recycle loop (RCL), which provides for the recycling of the floc phase or a portion of the floc phase to R1. It is to be recognized that any reactor could include a recycle loop capable of recycling bioreactor contents to a previous bioreactor. R4 also comprises a supernatant phase transfer means capable of transferring the supernatant phase to the accumulation tank (AT).

Methods for Improving Soil Quality

In one aspect, provided herein are method for promoting and/or improving soil quality, the methods comprising applying to a soil an effective amount of aerobic digestion products produced by the methods and processes described herein. As described herein, the aerobic digestion products produced by the method and processes described herein increase soil cation exchange capacity, increase nutrient bioavailability, and increase soil respiration, resulting in an improvement in overall soil quality and/or health. In certain instances, the improved soil quality resulting from application of the aerobic digestion products produced by the present methods results in improve plant germination and/or growth.

In certain embodiments, aerobic digestion products produced by the methods and processes described herein are applied to the soil where a plant grows or will grow. It is contemplated that when an aerobic digestion product produced by the methods and processes described herein is applied to the plant, it can be applied, for example, in-furrow, by drip, by flood irrigation, during overhead irrigation, sidedress injection into the soil (e.g., with nitrogen), in the vicinity of the roots of the plant, to the rooting zone, and/or to an area proximate to where a plant is to be grown.

In certain embodiments, at least 0.01 parts of aerobic digestion products per million parts of the composition (e.g., fertilizer) is applied. The term "ppm," as used herein, refers to parts by weight of the aerobic digestion products per one million parts by weight of the composition or a fertilizer. In some embodiments, the amount of organic digestion products in the composition is from about 0.01 ppm to about 50,000 ppm, about 0.1 ppm to about 10,000 ppm, about 1 ppm to about 5,000 ppm, about 10 ppm to about 2,500 ppm, about 100 ppm to about 2,000 ppm, or about 500 ppm to about 1,500 ppm. In some embodiments, the amount of aerobic digestion products is from about 1 ppm to about 5,000 ppm, about 10 ppm to about 2,500 ppm, or about 100 ppm to about 2,000 ppm of the composition. In some embodiments, the amount of aerobic digestion products in the composition is at least 0.001 ppm, 0.01 ppm, 0.1 ppm, 1 ppm, 10 ppm, 100 ppm, 1,000 ppm, 10,000 ppm, or 100,000 ppm.

In certain embodiments, about 0.5 quart to about 10 quarts of a product composition comprising aerobic digestion products is applied per acre in a single application. In some embodiments, about 1 quart to about 6 quarts of a product composition comprising aerobic digestion products is applied per acre in a single application. Multiple applications may be made throughout the year. In some embodiments, about 1 quart of a product composition comprising aerobic digestion products is applied for every 2-5 gallons of liquid fertilizer that is applied.

In certain embodiments, the aerobic digestion product composition or the product composition is mixed with or incorporated into a dry fertilizer. In these embodiments, about 0.5 quart to about 5 gallons of the aerobic digestion product composition is mixed per fertilizer ton. Suitable dry fertilizers include granular material and soil amendments. In certain embodiments, the aerobic digestion product can be blended with other biotechnologies.

In certain embodiments, the amount of aerobic digestion products (e.g., free humic acids and free fulvic acids; microbial metabolites) used in a composition may depend upon particular situations or factors, such as soil pH, temperature, soil type, etc., and on the mode of application. For example, dispensing aerobic digestion products (e.g., free humic acids and free fulvic acids; microbial metabolites) can be prolonged over a period of many months. In some embodiments, the amount of aerobic digestion products to be applied in a broadcast application is greater than in a row or band application, which permits a high concentration of the aerobic digestion products to be applied within close proximity to the plant. Applied near the root zone of growing plants, or immediately prior to seeding or transplanting, a lesser amount can be used than when the application is made at the end of the growing season to prepare the soil for the following season. In some embodiments, application is made at the end of the year to prepare the soil for the following season.

Methods for Improving Plant Growth

Figure 3A:
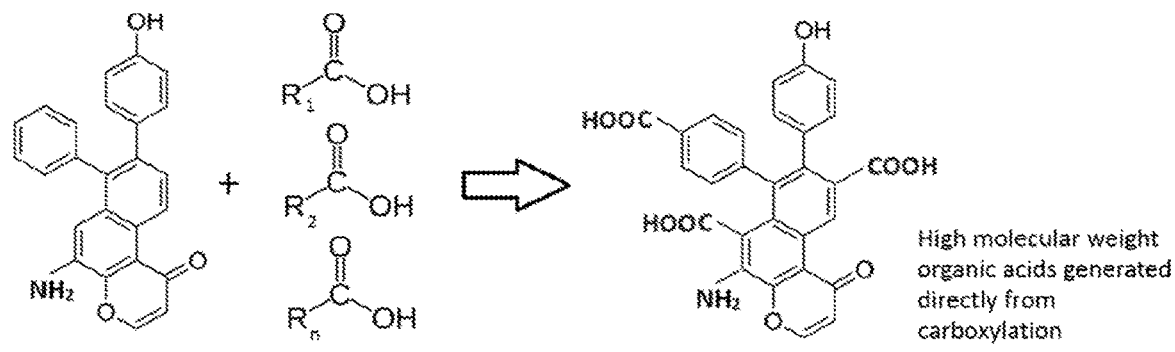
FIG. 3A is an illustration depicting the carboxylation of humin and the degradation of high molecular weight organic acids to low molecular weight organic acids.
Figure 3A:
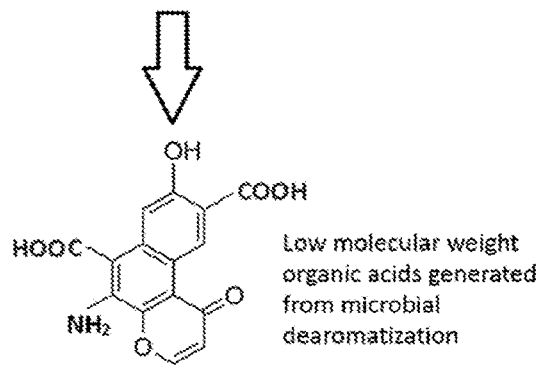
Figure 3B:
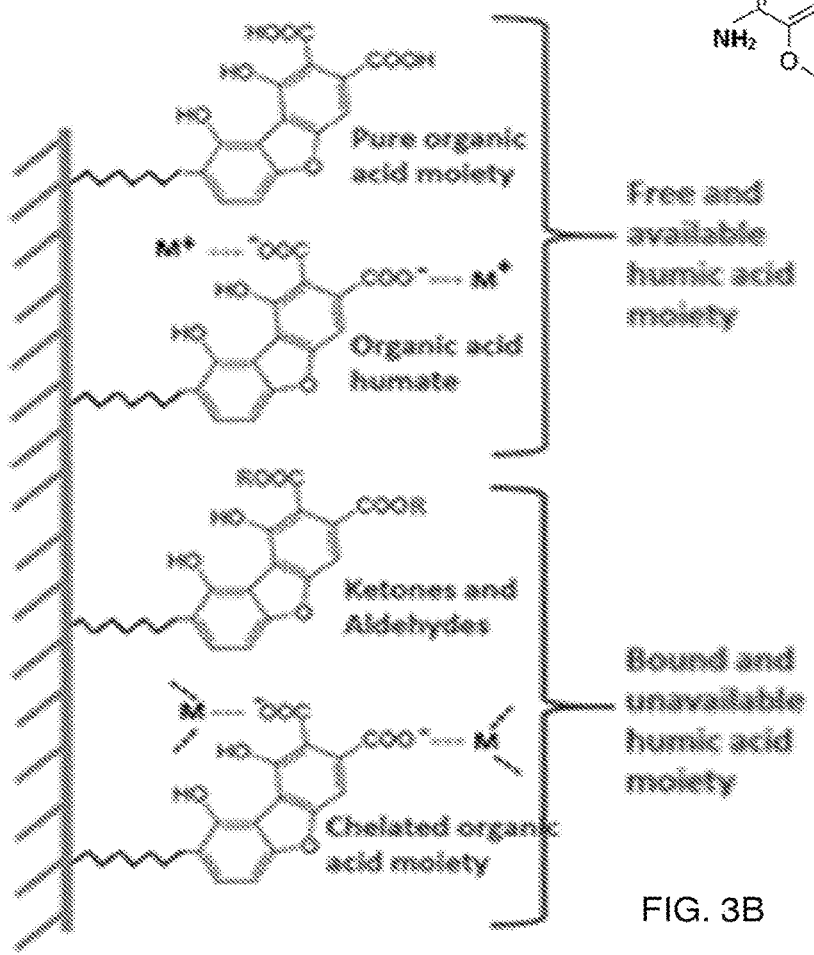
FIG. 3B is an illustration depicting differences between free and bound organic acid moieties.
Figure 3C:
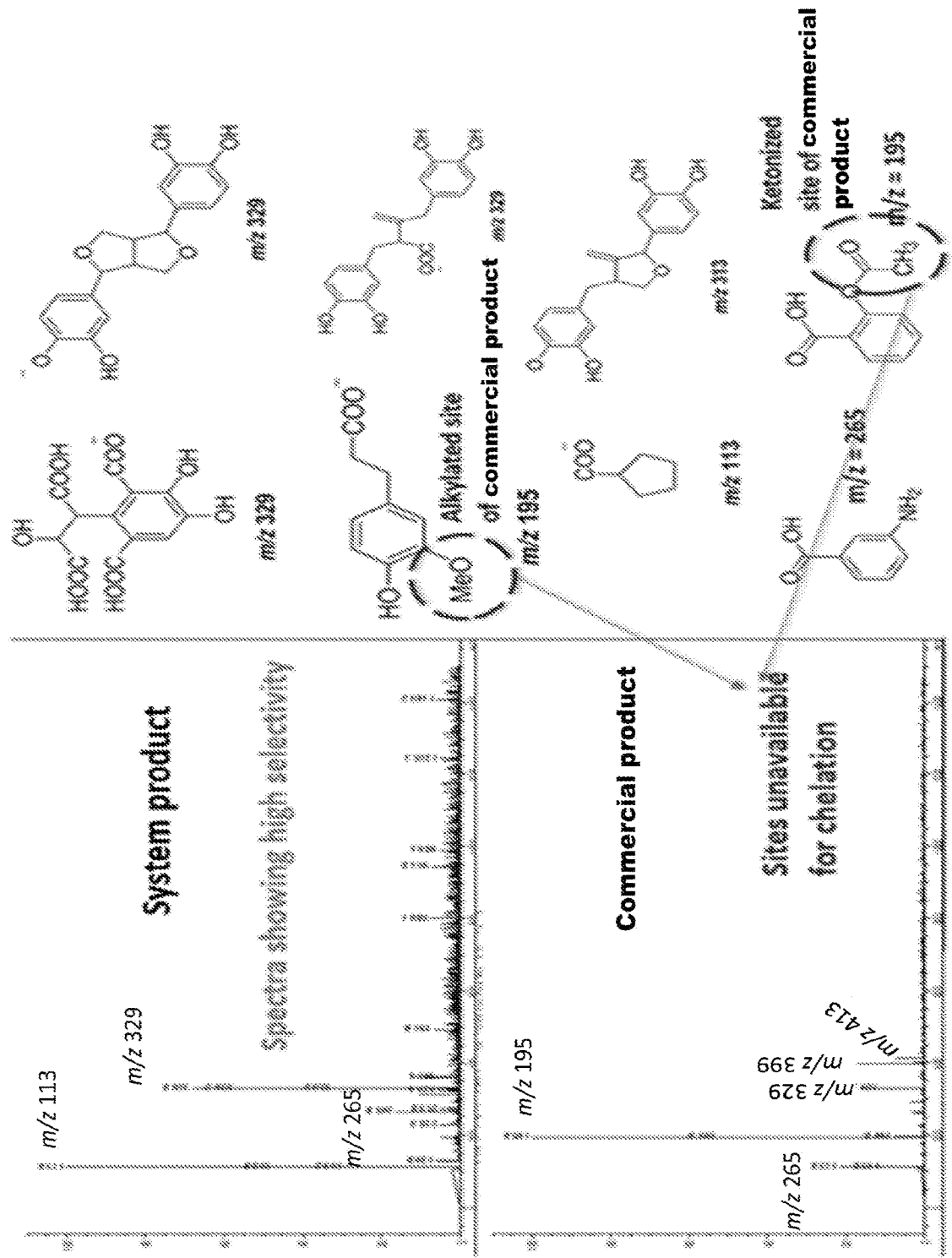
FIG. 3C presents mass spectrographs comparing the system product and a chemically extracted, commercially available humic acid product. Also provided are chemical structures of free, available organic acid moieties and bound, unavailable organic acid moieties.

Soils with high CEC generally have a higher water holding capacity and higher content of organic matter than soils with low CEC, depending on the chemistry and physical attributes of the soil matrix. In particular, soils with low CEC are likely to develop cation deficiencies. As provided herein, the methods and processes described herein release free and available organic acids from low-rank coal substrates by creating a biophysical environment that allows organic acids moieties with high aqueous solubility to diffuse from the solid matrix of the low-rank coal into the liquid phase. The products contain high concentrations of free and available organic acid products relative to total organic acids, which is one of many characteristics that uniquely differentiate the organic acids produced by methods and processes of the present disclosure and product compositions produced therefrom from other humic acid products. See, for example, FIGS. 3B and 3C, which illustrates the difference between bound, unavailable humic acid moieties and free, available humic acid moieties. FIG. 3C depicts mass spectrographs of the system product and a commercial product. The commercial product is the result of a chemical humic acid extraction. The main molecular fragments depicted by the spectrograph of the system product are those with mass/charge (m/z) ratios of 113, 265 and 329. Molecular assignment at these m/z ratios show moieties of humic acids with free organic acids sites available for metal ion binding. The commercial product on the other hand, showed m/z ratios at 113, 195, 329, 399 and 413. Molecular structures corresponding to m/z=195, which is the highest peak concentration identified on the commercial product spectrograph, show alkylated and ketonized sites which are unavailable for metal ion chelation. Both the system product and the commercial product showed peaks at m/z of 113 and 329. The system product demonstrated higher peak concentrations at both m/z ratios. Molecular assignments at both m/z 113 and 329 peaks show the presence of binding sites that are available for metal ion chelation. The mass spectrographs indicate that the system product contains a higher composition of free organic acids than the chemically extracted commercial product, demonstrating the selectivity of the biological extraction process for free organic acids generation.

Figure 10:
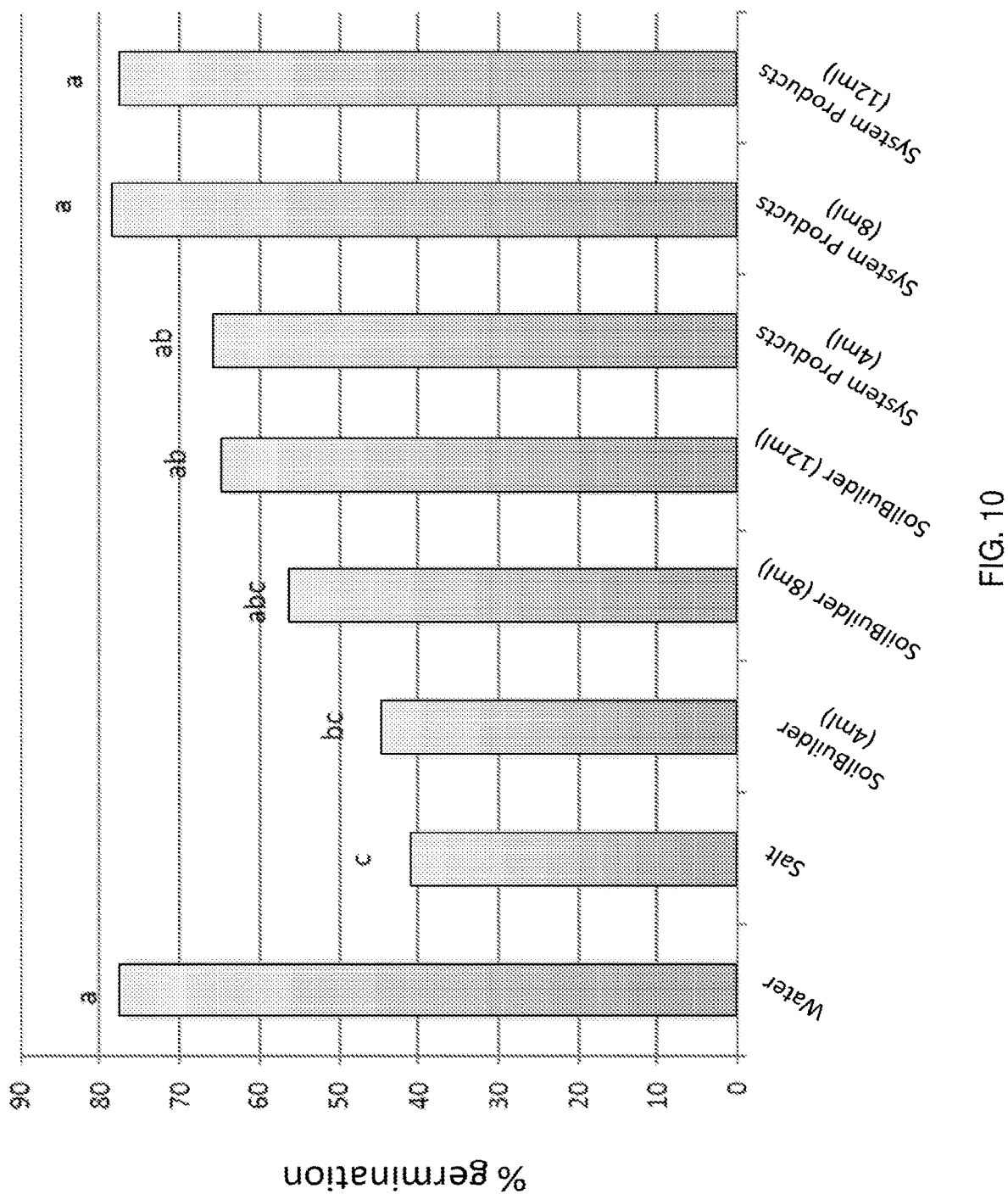
FIG. 10 is a bar graph illustrating the results of a wheat germination assay in the presence of salt.
Figure 11:
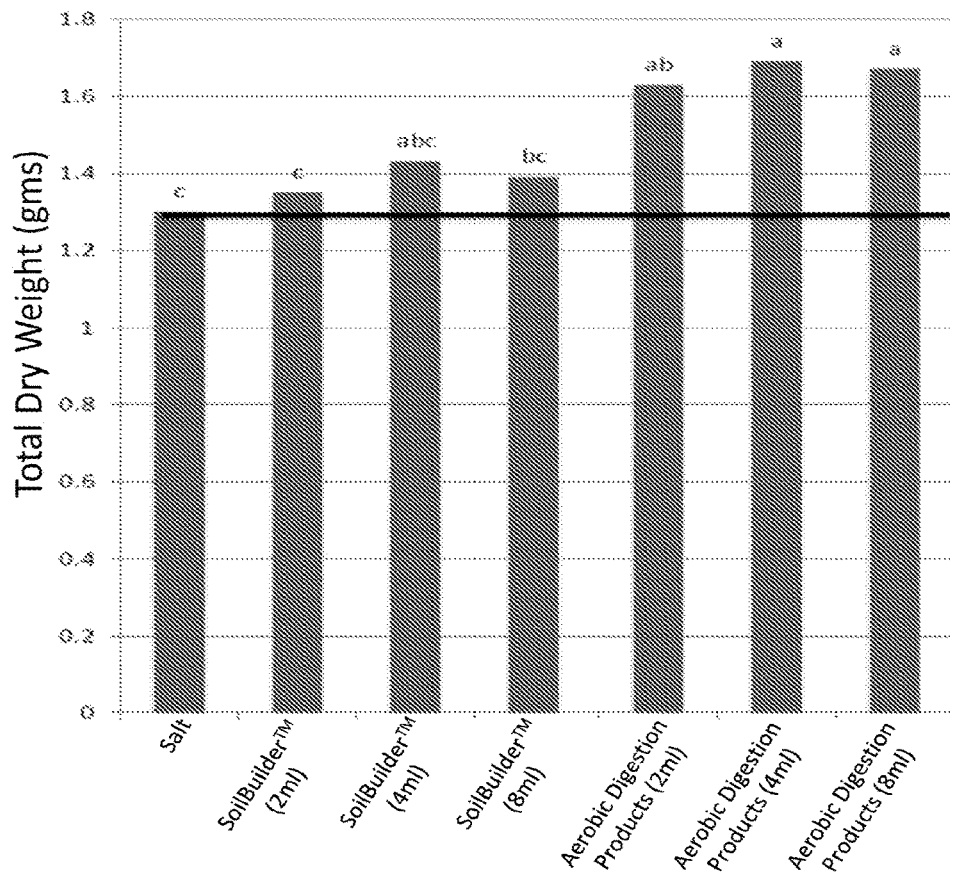
FIG. 11 is a bar graph illustrating the results of an assay of wheat grown in the presence of salt.

The availability of free and available organic acids is important to the superior chelation efficiency capacity, and chelation strength observed in the aerobic digestion products of the present disclosure relative to commercially available humic acid products, in addition to plant benefits such as salt stress alleviation (see FIGS. 10 and 11).

Given the high CEC per gram organic matter due to the availability of free organic acid moieties, system products produced by the methods and processes described herein can be used to promote the uptake of nutrients and promote plant growth when used in conjunction with a fertilizer, or when incorporated into a fertilizer. In certain embodiments, the system products produced by the methods and processes described herein can be used in conjunction with or incorporated into compound fertilizers, such as nitrogen-phosphorous-potassium (NPK) grill fertilizers.

In an aspect of the present disclosure, provided herein are methods for promoting plant growth, the methods comprising applying to the soil an effective amount of aerobic digestion products produced by the methods and processes described herein. In another aspect, the disclosure relates to a fertilizer comprising aerobic digestion products produced by the methods and processes described herein.

In certain embodiments, the aerobic digestion products produced by the methods and processes described herein comprise free organic acids. In some embodiments, the organic acids comprise humic acid and fulvic acid. In some embodiments, the soil CEC for the organic acids ranges from 0.1 meq/100 g to about 100 meq/100 g, 0.5 meq/100 g to about 50 meq/100 g, 1 meq/100 g to about 31 meq/100 g, or 5 meq/100 g to about 31 meq/100 g. In some embodiments, the CEC is at least 5 meq/100 g. In some embodiments, the CEC ranges from 5 meq/100 g to about 31 meq/100 g.

In certain embodiments, aerobic digestion products produced by the methods and processes described herein are applied to the soil where a plant grows or will grow, to the seeds of a plant, or to a plant itself. It is contemplated that when an aerobic digestion product produced by the methods and processes described herein is applied to the plant, it can be applied, for example, in-furrow, as a foliar spray (e.g., ground spray, by plane), by drip, in flood irrigation, during overhead irrigation, sidedress injection into the soil (e.g., with nitrogen), in the vicinity of the roots of the plant, to the plant part(s) (e.g., roots, branches, and stems) directly, to the rooting zone, and/or to an area proximate to the plant. In certain embodiments, the aerobic digestion products are applied to a reproductive tissue, including but not limited to buds, flowers, and developing structures that contain seeds, such as fruit and seed pods. The aerobic digestion products may be applied at various stages of plant development. In some embodiments, the aerobic digestion products are applied to the seed before the growth of a seedling. In some embodiment, the aerobic digestion products are applied during or after the growth of a seedling. The aerobic digestion products may also be applied before or after leaf emergence or during blossom.

The aerobic digestion products function as a biostimulant, promoting nutrient uptake and overall plant health. While the biostimulant properties may be at least in part attributable to chelation capabilities of the aerobic digestion products, other properties also contribute to overall biostimulant properties, including improved nutrient bioavailability and uptake, improved tolerance to stress, and improved soil quality.

In certain embodiments, at least 0.01 parts of aerobic digestion products (e.g., free humic acids and free fulvic acids) per million parts of the composition (e.g., fertilizer) is applied. The term "ppm," as used herein, refers to parts by weight of the aerobic digestion products per one million parts by weight of the composition or a fertilizer. In some embodiments, the amount of aerobic digestion products in the composition is from about 0.01 ppm to about 50,000 ppm, about 0.1 ppm to about 10,000 ppm, about 1 ppm to about 5,000 ppm, about 10 ppm to about 2,500 ppm, about 100 ppm to about 2,000 ppm, or about 500 ppm to about 1,500 ppm. In some embodiments, the amount of aerobic digestion products is from about 1 ppm to about 5,000 ppm, about 10 ppm to about 2,500 ppm, or about 100 ppm to about 2,000 ppm of the composition. In some embodiments, the amount of aerobic digestion products in the composition is at least 0.001 ppm, 0.01 ppm, 0.1 ppm, 1 ppm, 10 ppm, 100 ppm, 1,000 ppm, 10,000 ppm, or 100,000 ppm.

In certain embodiments, about 0.5 quart to about 10 quarts of a product composition comprising aerobic digestion products is applied per acre in a single application. In some embodiments, about 1 quart to about 6 quarts of a product composition comprising aerobic digestion products is applied per acre in a single application. Multiple applications may be made throughout the year. In some embodiments, about 1 quart of a product composition comprising aerobic digestion products is applied for every 2-5 gallons of liquid fertilizer that is applied.

In certain embodiments, the aerobic digestion product composition or the product composition is mixed with a dry fertilizer. In these embodiments, about 1 quart to about 5 gallons of the aerobic digestion product composition is mixed per fertilizer ton. Suitable dry fertilizers include granular material and soil amendments. In certain embodiments, the aerobic digestion product composition can be blended with other biotechnologies.

In certain embodiments, the amount of aerobic digestion products (e.g., free humic acids and free fulvic acids; microbial metabolites) used in a composition may depend upon particular situations or factors, such as soil pH, temperature, soil type, etc., and on the mode of application. For example, application of aerobic digestion products to the soil (e.g., free humic acids and free fulvic acids; microbial metabolites) can be prolonged over a period of many months. In some embodiments, the amount of aerobic digestion products to be applied in a broadcast application is greater than in a row or band application, which permits a high concentration of the aerobic digestion products to be applied within close proximity to the plant. Applied near the root zone of growing plants, or immediately prior to seeding or transplanting, a lesser amount can be used than when the application is made at the end of the growing season to prepare the soil for the following season.

Method for Removing or Sequestering Heavy Metals from a Soil or Other Environment Heavy-metal contamination of water and soils is a serious environmental concern. For example, heavy metals (such as mercury) from mining leach into water that comes into contact with the contaminated soil, which gives rise to environmental hazards in both the contaminated soil and the water. Given the superior chelating capacities the aerobic digestion products described herein, they are useful for treating or removing heavy-metal contamination in an environment (e.g., soil or water). Thus, in another aspect the disclosure provides methods for remediating soils and water with heavy metal contaminants. In certain embodiments, the remediation methods comprise applying an effective amount of an aerobic digestion product produced by the methods and processes disclosed herein, either in a free molecular binding process (e.g., in a soil environment), or by immobilizing organic acids of the aerobic digestion products onto a solid stationary matrix for metal biosorption from contaminated water. In certain embodiments, the aerobic digestion products produced by the methods and processes described herein can be used to remove heavy metals from soils, water, and other contaminated sites.

In certain embodiments, metals that can be chelated include but are not limited to heavy metals such as mercury, cadmium, chromium, copper, lead, nickel, and zinc, as well as lighter metals (e.g., aluminum). In certain embodiments, the remediation methods comprise (1) dispensing the aerobic digestion products into the contaminated water or soil, (2) adding a coagulant, (3) agitating the mixture, (4) coagulating a mixture to form sludge, and (5) removing the sludge. The sludge produced by the methods comprises a complex of aerobic digestion products (e.g., organic acids) and metal contaminants. In certain embodiments, the remediation methods comprise immobilizing organic acids of the aerobic digestion products of the present methods and processes onto a stationary matrix (e.g., polymer particles or capsules, monolith, silica, etc). The matrix with immobilized organic acid is then contacted with the contaminated site.

"Coagulant" refers to any substance that can form a complex with free organic acids (e.g., humic acids or fulvic acids) capable of chelating the metal ions. In certain embodiments, the coagulant is a metal salt (e.g., iron salts and aluminum salts). Non-limiting examples of useful coagulant includes ferric chloride, ferric sulfate, aluminum chloride, and aluminum sulfate.

The mass ratio of the free organic acids to the coagulant may affect the efficiency of the metal removal process. In certain embodiments, the mass ratio employed is at least 1:0.5, 1:0.2, 1:0.1, or 1:0.05, when light metals such as aluminum are being removed. For heavy metals, in certain embodiments the mass ratio is at least 0.5:1, 1:1, or 1:2.

The formation of the complex of aerobic digestion product (e.g., organic acid) and metal contaminant can be affected by the pH of the contaminated environment. In certain embodiments, the pH is adjusted to an appropriate value for effecting chelation. For example, the pH may be adjusted to a pH in the range of 4-10, and more preferably in the range of 5-6. In some embodiments, a suitable basic composition can be added to adjust the pH. Suitable basic compositions include but are not limited to hydrated lime, calcium oxide, magnesium hydroxide, soda ash, and sodium hydroxide.

In certain embodiments, sludge is removed by any suitable means, which includes but is not limited to filtering, decanting, centrifuging, and using a clarifier (i.e., a settling tank).

When used for treating heavy-metal contamination in soil, the free organic acids (e.g., humic acids and fulvic acid) enhance pollutant retention and reduce pollutant leaching. The organic acids, in some embodiments, can attach to the soil particles, generating a long-lasting effect for the metal-removal function.

Once the organic acids form complexes with heavy metals, the complexes comprising heavy metal can be extracted.

In some embodiments, the aerobic digestion products are used to reduce free heavy metal concentrations in soils, providing for improved plant germination and growth. Excessive heavy metal buildup can be toxic to agricultural soils and can affect plant germination and growth. By applying aerobic digestion products described herein to the soil, a sufficient proportion of excess heavy metals can be chelated and sequestered, improving germination and plant growth.

EXAMPLES

The materials, methods, and embodiments described herein are further defined in the following Examples. It should be understood that these Examples, while indicating certain embodiments, are given by way of illustration only. From the disclosure herein and these Examples, one skilled in the art can ascertain the essential characteristics of this invention, and without departing from the spirit and scope thereof, can make various changes and modifications of the invention to adapt it to various usages and conditions.

Example 1—Analysis of Organic Acids

The organic acids produced by the methods and processes described herein were subjected to humic and fulvic acid determination by the AOAC/Lamar/IHSS method, liquid chromatography-mass spectrometry (LC-MS) and Fournier transform infrared spectroscopy (FTIR) analysis.

Table 1 provides a summary of humic substance content of products produced by a leonardite-degrading reactor system.

TABLE 1

Summary of humic and fulvic acid concentrations and viscosities of system product and downstream processing products.

| System product technologies | Humic Acid (%) | Fulvic Acid (%) | Humin particulate (%) | Viscosity, cP |
|---|---|---|---|---|
| System supernatant | 1.19 | 1.11 | — | 1.01 |
| System product 80/20 (supernatant/floc) | 4.81 | 2.15 | — | 1.08 |
| System product 50/50 (supernatant/floc) | 4.77 | 1.44 | — | 1.15 |
| System product enriched with chemically extracted leonardite | 13.64 | 4.01 | 0.04 | 2.28 |
| System product enriched with chemically extracted leonardite; PAA added | 11.63 | 9.75 | 0.28 | 2.34 |
| System product enriched with chemically extracted leonardite; centrifuged to remove humins | 12.85 | 6.20 | 2.25 | 1.45 |
| System product enriched with chemically extracted leonardite; centrifuged to remove humins; PAA added | 14.86 | 2.32 | — | 1.62 |

TABLE 2

Chelation efficiency, total humic and fulvic acid content, and COO⁻ chelation factor for system products, downstream processing products, and a commercial humic acid product.

| System product-based technologies | Chelation efficiency (%) | Total HA + FA content (%) | COO⁻ chelation factor | CEC* (meq/100 g) |
|---|---|---|---|---|
| System Product | 50.37 | 2.3 | 21.9 | 13.5 |
| System product enriched with chemically extracted leonardite; centrifuged to remove humins | 76.87 | 19.05 | 4.03 | 11.6 |
| Commercial humic acid product (22% humic acid) | 54.74 | 3.09 | 10.9 | 10.2 |

*CEC measurement of calcine clay particles which had been treated with equivalent volumes of each of the different types of humic acid products.

Figure 4:
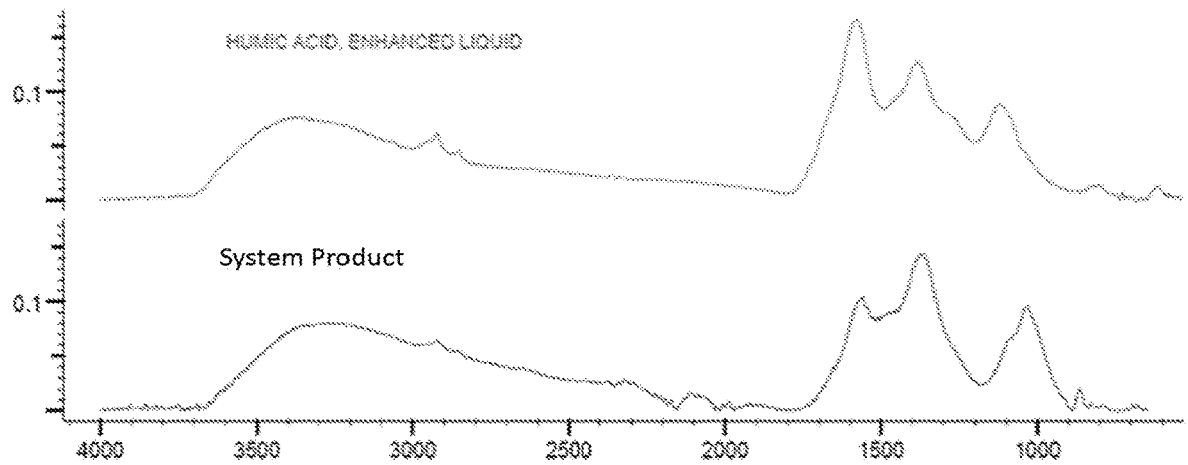
FIG. 4 depicts the Fourier Transform Infrared Spectroscopy (FTIR) analysis of outputs from a bioreactor system according to an embodiment of the present disclosure.
Figure 5A:
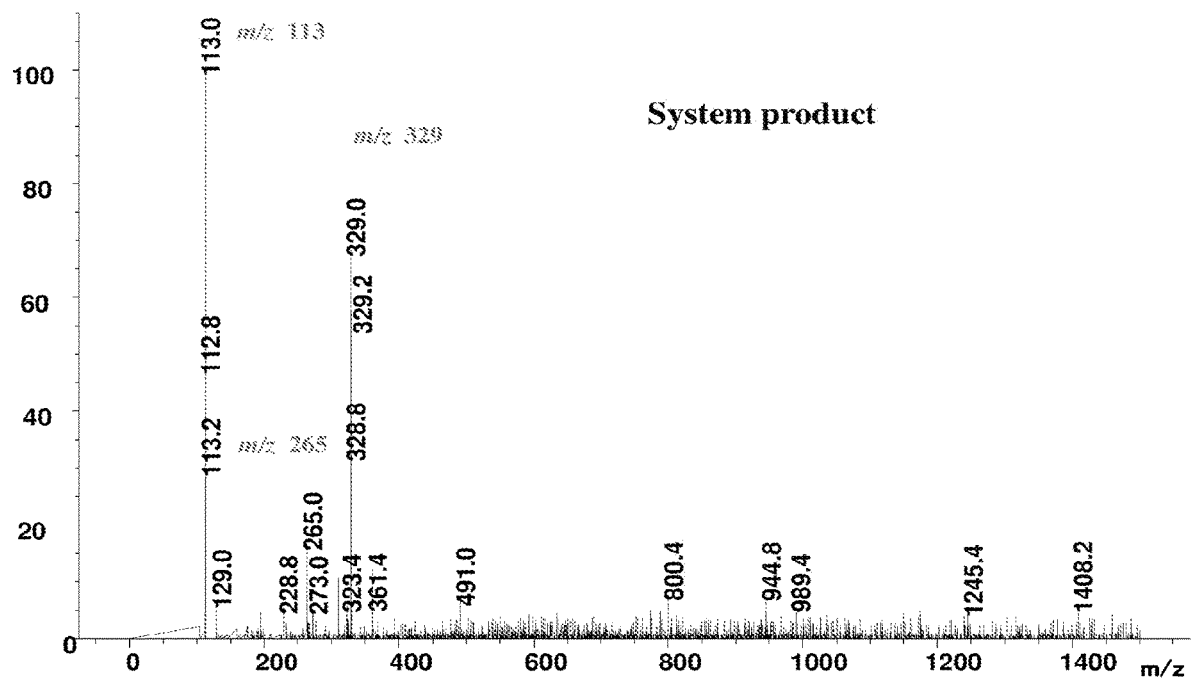
FIGS. 5A-5C depict liquid chromatography-mass spectrometry (LC-MS) analysis of intact output (i.e., system product.
Figure 5B:
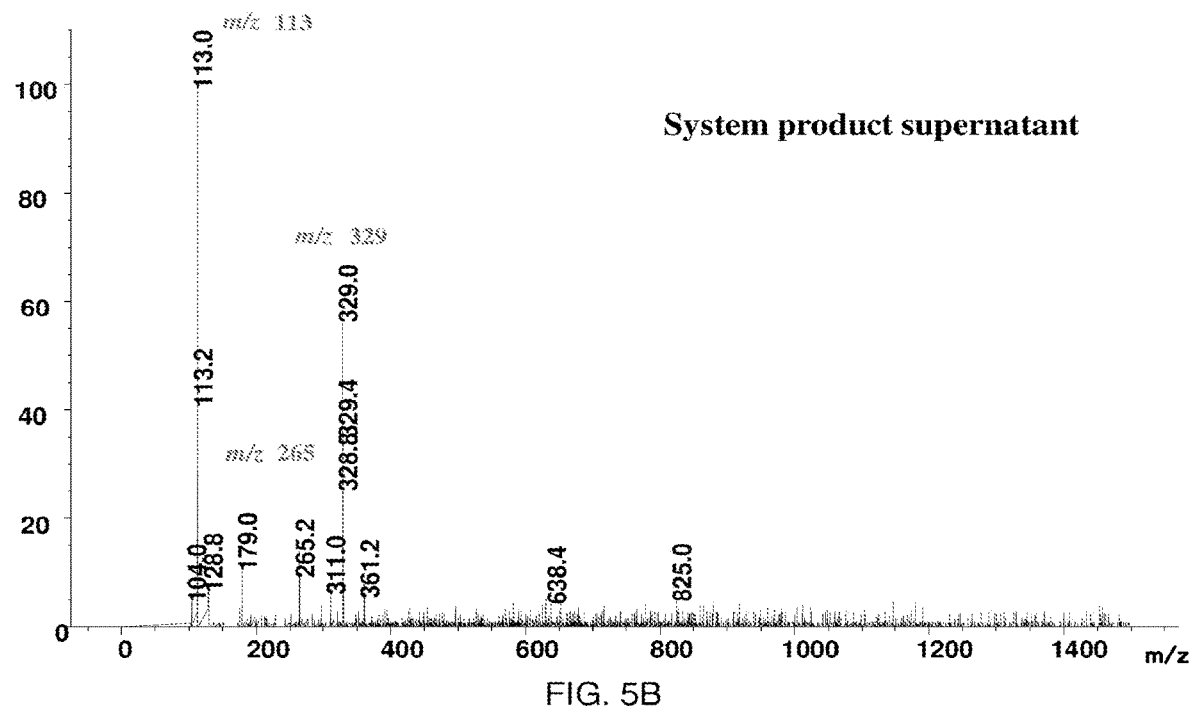
Figure 5C:
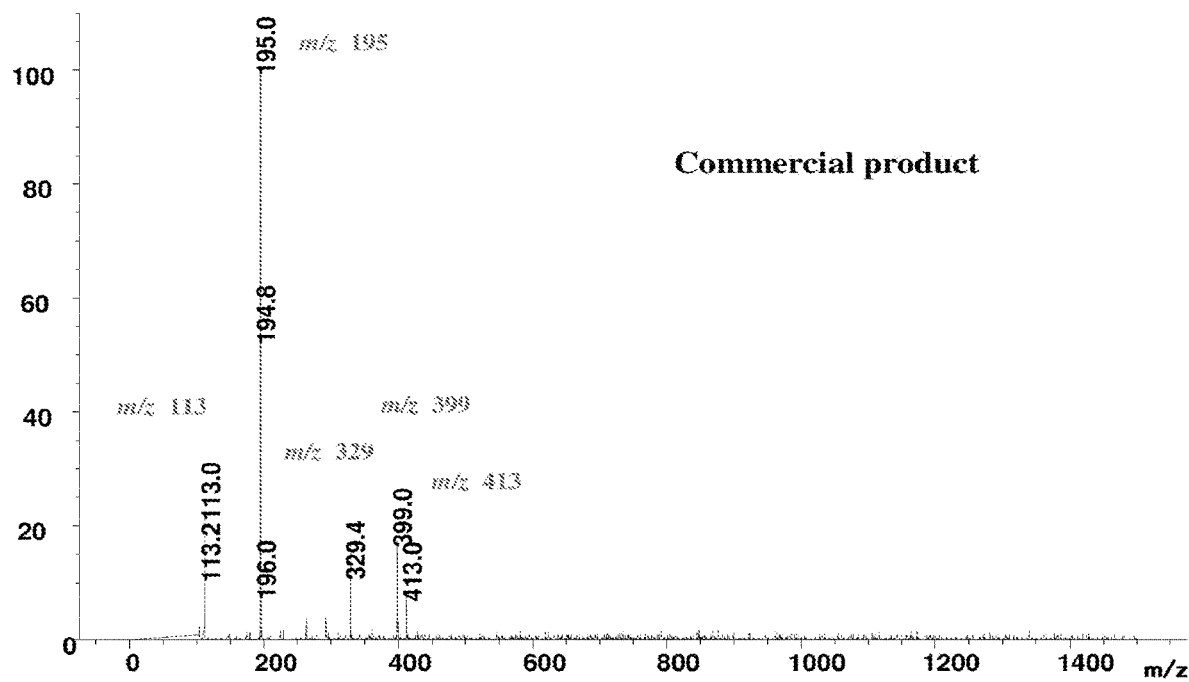

The FTIR spectra indicated that similar functional groups were present in BioRad humic acid standard Know-It-All™ library, and key functional groups such as C=O of carboxylic acids and ketone and C=C of aromatic carbon rings (FIG. 4) were identified. FIG. 5 presents mass spectrographs comparing the system product, system product supernatant, and a commercially available humic acid product. System product and its supernatant exhibited similar mass chromatograms with relative intense peaks at m/z 113 and 329; while the commercially available product had a different spectrum with a main peak at m/z 195 and other two ions at m/z 399 and m/z 413.

Figure 23:
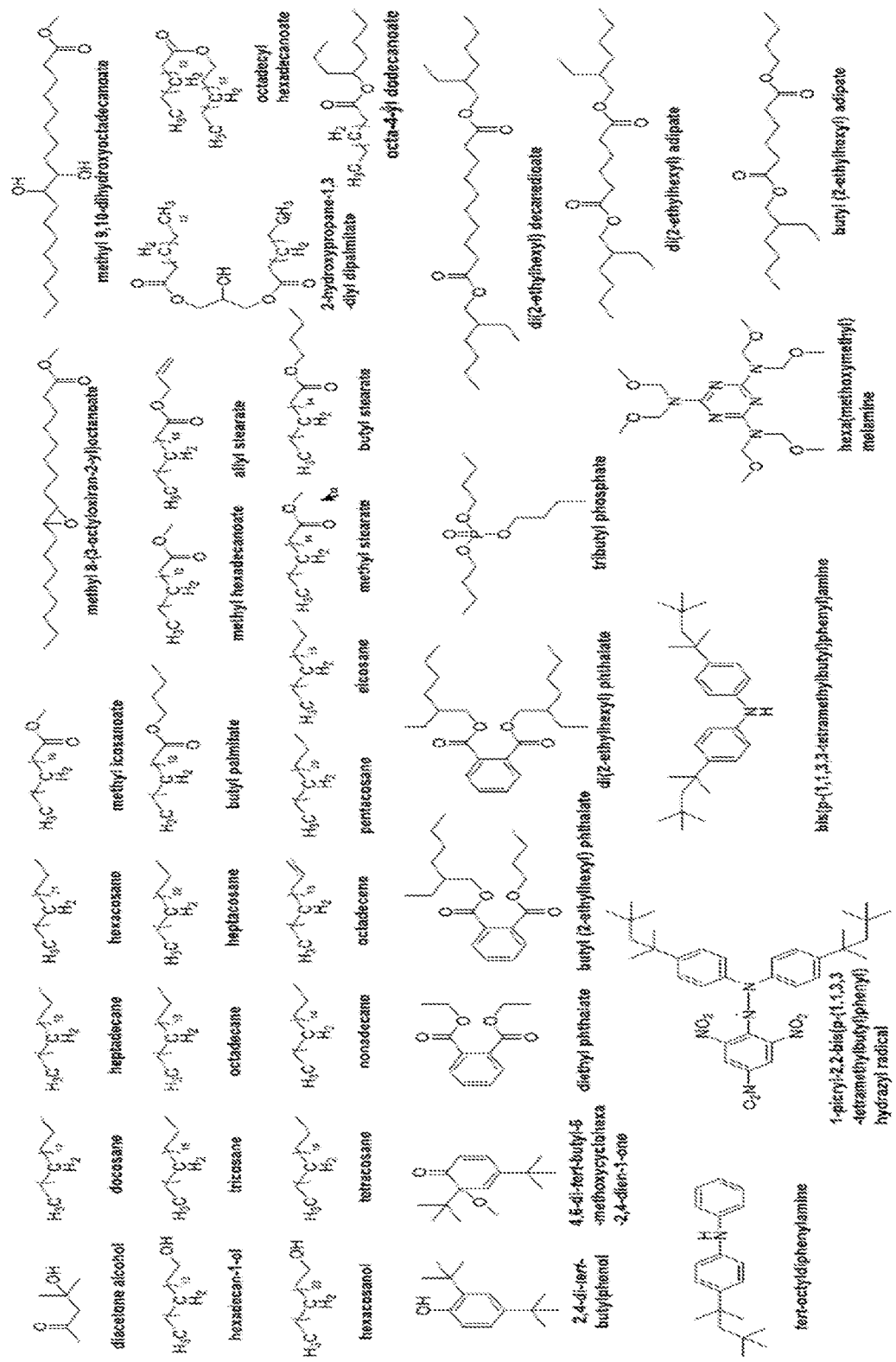
FIG. 23 illustrates compounds identified through NMR and GC-MS analyses of semi-purified compounds from ethyl acetate and butanol extracts of system products.

The major chemical compounds of the system product were identified by LC-MS and NMR analysis of ethyl acetate and butanol extracts. These included various fatty acid esters, alcohols, phenols, amines, long-chain alkanes and alkenes, and phthalates. Examples of non-organic acid compounds are provided in FIG. 23, which may be indicative of primary and secondary microbial metabolites.

Figure 13:
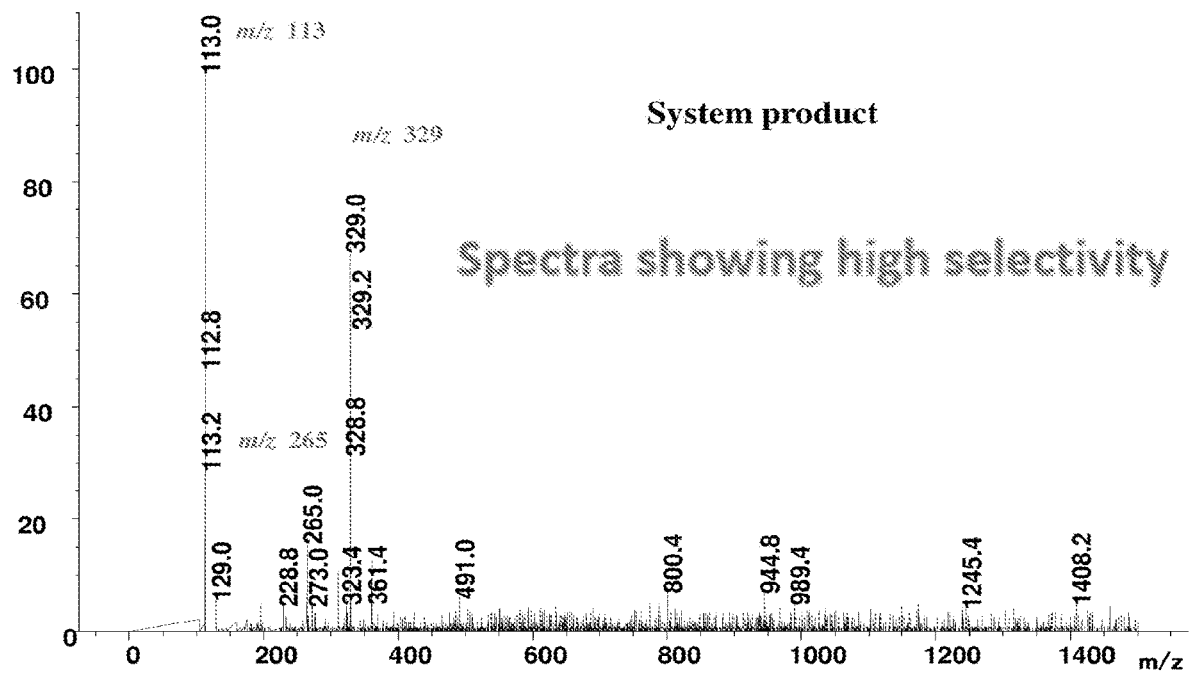
FIG. 13 depicts a mass spectrograph for organic acids and other system product chemistry occurring in the supernatant produced by the methods and processes described herein.

FIG. 13 depicts mass spectrographs for the system supernatant of an embodiment of the methods described herein. The main molecular fragments depicted by the spectrograph of system supernatant are those with mass/charge (m/z) ratios of 113, 265 and 329. Molecular assignment at these m/z ratios indicate moieties of humic acids having free organic acids sites available for metal ion binding. The mass spectrographs support that system supernatant contains a high composition of free organic acids, demonstrating the selectivity of the biological extraction process for free organic acids generation.

Example 2—Chelation Efficiency and Capacity of Aerobic Digestion Products

Early investigations suggested that for an effective chelation product two phenomena must be considered: (1) the exchange of cations between organic acids and an aqueous soil environment, and (2) the adsorption and desorption of organic acids from the soil particulate surface. The latter has been observed as an important factor that may affect the efficacy of system products (i.e., soil column experiments showed that system products can easily be leached/eluted out of the soil compared to more concentrated commercially available humic acid products).

An assay was developed with these observations in mind. The assay is a simplified method that can analyze up to several samples with replicates, has reproducible results and short turn-over, and use/generate the least amount of hazardous chemicals. It can account for both phenomena of cation exchange and system product adsorption onto soil, and results follow trends of organic acid/humic substance concentrations in the treatment.

The following chelation efficiency protocol is differentiated from soil cation exchange capacity by performing the test at the soil's native pH and by measuring the fraction of metal ions that are adsorbed on the soil and the aqueous phase in equilibrium. That is, the chelation efficiency can be derived from the equilibrium partition constant between soil and water. An approach is shown here represented in terms of concentrations rather than fugacity for simplicity:

$$K_{soil\text{-}water} = \frac{\text{Concentration of metal ion adsorbed or chelated on soil particle surface}}{\text{Concentration of free metal ion in aqueous phase}}$$

$$K_{soil\text{-}water} = \frac{Cs}{Cw}$$

$$K_{soil\text{-}water} = \frac{Ct - Cw}{Cw} = \frac{Ct}{Cw} - 1$$

$$\frac{Cw}{Ct} = (Ksw + 1)^{-1}$$

$$1 - \frac{Cw}{Ct} = 1 - (Ksw + 1)^{-1} = \frac{Cs}{Ct} = \text{Chelation Efficiency}$$

where, Ct is the total metal ion concentration, Cs is the quantity of metal ion in the soil phase, while Cw is the concentration of the metal ion in the aqueous phase. Also, at equilibrium, $K_{soil\text{-}water}$ will be a function of the partition constant of organic acid in soil and water, chelation constant of metal ion in soil and chelation constant of metal ion in organic acid.

The test is performed for a specific metal ion (e.g., magnesium, zinc) and for a specific type of soil (e.g., an agricultural soil from Denton, TX). Because of the low concentration of organic acids in raw system products (i.e., not concentrated), a high application rate is necessary (i.e., 20 mL of system products to 100 g soil) to observe data that can be correlated with humic substance concentrations. The treatments are compared with positive controls with the same application rate. Because of the high application rates necessary, the results are intended for use in process monitoring of organic acid concentrations in system products or an estimate of effects on chelation after long-term application of system products.

Methodology

A soil of interest was first dried at 30° C. until weight is stable, and then sifted through a 0.1 mm sieve. To 250 g of the dried soil, 50 ml of system product or control was added. The soil and liquid treatment was mixed to evenly coat the soil particles. The mixture should form a slurry. If too watery, the volume of liquid treatment added was reduced. To enable an equilibrium calculation, all organic matter must be initially absorbed onto the soil particles. The slurry was allowed to dry at room temperature for 12 to 16 hours. If the slurry solidified into a block, the block was ground into fine particle with a mortar and pestle.

10 g of treated soil and appropriate controls was transferred into 50 ml conical centrifuge tube. High-density system products and controls were diluted to obtain a density of about 1 g/ml. 2 ml of 0.1 M cation solution was then added to the soil in the conical tube, and the mixture was vortexed to coat the soil evenly before being allowed to dry for about 4 hours. 0.1 M solutions were used due to the low concentration of organic acids in the raw (i.e., non-concentrated) system products. Higher concentrations can be used for more concentrated products. The moles of metal ion in the entire equilibrium mixture should be in excess of the corresponding mole of chelant in the treatment. 20 ml of deionized water was added to each tube and mixed gently by inverting each tube several times to allow for full contact of soil surface with the aqueous solution. The mixtures were allowed to equilibrate for 15 minutes at 25° C. before being centrifuged for 15 minutes at 7,000×g. The supernatant was then decanted. Concentrations of metal ion in the supernatant were analyzed by inductively coupled plasma optical emission spectrometry (ICP-OES). The following were run for blanking: a) water-treated soil with metal ion solution added, b) water-treated soil without metal ion solution added, and c) treated soil without metal ion solution added.

For this protocol, the chelation efficiency was computed, where x is the concentration of metal ion in the supernatant:

$$\text{Chelation Efficiency} = \frac{0.002L * 0.1MC^+ - 0.02L * xMC^+}{0.002L * 0.1MC^+}$$

To calculate chelation capacity:
Let i represent m no. of treatments
Let j represent n no. of cations analyzed
Let w be water treated and no-cation treated
Let ppm be concentration in ppm of cation in supernatant
Let Stdoj be concentration of standard for cation j in ppm
Let Cij be mg of cation chelated by each treatment for each cation, $$\begin{bmatrix} Cij & \cdots & Cin \\ \vdots & \cdots & \vdots \\ Cmj & \cdots & Cmn \end{bmatrix} =$$

$$0.02 * 2 \left( \begin{bmatrix} Stdo1 & \cdots & Stdo1 \\ \vdots & \cdots & \vdots \\ Stdom & \cdots & Stdom \end{bmatrix} + \begin{bmatrix} PPM_{ww} & \cdots & PPM_{ww} \\ \vdots & \cdots & \vdots \\ PPM_{ww} & \cdots & PPM_{ww} \end{bmatrix} \right) +$$

$$\left( \begin{bmatrix} PPM_{iw} & \cdots & PPM_{mw} \\ \vdots & \cdots & \vdots \\ PPM_{iw} & \cdots & PPM_{mn} \end{bmatrix} - \begin{bmatrix} PPM_{ww} & \cdots & PPM_{ww} \\ \vdots & \cdots & \vdots \\ PPM_{ww} & \cdots & PPM_{ww} \end{bmatrix} \right) -$$

$$0.02 \left( \begin{bmatrix} PPM_{ij} & \cdots & PPM_{mj} \\ \vdots & \cdots & \vdots \\ PPM_{in} & \cdots & PPM_{mn} \end{bmatrix} - \begin{bmatrix} PPM_{wj} & \cdots & PPM_{wn} \\ \vdots & \cdots & \vdots \\ PPM_{wj} & \cdots & PPM_{wn} \end{bmatrix} \right)$$

To compute for chelation capacity in terms of mg cation chelated/unit quantity product:

$$\text{Chelation capacity} = \frac{Cij}{N}$$

where N could be g of organic matter (OM), g of humic substances (HS) or mL of treatment onto soil.

Results

Figure 15:
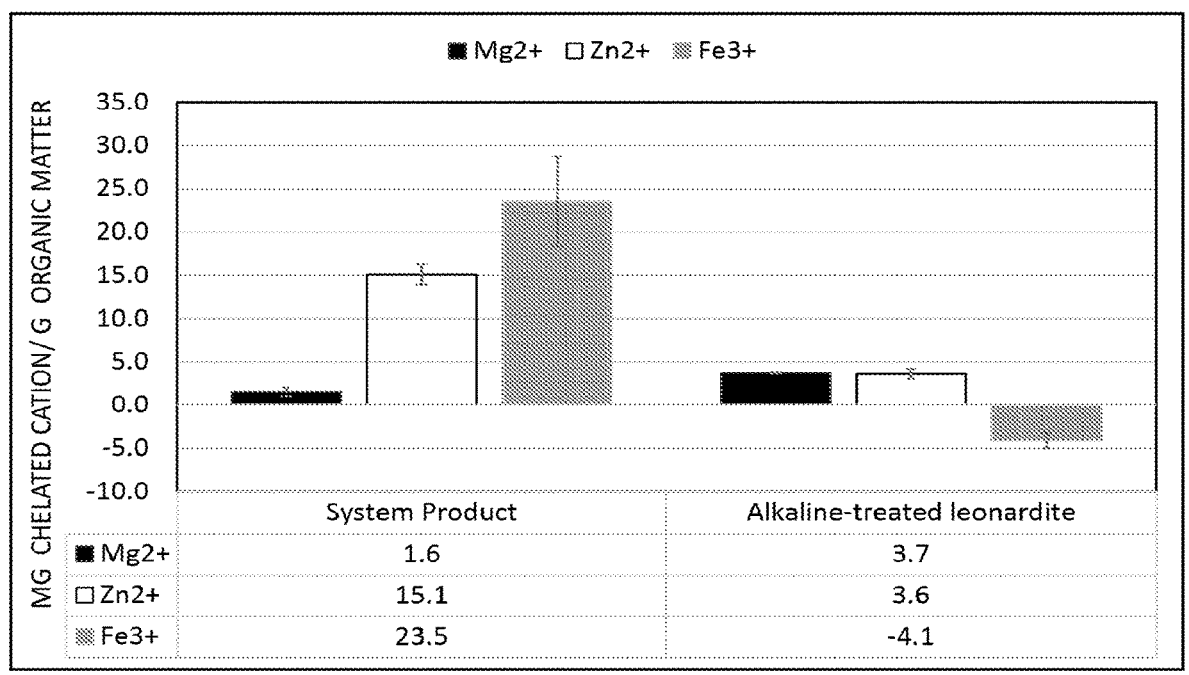
FIG. 15 is a bar graph illustrating the chelation capacity of system products and alkaline-treated leonardite for magnesium, zinc, and iron according to an embodiment.

The chelation capacity of the system products was determined and compared with alkaline-extracted organic acids from the parent leonardite. Specifically, parent leonardite (10 g) was mixed for 8 hrs in 1% KOH in water (100 mL) and diluted 10 times (~pH 8, ~specific gravity 1, ~0.6% OM). Each treatment was applied to agricultural soil (sandy loam soil from Denton County, TX, native pH of 7.4, 1.9% organic matter, CEC of 12.7 meq/100 g, sifted through 0.4 mm mesh and dried at 30 C for 4 days) at a rate of 20 mL per 100 grams soil, dried and incubated with either deionized water or standardized solutions of magnesium sulfate, zinc sulfate or ferric chloride. After incubation, the soil was separated from the supernatant by centrifugation and filtration. The cations left in the supernatant were excess species that were not immobilized and chelated by either the treatment or soil. The concentration of cations in the supernatant was measured through ICP-OES (Inductively-Coupled Plasma Optical Emission Spectroscopy). The chelation capacity (reported as mg chelated cation per g organic matter) is calculated by using a mass balance around the supernatant and the experimentally determined organic matter content of the treatment. Results showed that alkaline-treated leonardite had higher chelation capacity for magnesium ions in the agricultural soil, but the system product had higher chelation capacity for zinc ions. The alkaline-treated leonardite lowered the native chelation capacity for ferric ions of the agricultural soil while the system product increased the chelation capacity for this cation (FIG. 15). Overall, the alkalinized leonardite had less improvement in soil CEC than the aerobic digestion products, demonstrating the utility of the degradation of leonardite through the biological methods using the systems and processes described herein.

Example 3—Cation Exchange Analysis of System Product Based on pH Change 15 g of Turface™ (a soil substitute) in a column was treated with 10-15 mL of each sample (system product/H$^+$ and system product for the acidic range test, and system product/OH— and system product for the alkaline range test, where "system product" denotes organic acids produced by the methods and processes described herein) separately and was incubated at room temperature for 2 hour. System product/H$^+$ refers to acidified system product whilst system product/OH$^-$ refers to alkalinized system product. Fe$^{3+}$ stock solution of ferric chloride with an initial pH of 3.05 was prepared, introduced into the Turface column, and incubated for 2 hours. The pHs of the leachates were measured. The degree of cation exchange was estimated based on the change in pH between the stock FeCl$_3$ solution and the leachates. FeCl$_3$ reduces or loses its electrophilicity and acidity upon successful cation exchange with existing metal ions in the treated soil bed such as monovalent metal ions including K$^+$ and Na$^+$. The more ferric chloride in the leachate, the less has been chelated by the treated turface.

Figure 9A:
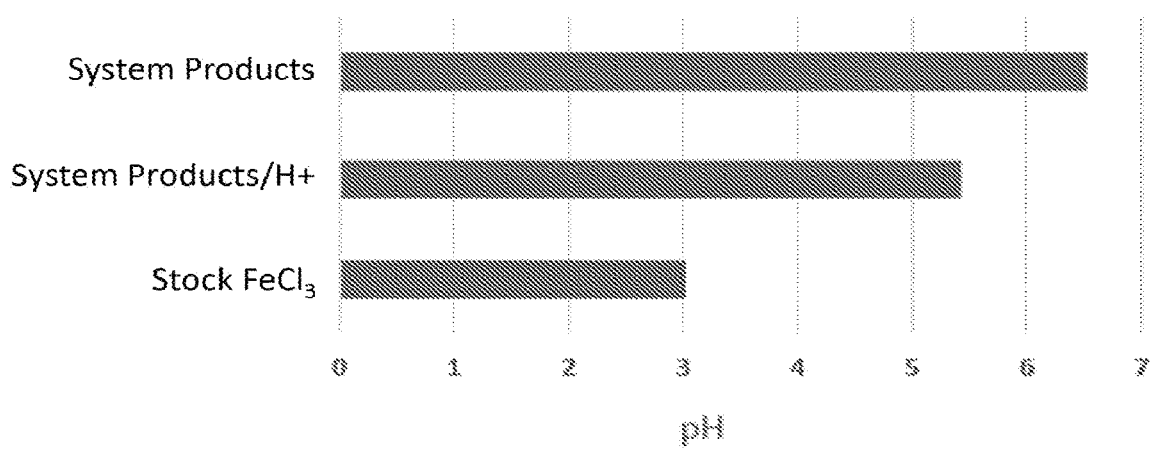
FIGS. 9A and 9B depict the pH of soil column leachates. These results represent a qualitative evaluation of the cation exchange capacity of output products from a bioreactor system according to an embodiment of the present disclosure. The evaluation is based on pH change of leachate after FeCl3 passed through a soil column treated with System Products which were either under acidic (FIG. 9A) or alkaline (FIG. 9B) conditions. The degree of cation exchange can be estimated based on the change in pH between the stock FeCl3 solution and the leachates.

As depicted in FIG. 9A, pH increased from 3.05 to 5.4 in system product/H$^+$. Without being bound by any particular theory, this was likely due to successful exchange of Fe$^{3+}$ from the stock solution.

Figure 9B:
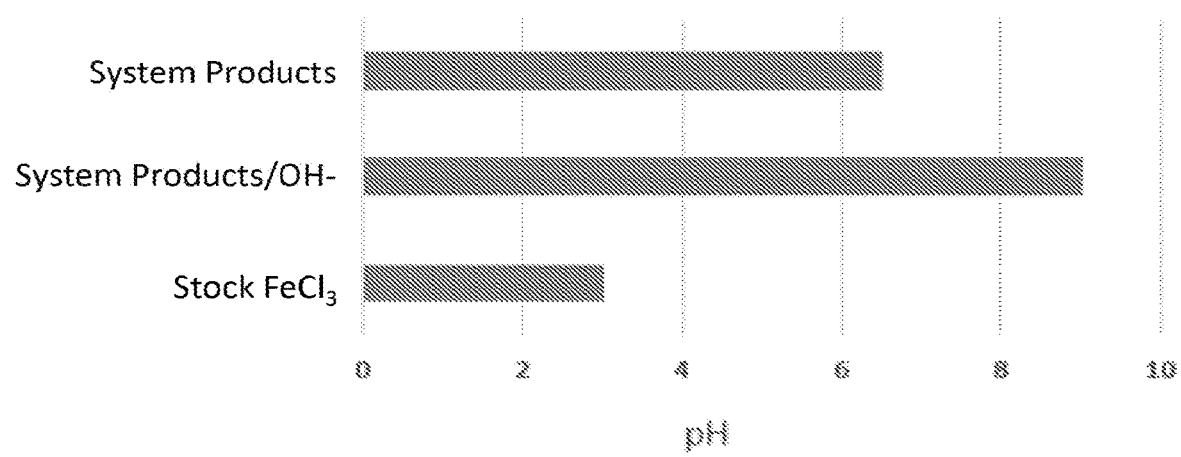

As depicted in FIG. 9B, pH increased from 3.05 to 9 in system product/OH$^-$. Without being bound by any particular theory, this was likely due to successful exchange of Fe$^{3+}$ with hydrogen or other mono- or divalent ions from the stock solution resulting in a higher pH leachate solution.

Example 4—Cation Exchange Capacity of System Product

The effect of high-rate application of the system product on Soil Cation Exchange Capacity (Soil CEC) and nutrient availability of an agricultural sandy loam soil was determined. This soil had a native pH of 7.4 and native organic matter content of 1.9%. Briefly, 20 mL of either the system products, water, or alkaline-treated leonardite (0.5 g leonardite in 0.065% KOH) was applied to 100 g sandy loam soil (sifted through 0.4 mm mesh and dried under 30° C. for 4 days). Two replicate samples were produced. After treatment and drying, the soil CEC at pH 7 and Mehlich-3 extractable nutrients were analyzed.

The average calculated soil CEC across the two replicate samples was higher for both of the system products relative to water or the alkaline-treated leonardite. In addition, magnesium, sulfur, zinc, and copper which are nutrients important for plant growth, had higher average concentrations in soil samples treated with the two system products (see Table 3). The higher concentration of metal ions in the soil samples treated with the system product is due to the enhanced CEC performance conferred to the soil by the system product to retain nutrients from the soil.

TABLE 3

Soil cation exchange capacity and nutrient availability

| | Soil Cation Exchange Capacity (meq/100 g) | Mehlich 3-extractable Nutrients (ppm) | | | | |
|---|---|---|---|---|---|---|
| | | Magnesium | Sulfur | Zinc | Iron | Copper |
| Untreated agricultural soil | 12.7 | 158 | 20.5 | 3.25 | 290 | 1.35 |
| System Product Iteration 1 | 14 | 182 | 44.5 | 7.85 | 296 | 7.6 |
| System Product Iteration 2 | 13.6 | 172.5 | 39.5 | 6.15 | 286 | 5.45 |
| Alkaline-extracted leonardite | 12.7 | 168.5 | 33 | 3.4 | 287 | 1.45 |

Example 5—Fe$^{2+}$ Binding Strength Evaluation of Organic Acids

Fe$^{2+}$ chelation strength performances of organic acids produced by methods and processes described herein and concentrated organic acids were determined by measuring the concentration of Fe$^{2+}$-ferrozine complex in the free Fe$^{2+}$ phase after humic acid chelation. A 200 µL aliquot of each solution was mixed with 40 µL of 0.1 mM FeCl$_2$×4H$_2$O and allowed to incubate for 30 min before adding 40 µL of 5 mM ferrozine. The reaction mixtures were kept for additional 30 min at room temperature. Control samples were prepared in the same way with ferrozine replaced with RO water. All the samples were run in duplicate. Chelation of free Fe$^{2+}$ ions by ferrozine generated a colored complex that was measured at 562 nm using a microplate reader. The concentration of free Fe$^{2+}$ was estimated from a pre-determined the Fe$^{2+}$-ferrozine/Fe$^{2+}$ calibration curve and was used to determine the concentration of bound Fe$^{2+}$.

Figure 14:
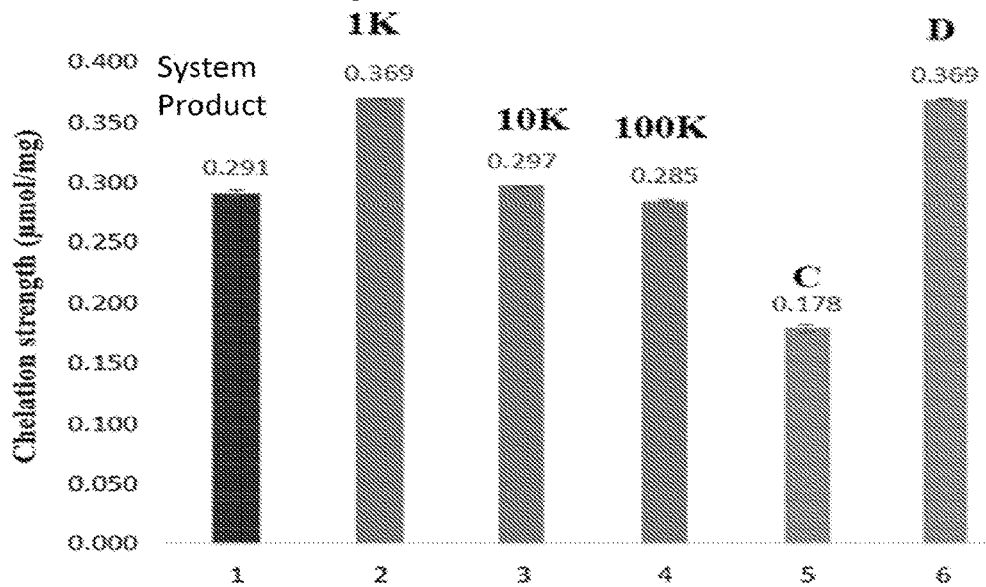
FIG. 14 is a bar graph illustrating the results of Fe' bind analysis, comparing products of the methods and processes described herein and commercially available humic acid products. Samples 1, 2, 3, 4, 5, and 6 represent intact system supernatant, 1 kDa filtrate of system supernatant; 10 kDa filtrate of system supernatant; 100 kDa filtrate of system supernatant; Borregro® HA-1 (33% solution); and a system product enriched with chemically extracted leonardite and centrifuged to remove humins, respectively.

FIG. 14 illustrates the Fe$^{2+}$ binding strength analysis results for the organic acids and conventional humic acid product HA 1. Sample 1 is intact system supernatant containing free organic acids. Sample 2 is 1 kDa filtrate of system supernatant primarily containing volatile organic compounds, aliphatic organic acids, and free oligomeric fragments of humic acids generated via microbial digestion. Sample 3 is 10 kDa filtrate of system supernatant containing the components of sample 2, different molecular weight fulvic acids and low molecular weight ulmic acids. Sample 4 is 100 kDa filtrate of system supernatant containing the components of sample 3, high molecular weight ulmic acids, and different molecular weight humic acids. Sample 5 is commercially available HA-1 (33% solution). Sample 6 is a downstream modification of the supernatant, in which the humins have been removed and additional humic acids are added to a comparable level as in the commercial products.

From the data, the 1 kDa and 10 kDa fractions of system supernatant exhibited a higher chelation strength compared to intact system supernatant due to the enrichment of small molecule free organic acid moieties with significant electronegativity and mass density for metal ion binding. All the system-derived samples displayed higher binding strengths than HA-1. Sample 6 demonstrated the highest binding strength performance. Sample 6 is enriched with free organic acids from system supernatant with additional binding sites generated via further concentration. Samples 5 and 6 contained equivalent amounts of humic acids but demonstrated different degrees of metal ion binding strength. This indicates that the presence of free organic acids is an important driver of metal ion binding as opposed to total organic acids, thus the reason behind the superior chelation performances of the system-based samples.

Example 6—Microbial Analysis

The microbial content of the working solution of the methods and processes described herein as analyzed at various time points. A nutrient media created from leonardite was utilized in the analysis. No additional carbon or nitrogen sources were added to the nutrient media. For organisms to grow on the leonardite nutrient media, they must be able to degrade leonardite as the sole source of carbon.

Alkalinized leonardite media (ALM) can have several embodiments. Leonardite (1.0 g to 10.0 g per mL) is pre-treated with a very dilute solution of KOH (0.03M KOH). This pre-treated leonardite was designed to be similar to the leonardite solution put into the multiphase bioreactors. The microbial nutrient media typically contains pre-treated leonardite (15% v/v), M9 salts (10% v/v of a 5× stock, Sigma M6030), a trace mineral solution (0.1% v/v of solution (in 1 L): MgSO$_4$ 0.25 g, KCl 0.25 g, KH$_2$PO$_4$ 0.5 g, Fe$_2$(SO$_4$)$_3$·6H$_2$O 0.15 mg, MnSO$_4$×H$_2$O 5.0 mg, CuSO$_4$·5H$_2$O 0.16 mg), CaSO$_4$ (0.01%) and Noble agar (18% w/v, Sigma A5431). For determination of the abundance of total heterotrophic bacteria a general, non-selective medium ("¼-TSA", which is a quarter strength preparation of tryptic soy broth agar (Difco #236920) was used.

Table 4 presents the total abundance of heterotrophic bacteria ("¼ TSA" media) and abundance of leonardite degrading bacteria ("ALM" media) at various timepoints for multiple different leonardite degrading reactor systems reactor four (R4) working solution. Reactor systems 1 and 2 included an exogenous microbial stock solution, while reactor system 3 did not. Reactor systems 1 and 3 were pilot-sized systems, with product outputs of approximately 4-8 gallons per day, while reactor system 2 was a commercial scale production system with a product output of approximately 3000 gallons per day. The leonardite degrading reactor systems R4 working solutions have 10$^5$ to 10$^7$ colony forming units per mL (CFU/mL) of leonardite degrading bacteria.

TABLE 4

Summary of the abundance of total culturable heterotrophic bacteria ("1/4 TSA") and leonardite degrading bacteria ("ALM") for various sampling times from three different leonardite degrading reactor systems. Results are presented as colony-forming units per mL (CFU/mL).

| Sampling date | System 2 | | System 1 | | System 3 | |
| --- | --- | --- | --- | --- | --- | --- |
| | 1/4 TSA | ALM | 1/4 TSA | ALM | 1/4 TSA | ALM |
| April 2019 | 2.2 × 10$^7$ | 6.3 × 10$^7$ | 5.4 × 10$^7$ | 2.6 × 10$^7$ | 4.5 × 10$^7$ | 3.7 × 10$^7$ |
| June 2018 | 1.5 × 10$^7$ | 2.5 × 10$^7$ | 6.0 × 10$^7$ | 1.5 × 10$^7$ | 4.1 × 10$^7$ | 4.7 × 10$^7$ |
| December 2017 | NT | NT | 3.0 × 10$^7$ | 2.6 × 10$^7$ | NT | NT |
| June 2017 | NT | NT | 1.3 × 10$^7$ | 7.9 × 10$^5$ | NT | NT |
| March 2017 | NT | NT | 2.1 × 10$^8$ | 4.0 × 10$^6$ | NT | NT |

NT = Not tested

Table 5 presents selected bacterial isolates identified in various multistage bioreactor systems at various timepoints. Species in bold indicate organisms found at all time points in reactor systems 1, 2, and 3. Reactor systems 1 and 2 included an exogenous microbial stock solution, while reactor system 3 did not. Reactor systems 1 and 3 were pilot-sized systems, with product outputs of approximately 4-8 gallons per day, while reactor system 2 was a commercial scale production system with a product output of approximately 3000 gallons per day. These genera and species were considered consistent microbial community members in the low-rank coal-degrading reactor systems. Bacterial isolates were captured from reactor solutions using two nutrient media types: a general, non-selective medium (¼-TSA and alkaline leonardite selective medium (ALM). All isolates captured were highly abundant in the sample solution at $10^5$ or $10^6$ colony-forming units (CFU)/ml.

TABLE 5

Select bacterial isolates identified in low-rank coal-degrading reactor systems.

| | June 2018 | | | | | | December 2017 | | | | June 2017 | | March 2017 | | |
|---|---|---|---|---|---|---|---|---|---|---|---|---|---|---|---|
| | System 2 (BP) | | System 1 (R4) | | System 3 (R4) | | System 1 (R2) | | System 1 (R4) | | System 1 (R4) | | System 1 (R4) | | Aromatic compound degradation*** |
| | 1/4 TSA | ALM | 1/4 TSA | ALM | 1/4 TSA | ALM | 1/4 TSA | ALM | 1/4 TSA | ALM | 1/4 TSA | ALM | 1/4 TSA | ALM | |
| *Camelimonas lactis* | — | — | — | 1 | 1 | 2 | 2 | 10 | — | 4 | — | 3 | — | — | Possibly |
| *Acinetobacter gyllenbergii* | — | — | 1 | 2 | 1 | 5 | — | — | — | — | — | — | — | — | No |
| *Acinetobacter junii* | — | — | — | — | — | 3 | 1 | 3 | — | — | — | — | — | 1 | Yes |
| *Methylocystis echinoides** | — | — | 1 | 2 | 1 | 2 | — | 5 | — | 9 | — | — | — | — | |
| *Shinella curvata* | — | — | — | — | 1 | 1 | — | 7 | 1 | — | — | — | — | — | No |
| *Shinella fusca* | — | — | — | — | — | — | — | 3 | — | 2 | — | — | — | — | No |
| *Shinella granuli* | 1 | — | — | 4 | — | 3 | 1 | 11 | — | 20 | 1 | 10 | 1 | 2 | No |
| *Shinella yambaruensis* | — | — | — | — | — | 1 | — | — | — | — | — | — | — | — | Yes |
| *Shinella zoogloeoides* | — | — | — | — | — | — | — | 2 | — | 1 | — | — | — | — | Yes |
| *Sphingomonas koreensis* | — | — | 1 | — | 3 | 1 | 2 | 2 | 1 | — | — | — | — | — | Yes |
| *Sphingomonas sanxanigenens* | — | — | — | — | — | — | — | — | — | 1 | — | — | — | — | No |
| *Sphingomonas vermicomposti* | — | 1 | — | — | — | — | — | — | — | — | — | — | — | — | No |
| *Sphingopyxis granuli* | — | — | 1 | — | — | — | — | — | — | — | — | — | — | — | No |
| *Sphingopyxis indica* | — | — | — | — | — | — | — | 1 | — | — | — | — | — | — | Yes |
| *Sphingopyxis italica* | — | — | — | — | — | — | 1 | — | 1 | 4 | — | — | — | — | No |
| *Sphingopyxis solisilvae* | — | — | — | — | 3 | 2 | — | — | — | — | — | — | — | — | No |
| *Sphingopyxis ummariensis* | — | — | — | — | — | 2 | — | — | — | 2 | — | 1 | — | — | Yes |
| *Ferruginibacter alkalilentus*** | 1 | 9 | 2 | 3 | 1 | — | — | — | 1 | — | — | — | — | — | |

*indicates most closely related species in the publicly available, National Center for Biotechnology Information (NCBI) database, yet this species is an obligate methanotroph (i.e. can only grow by consuming methane) and methane generation (i.e. an anaerobic process) is very unlikely in the aerobic leonardite degradation reactor systems.
**indicates isolates have less than 97% identity in DNA sequence of the small ribosomal sub-unit gene (i.e. 16S rRNA gene) with the closest species in the NCBI database, *Ferruginibacter alkalilentus* 93.89% identity, suggesting that these isolates may represent a new bacterial species.
***based on scientific literature Table 6 represents selected bacterial isolates identified in the same bioreactor systems as those of Table 5 and presents data from an additional timepoint relative to Table 4.

TABLE 6

Select bacterial isolates identified in low-rank coal-degrading reactor systems.

| | | April 2019 | | | | | | June 2018 | | |
|---|---|---|---|---|---|---|---|---|---|---|
| | | System 2 | | System 1 | | System 3 | | System 2 | | System 1 |
| Species identity* | TOTAL ISOLATES | 1/4 TSA | ALM | 1/4 TSA | ALM | 1/4 TSA | ALM | 1/4 TSA | ALM | 1/4 TSA |
| *Methylocystis echinoides* | 34 | 1 | — | 5 | 1 | 3 | 4 | — | — | 1 |
| *Microbacterium* spp. (*M. fluvii*, *M. kitamiense*, *M. paraoxydans*, *M. pumilum*, *M. natoriense*, *M. saccharophilum*, and *M. schleiferi*) | 26 | — | — | 1 | — | 2 | 2 | — | — | 6 |
| *Pseudorhodoplanes sinuspersici* | 14 | — | 2 | — | 3 | — | 3 | — | 1 | 1 |

TABLE 6-continued

Select bacterial isolates identified in low-rank coal-degrading reactor systems.

| Species identity | | | | | | | | |
|---|---|---|---|---|---|---|---|---|
| Shinella spp. (S. curvata, S. fusca, S. granuli, S. yambaruensis, and S. zoogloeoides) | 81 | — | — | 6 | 1 | 1 | — | 1 | — | — |
| Sphingomonas spp. (S. aestuarii, S. koreensis, S. sanxanigenens, and S. vermicomposti) | 15 | — | — | 1 | — | — | 2 | — | 1 | 1 |
| Sphingopyxis spp. (S. granuli, S. indica, S. italica, S. solisilvae, and S. ummariensis) | 31 | — | — | 2 | 2 | 3 | 6 | — | — | 1 |

| | | June 2018 | | December 2017 | | June & March 2017 | | |
|---|---|---|---|---|---|---|---|---|
| | System 1 | System 3 | | System 1 | | System 1 | | aromatic |
| Species identity* | ALM | 1/4 TSA | ALM | 1/4 TSA | ALM | 1/4 TSA | ALM | compound degradation** |
| Methylocystis echinoides | 2 | 1 | 2 | — | 14 | — | — | No |
| Microbacterium spp. (M. fluvii, M. kitamiense, M. paraoxydans, M. pumilum, M. natoriense, M. saccharophilum, and M. schleiferi) | 8 | 2 | 2 | — | 1 | 2 | — | Yes |
| Pseudorhodoplanes sinuspersici | 2 | — | 2 | — | — | — | — | No |
| Shinella spp. (S. curvata, S. fusca, S. granuli, S. yambaruensis, and S. zoogloeoides) | 4 | 1 | 5 | 2 | 46 | 2 | 12 | Yes |
| Sphingomonas spp. (S. aestuarii, S. koreensis, S. sanxanigenens, and S. vermicomposti) | — | 3 | 1 | 3 | 3 | — | — | Yes |
| Sphingopyxis spp. (S. granuli, S. indica, S. italica, S. solisilvae, and S. ummariensis) | — | 3 | 4 | 2 | 7 | — | 1 | Yes |

*indicates most closely related genus and species in the publicly available National Center for Biotechnology Information (NCBI) database based on DNA sequencing of the small ribosomal sub-unit gene (i.e. 16S rRNA gene). When multiple species from the same genus were isolated, they were grouped by genus.
**based on scientific literature Bacterial genera consistently found in the low-rank coal-degrading reactor systems, represented in some cases by multiple different species, include: Shinella spp., Sphingomonas spp., Camelimonas spp., Sphingopyxis spp., Acinetobacter spp., Microbacterium spp., Methylocystis spp., and Pseudorhodoplane spp. Each of these genera is characterized by isolates with the capacity for leonardite degradation as evidenced by growth on the ALM media. Thus, the genera listed in Tables 4 and 5 are leonardite degrading bacteria. There are many potential means for leonardite degradation by these microorganisms.

Multiple alkaline treatments have revealed that hydrolysis products of leonardite include fatty acids, peptides, aliphatic, alicyclic and aromatic hydrocarbons, linear carboxylic acids, and alkanols that are cross-linked mainly by ester groups (Grasset and Ambles, "Structure of humin and humic acid from an acid soil as revealed by phase transfer catalyzed hydrolysis," Organic Geochemistry, vol. 29, no. 4, pp. 881-891, 1998).

Alicyclic and aromatic hydrocarbons are the most recalcitrant compounds in humus substances as only a small fraction of microorganisms can metabolize them. Microbial degradation of aromatic compounds relies mainly on bacterial production of mono- and di-oxygenases for use in the catechol pathway. Fewer bacteria have the ability to degrade polycyclic aromatic hydrocarbons (PAHs), and metabolism usually occurs through the conversion to procatechuate and then catechol.

Secretion of alkaline substances for solubilization of low-rank coal have been described in fungi (Hongli, Y. et al. "Production of alkaline materials, surfactants and enzymes by Penicillium decumbens strain P6 in association with lignite degradation/solubilization." Fuel 85.10-11: 1378-

1382, 2006), yet various bacteria can also utilize this mode of action. Biosolubilization of low rank coal by bacterial isolates ranging from *Bacillus mycoides, Microbacterium* sp., *Acinetobacter* sp., and *Enterobacter aerogenes* all showed an increase in pH during degradation (Valero, Nelson, et al. "Production of humic substances through coal-solubilizing bacteria." *Brazilian J Microbiol* 45: 911, 2014). Additionally, hydrolase enzymes involved in the transformation of ester bonds, collectively termed Esterases (EC 3.1.1.x.) can break the ester bonds linking subunits of low-rank coal (Grasset and Ambles 1998). Bacterial species found in the low-rank coal systems like *Microbacterium fluvii, M. pumilum*, and *M. saccharophilum* (Table 5) have various types of esterase activities (Kageyama, Akiko, et al. "*Microbacterium awajiense* sp. nov., *Microbacterium fluvii* sp. nov. and *Microbacterium pygmaeum* sp. nov." *Actinomycetologica* 22: 1, 2008; Kageyama, Akiko, Yoko Takahashi, and Satoshi Ōmura. "*Microbacterium deminutum* sp. nov., *Microbacterium pumilum* sp. nov. and *Microbacterium aoyamense* sp. nov." *IJSEM* 56: 2113, 2006; and Ohta, Yukari, et al. "*Microbacterium saccharophilum* sp. nov., isolated from a sucrose-refining factory." *IJSEM* 63: 2765, 2013). *M. schleiferi* from crude oil contaminated soil has been shown to utilize a toxic component in petroleum, trimethylbenzene, as the sole source of carbon and energy (Lv, Dunyu, and Chu Yu. "Experimental Study on Micro-Biological Degradation of 1, 3, 5-TMB in Groundwater." *J of Clean Energy Technol* 2.2, 2014). The 26 bacterial isolates from the leonardite degradation reactor systems identified as species of *Microbacterium* (Table 6) may use multiple, different modes of action to degrade leonardite.

Certain examples of process systems described herein were abundant in several species of Shinella, which may have the capacity to release ammonia during normal nitrogen metabolism. This release of ammonia, an alkaline substance, may increase the pH of the extracellular solution and act to solubilize low-rank coal. Free-living *S. granuli* and *S. fusca* obtain nitrogen through the dissimilatory nitrate reduction to ammonia (DNRA) pathway while plant-associated species of Shinella can fix nitrogen (I. Vaz-Moreira, C.'et al, "*Shinella fusca* sp. nov., isolated from domestic waste compost," IJSEM, vol. 6-, pp. 144-148, 2010; and A. Poehlein, et al., "Genome sequence of Shinella sp. strain DD 12, isolated from homogenized guts of starved *Daphnia magna*," Stand in Genomic Sci, 11(14), 2016). However, Shinella spp. can also metabolize various nitrogenous aromatic compounds.

*Shinella yambaruensis* SA1, a species also identified in the process systems described herein, is able to use 4-aminobenzensulfonate as a sole carbon, nitrogen, and energy source under aerobic conditions through the ortho cleavage pathway using a deaminating dioxygenase (S. Biala, P. Chadha and H. S. Saini, "Biodegradation of 4-aminobenzenesulfonate by indigenous isolate Shinella yambaruensis SA1 and its validation by genotoxic analysis," *Biotechnol and Bioprocess Engin*, 10:1034, 2014). The nicotine-degradation ability of Shinella sp. strain HZN7 is found on one of five megaplasmids (J. Qiu, Y. et al., "The Complete Genome Sequence of the Nicotine-Degrading Bacterium Shinella sp. HZN7," *Frontiers Microbiol*, 7(1348), 2016) and can oxidize (S)-6-Hydroxynicotine using an oxidase (J. Qiu, et al., "A Novel (S)-6-Hydroxynicotine Oxidase Gene from Shinella sp. Strain HZN7," *Appl Environ Microbiol*, 80:5552, 2014). The role of megaplasmids in other species of Shinella have not been investigated and might play a larger role in organic carbon utilization ability. Pyridine utilization as a sole carbon, nitrogen, and energy source by Shinella zoogloeoides BC-26 occurs at an alkaline pH by production of ammonia (Y. Bai et al., "Aerobic degradation of pyridine by a new bacterial strain, Shinella zoogloeoides BC-26," *J Indust Microbiol & Biotechnol*, 36:1391, 2009). However, this strain exhibited simultaneous nitrification and denitrification in aerobic conditions. Shinella granuli NJUST32 can degrade the nicotine derivative 1H-1,2,4-triazole (TZ), and utilize the products as sole carbon and nitrogen sources (H. Wu, et al., "Biodegradation mechanism of 1H-1,2,4-triazole by a newly isolated strain Shinella sp. NJUST26," *Scientific Reports*, 6, 2016). In the case of both pyridine and TZ, degradation was increased with an additional simple carbon source, suggesting redox cycling enzymes (monooxygenases) proceed through glucose metabolism as heterocyclic compounds are oxidized through electron sinks.

Many types of oxidizers have demonstrated an ability to degrade aromatics in leonardite, such as dehydrogenases/oxidases, peroxidases (e.g., lignin peroxidase, manganese peroxidase), and oxidation of aromatic rings via reactive oxygen species (ROS) release. Structures within low-rank coals can resemble phenols and polyaromatic hydrocarbons (PAHs) (FIG. 3A). Species of the Sphingomonadaceae family are known for their ability to degrade aromatic compounds and spans thirteen genera (Kampfer, P. and S. P. Glaeser, "The Family Sphingomonadaceae." The Prokaryotes. Ed. E. Rosenberg, et al. Springer, Berlin, Heidelberg, 2014). The Sphingopyxis-like species are sphingomonads which are classified into four clusters including four genera—*Sphingomonas, Sphingobium, Novosphingobium*, and *Sphingopyxis*. Large plasmids are involved in the degradation of polycyclic aromatic compounds within this group (Basta, T. et al. "Structural and replicative diversity of large plasmids from sphingomonads that degrade polycyclic aromatic compounds and xenobiotics." *Microbiology* 151: 2025-2037, 2005). *Sphingomonas koreensis* was first identified in 2001 from natural mineral water sources in Korea (Lee, J-S, et al. "*Sphingomonas aquatilis* sp. nov., *Sphingomonas koreensis* sp. nov. and *Sphingomonas taejonensis* sp. nov., yellow-pigmented bacteria isolated from natural mineral water." *International Journal of Systematic and Evolutionary Microbiology* 51: 1491-1498, 2001). One strain, *S. koreensis* ASU-06, isolated in 2014 from Egyptian oily soil was able to degrade four different PAHs, naphthalene, phenanthrene, anthracene, and pyrene (Hesham, Abd El-Latif, et al. "Biodegradation ability and catabolic genes of petroleum-degrading *Sphingomonas koreensis* Strain ASU-06 isolated form Egyptian oily soil." *BioMed Res Int* 2014). The production of biosurfactant(s) increased with the degradation products suggesting biosolubilization may be another mode of action used by *S. koreensis*.

*Camelimonas lactis* was found at multiple time points in the process systems described herein. First isolated from camel milk in a production farm in 2010, *C. lactis* was not tested for esterase activity for characterization (Kämpfer et al., "*Camelimonas lactis* gen. nov., sp. nov., isolated from the milk of camels." *International Journal of Evolutionary Microbiology* 60: 2382-2386, 2010). In 2015, *C. lactis* strain M11 was investigated for the biodegradation of di-n-butyl phthalate (DBP), a monoalkyl phthalate (Chen et al., "Biodegradation of an endocrine-disrupting chemical di-n-butyl phthalate by newly isolated *Camelimonas* sp. and enzymatic properties of its hydrolase." *Biodegradation* 26.2: 171-182, 2015). Phthalate esters are a significant portion of aromatic compounds found associated with humic acids. Interestingly, a hydrolase not specific to DBP was found during stationary growth in broth suspensions of the organism yet, *C. lactis* strain M11 could not grow on plates made with the same compounds.

*Acinetobacter junii* can produce a heteropolysaccharide as an exopolysaccharide (EPS) (Kumar et al., "Structural and immunological studies of an exopolysaccharide from *Acinetobacter junii* BB1A." *Carbohydrate Polymers* 101: 188-195 2014) and recently a low molecular weight rhamnolipid from *A. junii* was shown to emulsify crude oil (Dong et al., "Rhamnolipids Produced by Indigenous *Acinetobacter junii* from Petroleum Reservoir and its Potential in Enhanced Oil Recovery." *Frontiers in Microbiology* 7.1710, 2016). *A. junii* BD produced the maximum amount of this surfactant when 8% soybean oil and 1% sodium nitrate was supplied. *A. junii* can degrade a very wide range of hydrophobic carbon substances and form stable co-aggregates with unrelated genera, forming appendages to oil droplets and production of biosurfactin in the presence of crude oil and alkane biodegradation (Gutnick and Bach, "Potential application of *Acinetobacter* in Biotechnology." Cornelis, Pierre and Ulrike Gerischer. *Acinetobacter: Molecular Biology*. Caister Academic Press, 2008; Malik and Kakii, "Intergeneric coaggregations among *Oligotropha* carboxidovorans and *Acinetobacter* species present in activated sludge." *FEMS Microbiology Letters* 224.1: 23-28, 2003; and Ohadi et al., "Isolation, characterization, and optimization of biosurfactant production by an oil-degrading *Acinetobacter junii* B6 isoalted from an Iranian oil excavation site." *Biocatalysis and Agricultural Biotechnology* 12: 1-9, 2017). *Acinetobacter gyllenbergii* was originally isolated and described from humans (Nemec et al., "*Acinetobacter beijerinckii* sp. nov. and *Acinetobacter gyllenbergii* sp. nov., haemolytic organisms isolated from humans," *International journal of systematic and evolutionary microbiology* 59.1: 118-124, 2009). *A. gyllenbergii* strain 2P01AA was isolated from a NASA assembly facility and is described as an alkaliphile with high resistance to hydrogen peroxide due to extremely potent catalase and hydrolase activity (Derecho et al., "Characterization of Hydrogen Peroxide-Resistant *Acinetobacter* Species Isolated during the Mars Phoenix Spacecraft Assembly." *Astrobiology* 14.10 (2014): 837-847, 2014). *A. gyllenbergii* stain AS89 isolated from palm oil had strong biosurfactant production, which may be important in biosolubiliztion of leonardite in our leonardite degrading reactor systems (Saisa-ard et al., "Isolation and characterization of biosurfactants-producing bacteria isolated from palm oil industry and evaluation for biosurfactants production using low-cost substrates." *BioTechnologia. Journal of Biotechnology Computational Biology and Bionanotechnology* 94.3, 2013).

In the leonardite degradation reactor systems, we would expect to find organisms with unique carbon use capacity since leonardite is so recalcitrant and complex (Grasset & Ambles 1998). The 34 bacterial isolates identified as *Methylocystis echinoides* share 97.95% DNA sequence identity on the small ribosomal sub-unit gene (i.e. 16S rRNA gene). *M. echinoides* is a "Type 2" methanotrophs characterized as an obligate methanotroph (i.e. can only grow by consuming methane) (Bowman, John P., et al. "Revised taxonomy of the methanotrophs: description of *Methylobacter* gen. nov., emendation of *Methylococcus*, validation of *Methylosinus* and *Methylocystis* species, and a proposal that the family Methylococcaceae includes only the group I methanotrophs." *IJSEM* 43: 735, 1993). Methane generation (i.e. an anaerobic process) is very unlikely in the highly aerobic leonardite degradation reactor systems. Based on these physiological requirements, the 34 isolates from the leonardite degrading reactor systems are unlikely to be *Methylocystis echinoides* and would require more physiological and chemotaxonomic characterization to more accurately assign them to a correct or, perhaps new, species. Similarly, the 14 isolates from the leonardite degradation reactor systems identified as Pseudorhodoplanes sinuspersici may represent novel physiology. Pseudorhodoplanes sinuspersici is a newly, described species from oil-contaminated soil initially enriched in n-hexadecane (Tirandaz, Hassan, et al. "*Pseudorhodoplanes sinuspersici* gen. nov., sp. nov., isolated from oil-contaminated soil." *IJSEM* 65: 4743, 2015).

Example 7—Plant Growth Assay

*Arabidopsis thaliana* (genotype Col-0) seedlings were germinated and grown for 7 days on plates in the growth chamber before transplanting into rockwool cubes for plant growth assays. Rockwool is an inert media for growing *Arabidopsis* in a hydroponic like system. The rockwool cubes are fitted into a 6-well tray.

Eight 1 L ½ strength MS media (Murashige & Skoog Basal Medium with Vitamins, M519) solutions were made. The test substance was then added, and the pH of the solution was raised to 5.7.

System product (in this case the output from the fourth reactor in the aerobic digestion process) was evaluated for its ability to improve plant growth relative to a positive biostimulant control (SoilBuilder™). Forty mL of each 1 L treatment solution was dispensed to each rockwool cube. Then, each wetted cube received one *Arabidopsis* seedling. *Arabidopsis* plant grew on an LED light cart for 12 days. Leaf area was determined using the ImageJ software package.

TABLE 7

Treatments for testing plates.

| | | |
|---|---|---|
| 1. | ½MS Media+ | 0.8% Microbial solution (SoilBuilder ™) (v/v) (8 mL/L) |
| 2. | ½MS Media+ | UTC |
| 3. | ½MS Media+ | 0.008% System R4 Working Solution (0.08 mL/L) |
| 4. | ½MS Media+ | 0.04% System R4 Working Solution (0.4 mL/L) |
| 5. | ½MS Media+ | 0.08% System R4 Working Solution (0.8 mL/L) |
| 6. | ½MS Media+ | 0.8% System R4 Working Solution (8 mL/L) |
| 7. | ½MS Media+ | 8.0% System R4 Working Solution (80 mL/L) |

Figure 8:
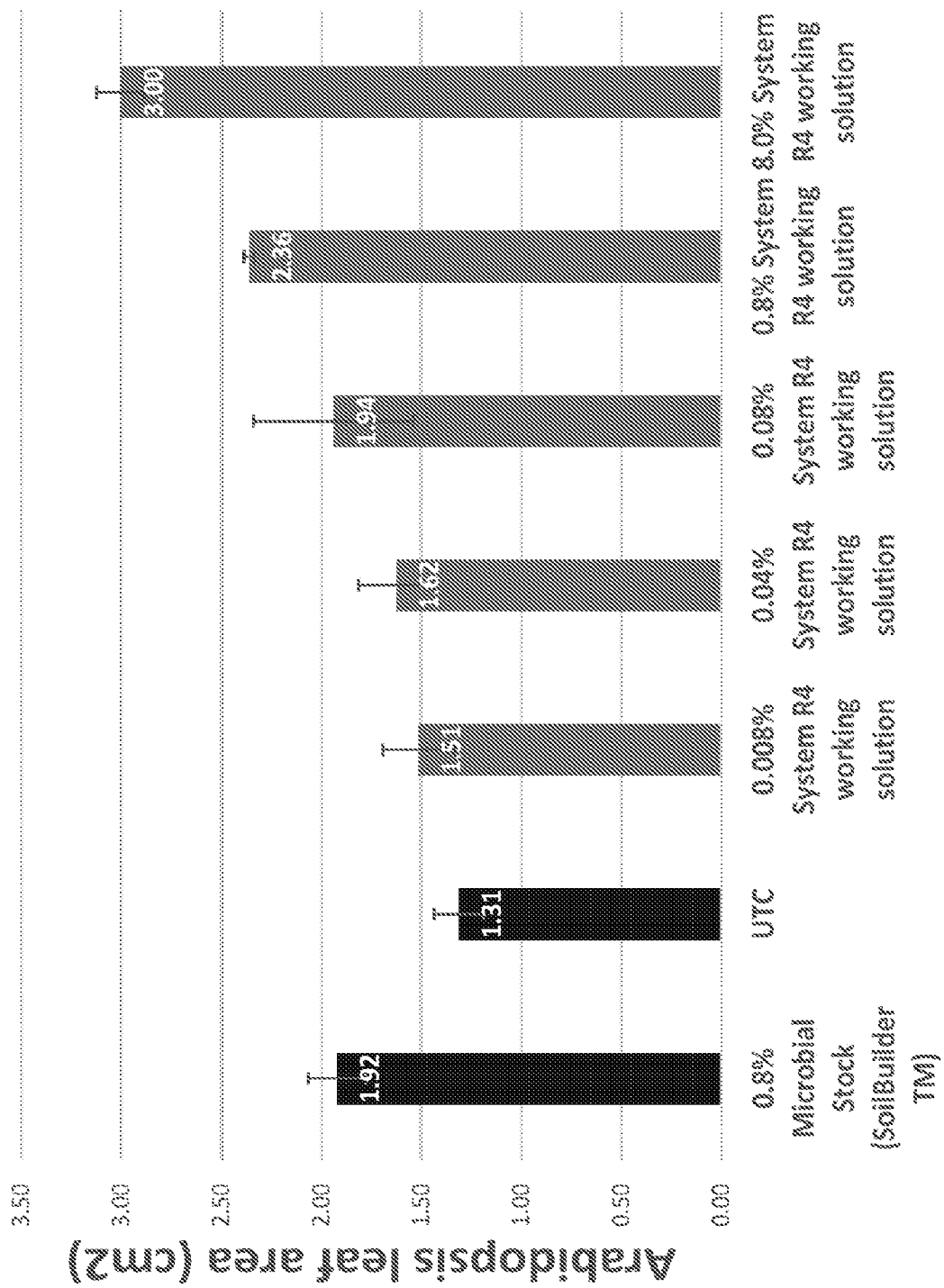
FIG. 8 is a bar graph illustrating the leaf areas of *Arabidopsis thaliana* following treatment with output products from a bioreactor system according to an embodiment of the present disclosure.

The system products (i.e., organic acids generated by the methods and processes described herein) were efficient in promoting plant growth, even at low concentrations (e.g., 0.008%, 0.04%, and 0.08%). Growth is improved relative to the exogenous microbial solution (SoilBuilder™) alone that was used as the microbial inoculant (FIG. 8). SoilBuilder contains microbes which are capable of growing on ALM medium, including Shinella species.

Example 8—Seed Germination Assay

The experiment was set up as a petri dish germination assay. There were 3 replications and each petri dish had 100 hard red spring wheat seeds. Each petri dish treatment had a sterile filter paper wetted with 20 ml of 150 mM NaCl to induce salt stress. Wheat seeds were treated in the following: 1) Water (no salt) 2) Salt, or 3) Salt plus one the following treatments: A Microbial Solution (SoilBuilder™) (at 4 mL, 8 mL, and 12 mL additions) and System Products (at 4 mL, 8 mL, and 12 mL additions).

Treatment 1 was the positive control that did not receive any stress. Treatments 1 and 2 received 20 mL of RO water.

The remaining treatment received 4 mL, 8 mL, and 12 mL of their individual biostimulant products, microbial solution (SoilBuilder™) and System Products, in addition to 150 mM NaCl to a total volume of 20 mL topped up with RO water for each petri dish. Each petri dish received a total of 20 mL of liquids. The experiment lasted 5 days and germination counts were taken on days 3, 4 and 5. The total germination was estimated after day 5. All the data collected were put through JMP for statistical analysis.

As illustrated in FIG. 10, system products (i.e., organic acids generated by the methods and processes described herein) provided significant salt stress alleviation in germinating wheat at the same level as the positive control (no salt stress) and performed better than the microbial stock solution.

Example 9—Wheat Plant Growth Assay

Wheat plant growth tests under salt stress was carried out in greenhouse pots with 3 parts isolite and 1 part profile field and fairway porous ceramic topdressing. 12 replications were made for each treatment. Each pot received 20 seeds. After 1 week of growth, it was thinned down to 12 plants. The plants were separated into 10 groups, each with different treatments:
1. Salt only
2. Microbial Solution (SoilBuilder™) (2 mL/pot)
3. Microbial Solution (SoilBuilder™) (4 mL/pot)
4. Microbial Solution (SoilBuilder™) (8 mL/pot)
5. Aerobic digestion (System) products (2 mL/pot)
6. Aerobic digestion (System) products (4 mL/pot)
7. Aerobic digestion (System) products (8 mL/pot).

Treatment 1 received 100 mL of RO water. Treatments 2-10 received the amount of solution indicated above with additional RO water needed to bring the total solution to 100 mL for each pot. After 12 days of growth, treatments 1-10 were given 100 mL application of 400 mM NaCl to induce salt stress. After another 8 days, treatments 1-10 received 100 mL application of 100 mM NaCl. In the duration of the experiment, each pot was given the same amount of water twice a week. After 28 days of growth, the pots were taken down, and the roots were cleaned off. The shoots and roots were separated and then placed in a drying oven for 3 days. Root and shoot dry weights were recorded. The data was analyzed using the JMP statistical analysis package. System products (i.e., organic acids generated by the methods and processes described herein) demonstrated better wheat plant growth under salt stress than the Microbial Solution (SoilBuilder™) (FIG. 11).

Example 10—Corn Plant Growth Assay

Corn plant growth tests were carried out in greenhouse pots. Plants were germinated and grown in Isolite in 3.5" pots, and thinned to one plant per pot at approximately 3 days after planting. Treatments were made to the planting mix surrounding the plants after thinning Plants were treated water and either one of two system products (System products #1 and System products #2, which are respectively described in Example 6 as Reactor System 1 Product and Reactor System 3 Product) at three different rates (2 ml, 4 ml, or 8 ml per pot). Treatment groups are shown below, with each treatment having 12 replicates. All plants were watered the same (2-3 times a week). Plants were harvested after 4 weeks following treatment, and analyzed for biomass and nutrient content.

Figure 16A:
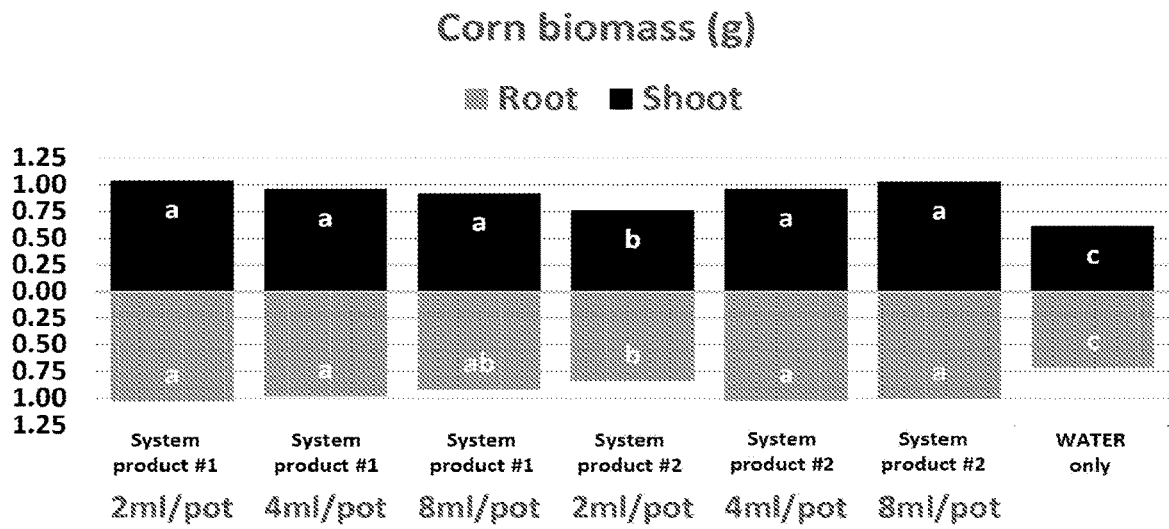
FIG. 16A illustrates increased corn root and shoot biomass from plants treated with two different system products (System Product #1 and System Product #2, which are respectively described in Example 6 as Reactor System 1 Product and Reactor System 3 Product).
Figure 16B:
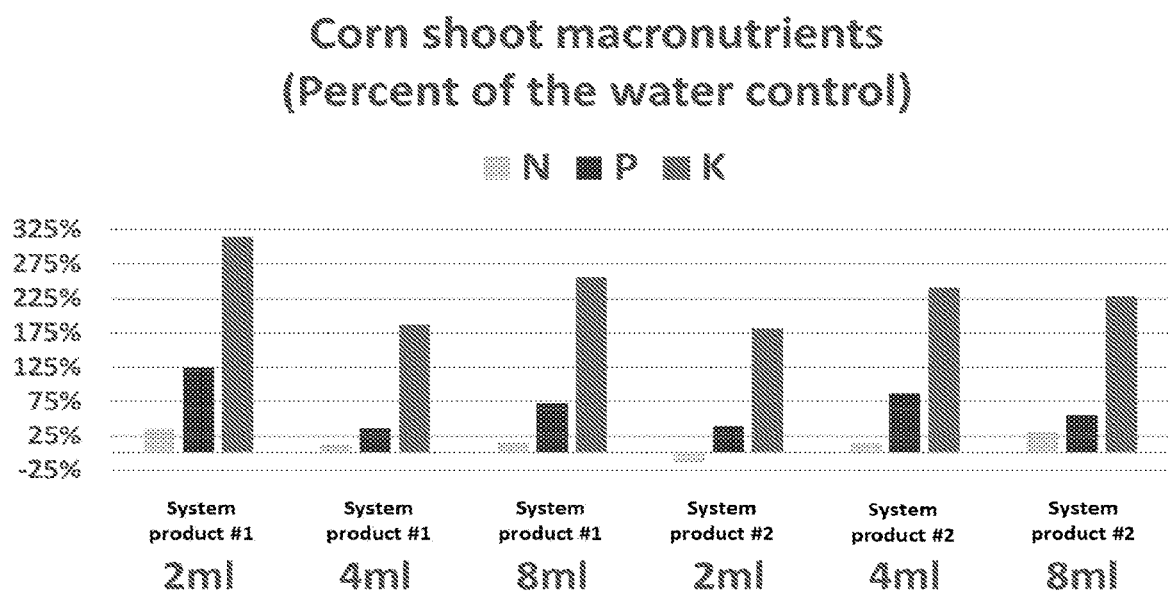
FIG. 16B illustrates increased macronutrients in corn shoots treated with two different system products (System Product #1 and System Product #2, which are respectively described in Example 6 as Reactor System 1 Product and Reactor System 3 Product) relative to water control (data presented as a percent of the water control).

The plants were separated into 7 groups, each with different treatments:
1. System products #1 (2 mL/pot)
2. System products #1 (4 mL/pot)
3. System products #1 (8 mL/pot)
4. System products #2 (2 mL/pot)
5. System products #2 (4 mL/pot)
6. System products #2 (8 mL/pot)
7. Water only As illustrated by FIG. 16A, treatment with system products resulted in increased root and shoot biomass compared to water alone. Corn shoot macronutrient content was also increased by treatment with the system products. As illustrated by FIG. 16B, which provides corn shoot macronutrient content as a percent of the water control, system products increased nitrogen, phosphorus, and potassium concentrations in corn shoots.

Example 11—Cadmium Reduction from Solution by Aerobic Digestion Products

The ability for aerobic digestion products to remove cadmium (Cd) from solution was investigated. To do so, a 2 mM solution of Cd was prepared in RO water from $CdCl_2$ and used to make 1 mM solutions in 20 ml volumes, with 0%, 2%, 4%, or 8% aerobic digestion products included. The mixtures were vortexed vigorously and allowed to settle overnight before centrifugation at 10,000 rpm for 10 min. The clarified supernatants were transferred to new tubes and analyzed for Cd by inductively coupled plasma mass spectrometry (ICP-MS).

Figure 17:
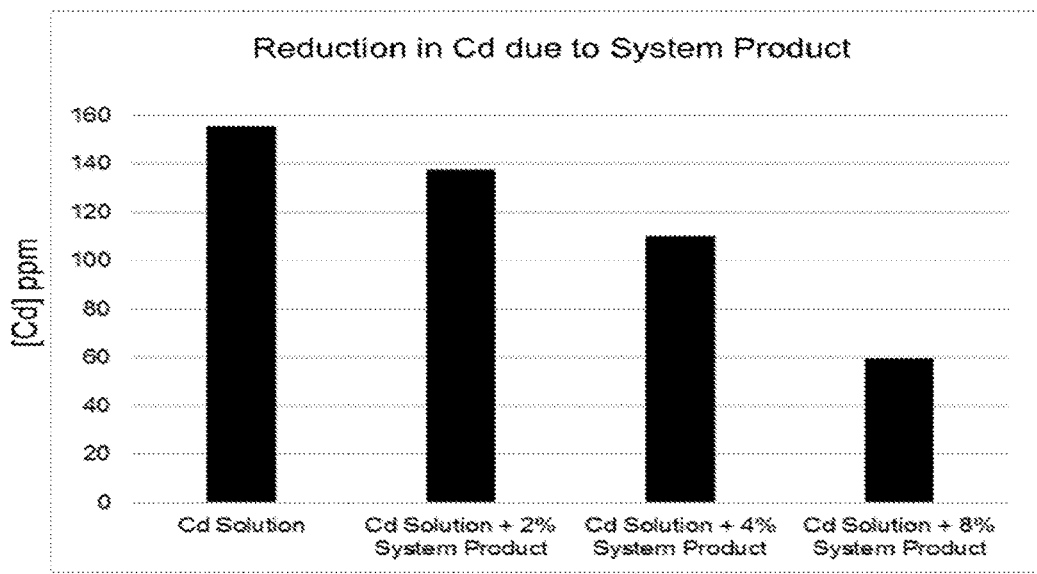
FIG. 17 is a bar graph illustrating the ability of the system products to decrease cadmium (Cd) concentrations in $CdCl_2$ solutions in a dose-dependent manner.

Cd ions were sequestered by the aerobic digestion (system) products in a dose-dependent manner, as demonstrated by FIG. 17.

Example 12—Aerobic Digestion Products Provide Cadmium Toxicity Relief and Improve Germination in Radish The ability for aerobic digestion products to provide relief to plants from cadmium (Cd) toxicity was investigated. A 1 mM Cd solution from $CdCl_2$ was prepared. 1 mM Cd treatment solutions with 0%, 2%, 4%, or 8% aerobic digestion products were prepared. For each treatment and a water control, 30 radish seeds were placed in a Petri dish (3 replicates per treatment) with a Whatman filter paper disk. 10 ml of the treatment solution (or water) were applied to each dish, and the dishes were sealed. The dishes were placed in a light cart with the lights off, and the seeds allowed to germinate over three days. Seedling fresh weigh and appearance were observed.

Figure 18:
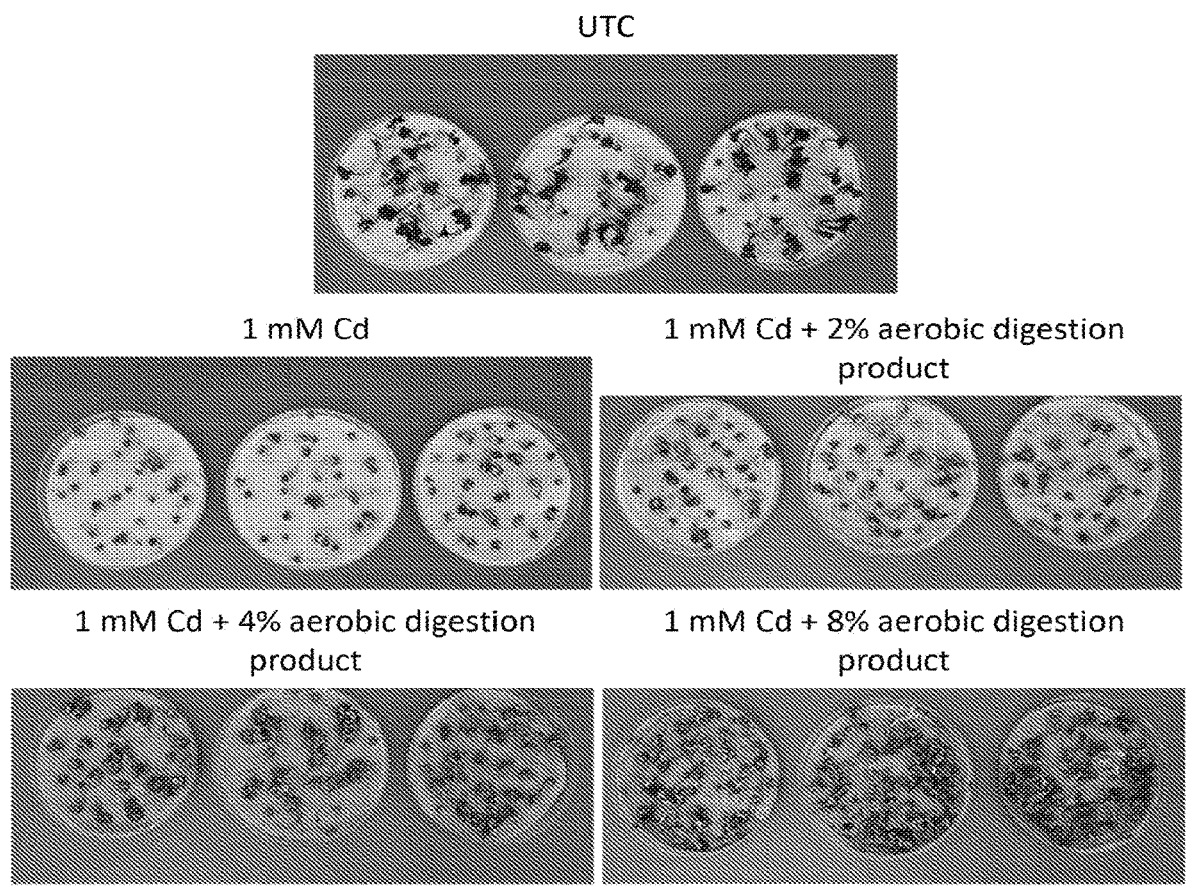
FIG. 18 includes a series of photographs demonstrating noticeable inhibition of radish seedling growth by 1 mM Cd, and a dose-dependent improvement in seedling growth in the presence of 1 mM Cd.
Figure 19:
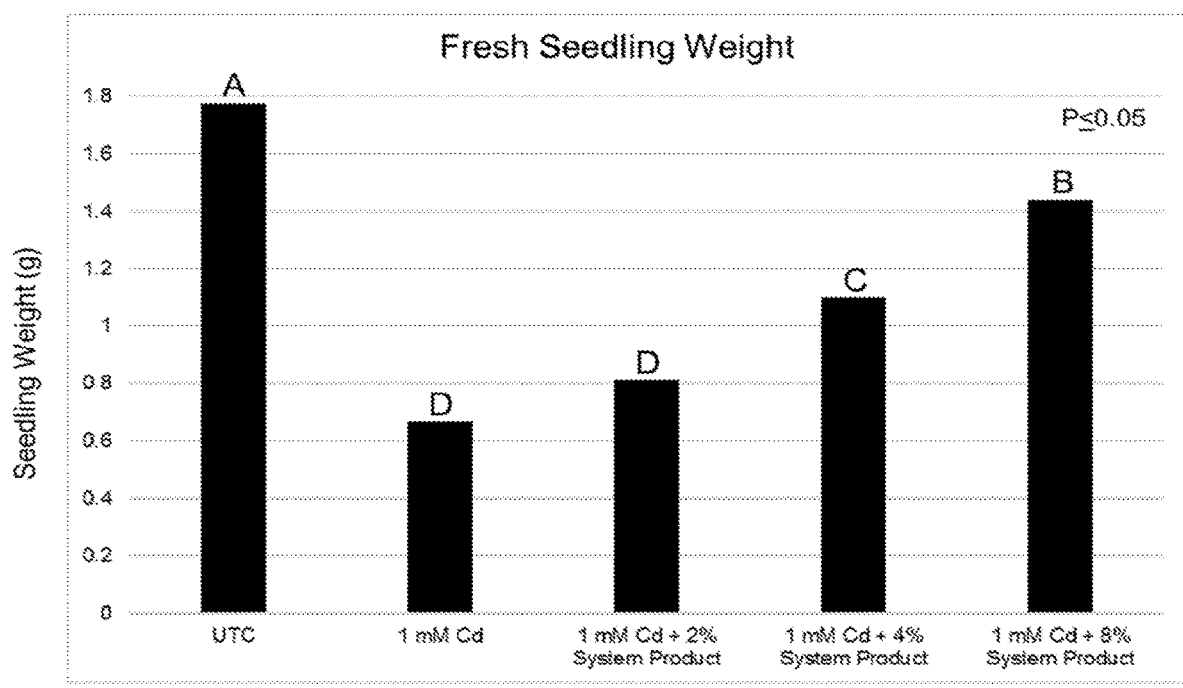
FIG. 19 is a bar graph illustrating the weight of fresh untreated radish seedlings (UTC), and radish seedlings treated with 1 mm Cd, 1 mM Cd and 2% system products, 1 mM Cd and 4% system products, or 1 mM Cd and 8% system products.

1 mm Cd noticeably inhibited seedling growth (see FIG. 18) and coloration. Aerobic digestion products alleviated these toxic effects of Cd (see FIG. 18). Aerobic digestion products also improved seedling fresh weights under Cd stress in a dose-dependent manner (see FIG. 19).

Example 13—Aerobic Digestion Products Provide Copper Toxicity Relief and Improve Wheat Seedling Growth The ability for aerobic digestion products to provide relief to plants from copper (Cu) toxicity was investigated. A 75 ppm Cu solution in half-strength Hoagland solution was prepared. 75 ppm Cu treatment solutions with 0%, 0.5%, 1%, 2%, or 4% aerobic digestion products were prepared. Half-strength Hoagland solution only and half-strength Hoagland solution with 75 ppm Cu were used as controls. Wheat was pre-sprouted in Petri dishes with moistened Whatman filter paper the day before preparing germination pouches. About 30 seeds were placed in each dish, and dishes were sealed before incubating the plates at room temperature (no light necessary). Germination pouches were filled with 30 ml of the treatment solution to be tested. Paper within each pouch was well moistened. 5 wheat seeds, each with an obvious radicle, were placed in each pouch. Three pouches were prepared per treatment. Pouches were placed in a light cart set at 16 hr. light and 8 hr. dark. Over the weekends, pouches were covered with a clear plastic dome, and 300 ml water was poured into the tray holding the pouches to prevent the pouches from drying out. During the week, the pouches were left uncovered. Weight of each pouch was checked daily, and if necessary, RO water was added to keep moisture levels uniform from day to day. Treatment solution was replaced every third day to maintain nutrient and Cu levels. Seedling fresh weight, appearance, and root and shoot length were observed.

Figure 20:
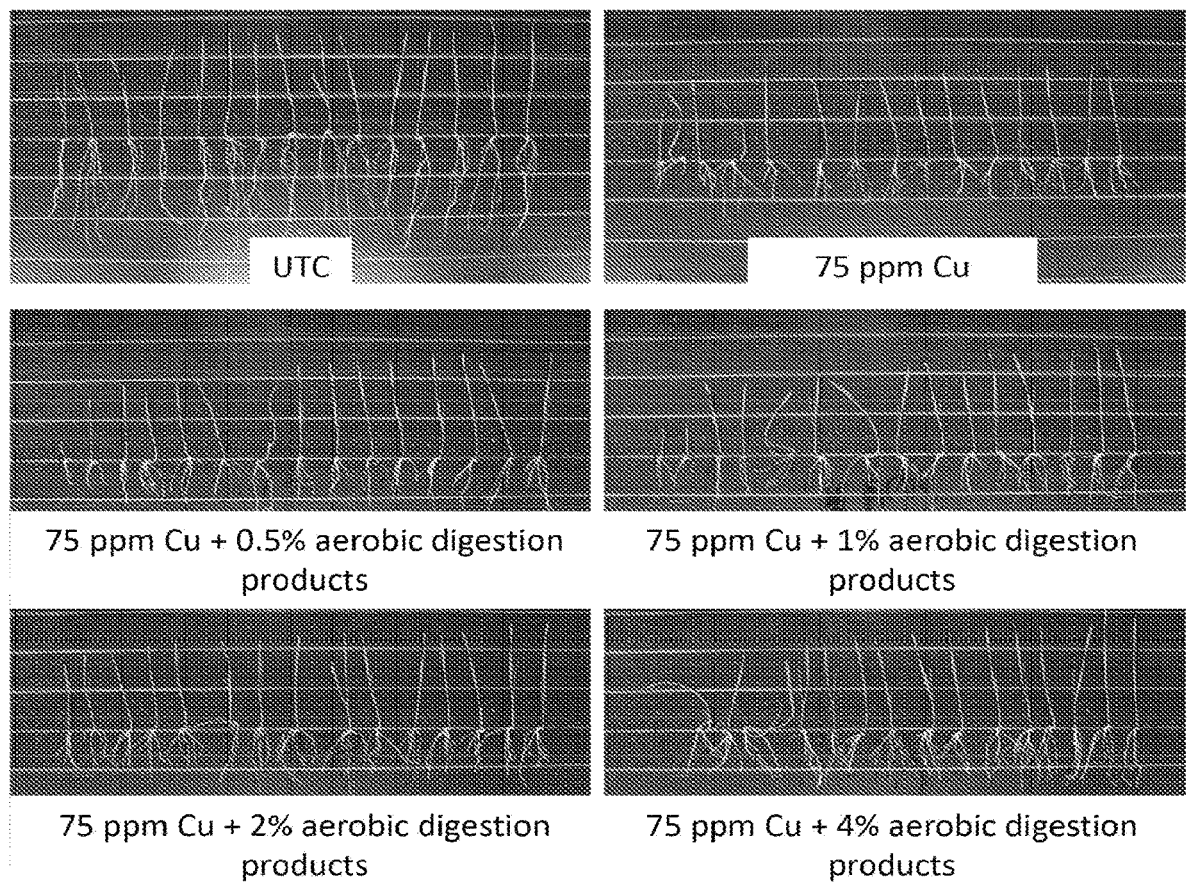
FIG. 20 includes a series of photographs demonstrating noticeable reduction in wheat seedling growth by 75 ppm copper (Cu), and a dose-dependent improvement in seedling growth in the presence of 75 ppm Cu.
Figure 21A:
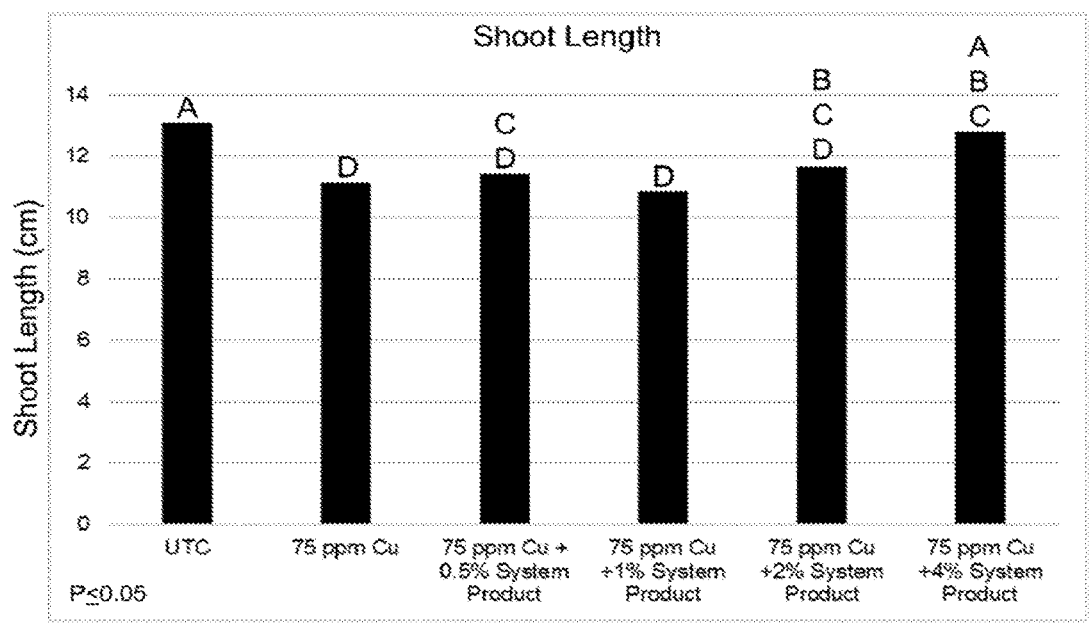
FIGS. 21A and 21B are bar graphs illustrating wheat shoot length (FIG. 21A) or shoot weight (FIG. 21B) of fresh untreated wheat seedlings (UTC), and wheat seedlings treated with 75 ppm Cu, 75 ppm Cu and 0.5% system products, 75 ppm Cu and 1% system products, 75 ppm Cu and 2% system products, or 75 ppm Cu and 4% system products.
Figure 21B:
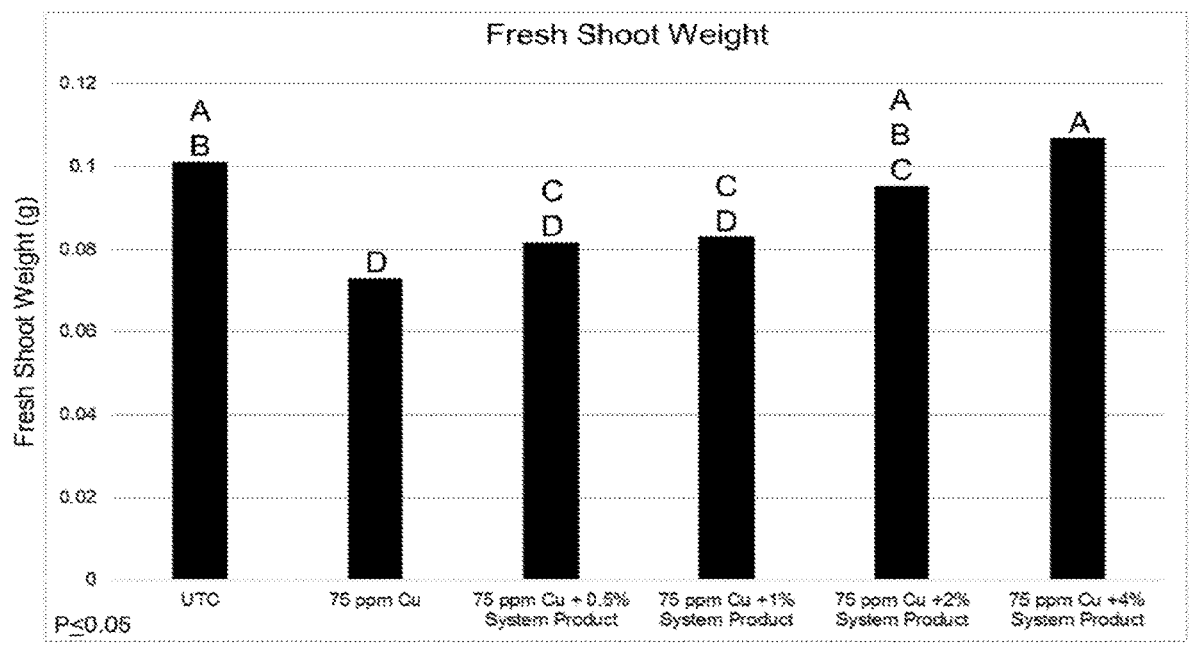
Figure 22A:
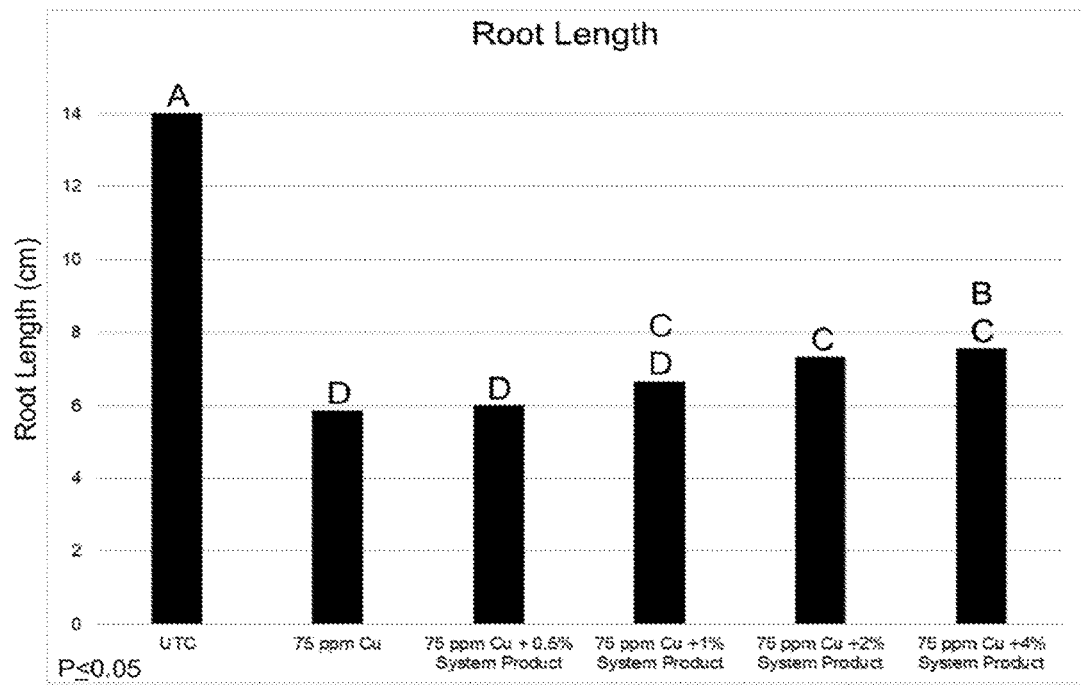
FIGS. 22A and 22B are bar graphs illustrating wheat root length (FIG. 22A) or root weight (FIG. 22B) of fresh untreated wheat seedlings (UTC), and wheat seedlings treated with 75 ppm Cu, 75 ppm Cu and 0.5% system products, 75 ppm Cu and 1% system products, 75 ppm Cu and 2% system products, or 75 ppm Cu and 4% system products.
Figure 22B:
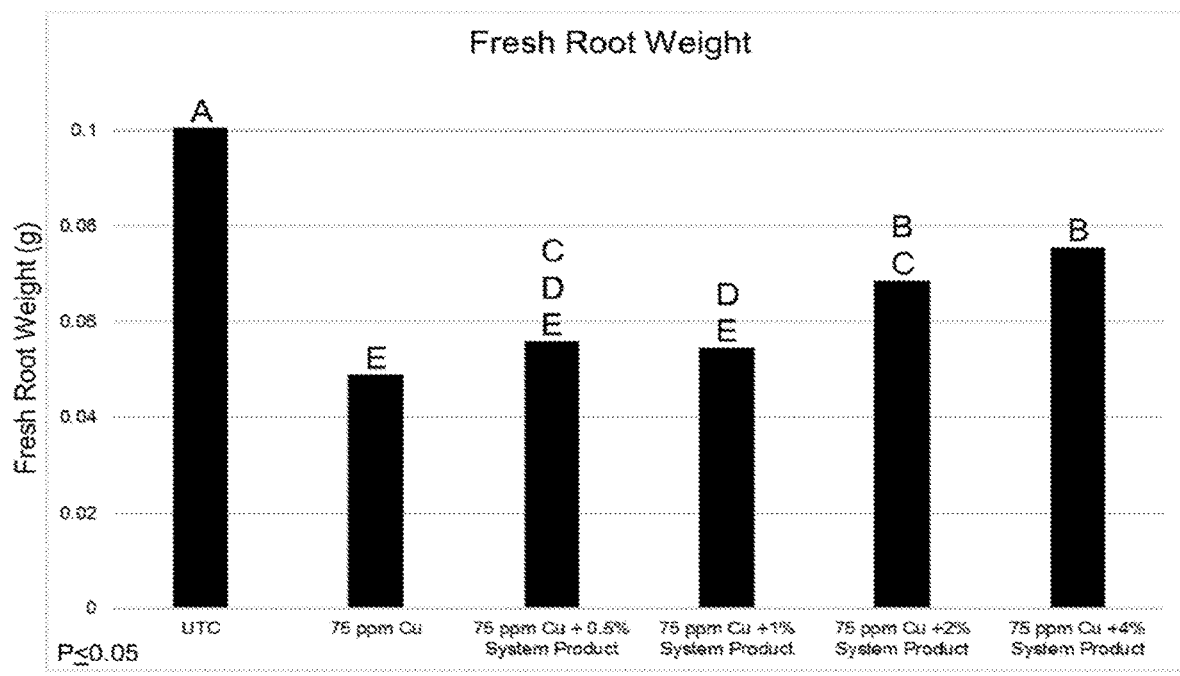

Copper at 75 ppm caused noticeably reduced seedling growth, with roots demonstrating higher sensitivity to the Cu than the shoots (see FIG. 20). Treatment with aerobic digestion products alleviated some of this growth inhibition, particularly at the higher doses (see FIG. 20). Cu at 75 ppm significantly reduced shoot length. Aerobic digestion products at 4% reversed this growth inhibition (see FIG. 21A). Aerobic digestion products at these concentrations also reversed shoot biomass reduction caused by 75 ppm CU (see FIG. 21B). Roots were much more sensitive than shoots to 75 ppm Cu. Aerobic digestion products at 2% and 4% significantly alleviated the Cu-induced growth inhibition, although root growth was not restored to the length of untreated controls (see FIGS. 22A and 22B). Roots treated with the aerobic digestion products also appeared bushier than the Cu-only control. Total seedling weights closely reflected the root weights. Copper at 75 ppm greatly reduced total seedling weights. Treatment with the aerobic digestion products at 2% and 4% minimized the copper toxicity, resulting in greater total seedling biomass relative to the Cu-only control.

Example 14—Aerobic Digestion Products Increase Soil Respiration

The effect of the aerobic digestion products on soil respiration were investigated.

Figure 24:
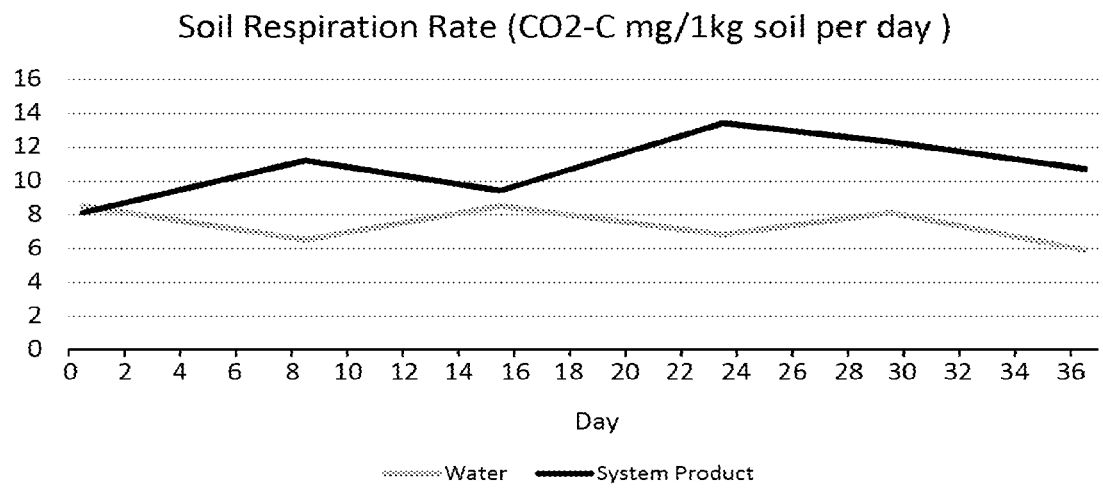
FIG. 24 is a line graph depicting soil respiration rates over 36 days, according to one embodiment.

An initial experiment examined the effect of the aerobic digestion products on microbial respiration. Large containers (soil buckets), each with a different treatment, were set up and left for one month. Soil buckets were prepared using 12 kg of a sand loam agricultural soil. Each bucket was treated with 500 ml of the treatment solution and 500 ml of water. Samples were taken weekly, and microbial respiration was measured using the Solvita $CO_2$-Burst test, which measures the $CO_2$ evolved in a give volume of soil over 24 hours. Soil buckets were treated with either water only, or a diluted (16%) solution of system product (aerobic digestion products). The system products improved soil respiration over a 6-week time period relative to water (see FIG. 24).

A second experiment was designed to determine the effect of system products compared to a commercial humic acid product, in conjunction with 10-34-0 starter fertilizer and a Zn fertilizer (ACA PLUS) containing 8.5% Zn in the form of zinc oxide, and 7% ammonical nitrogen. The commercial humic acid product was diluted to achieve the same concentration of total humic acids as found in the system products (aerobic digestion products) for each treatment.

Three corn plants were planted per pot in a 4:1 mix of Isolite Porous Ceramic and Profile Greens Grade. There were 11 replicate pots per treatment. After 2-3 days of germination, plants were thinned to 1 plant per pot. All pots received 10-34-0 fertilizer (10% ammoniacal nitrogen and 34% P205 at the time of treatment. All pots received at one week after treatments UAN32 50 lb N/A. Additional treatments looked at the effect of 3 rates of ACA PLUS application: 1 qt/A, 2 qt/A, and 4 qt/A. After treatment, plants were randomized on the greenhouse for a randomized complete block design. Plants were watered with RO water twice per week. The experiment ran for 4 weeks. Basal soil respiration was taken for each replicate for each treatment using the Solvita system.

Figure 25:
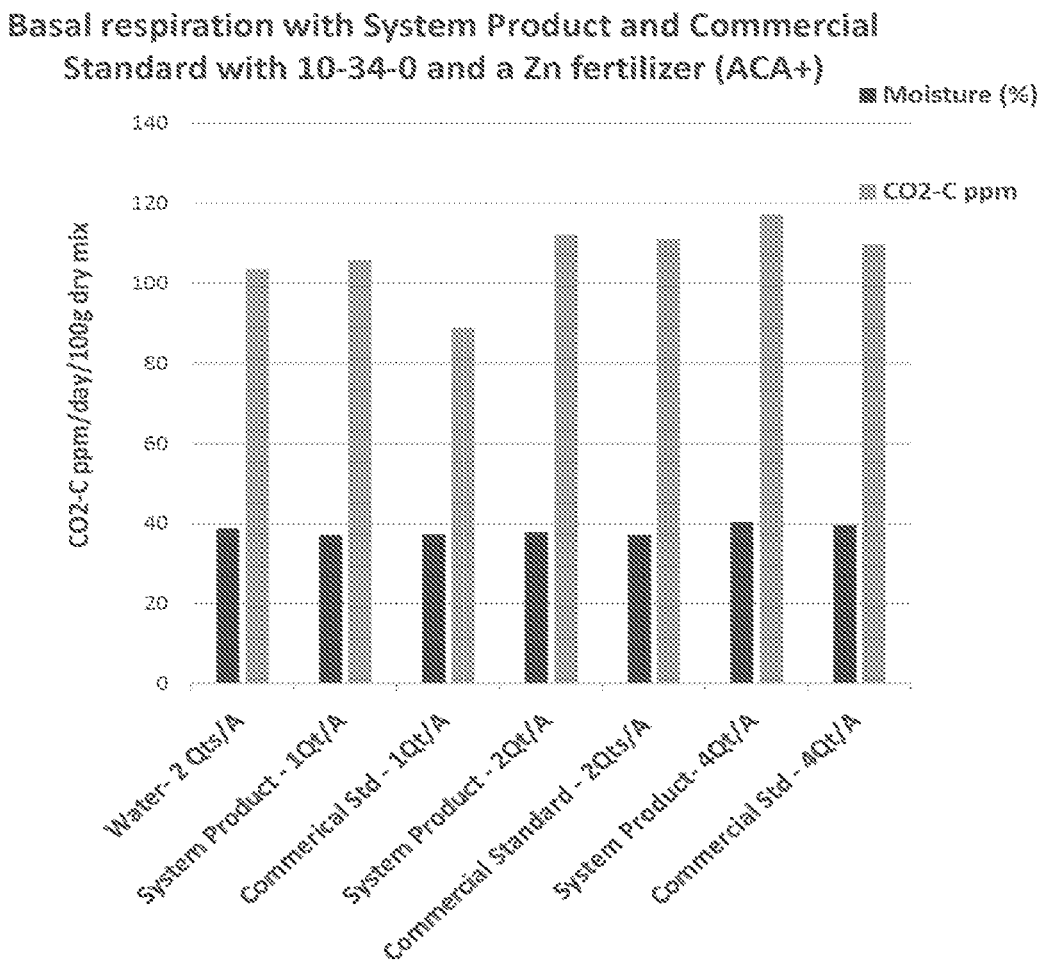
FIG. 25 is a bar graph illustrating basal soil respiration rates with system products and commercial standard (i.e., commercial humic acid product) with 10-34-0 and a Zn fertilizer (ACA PLUS).

At the same level of humic acids provided, the system products improved soil respiration relative to the commercial humic acid product at all ACA Plus application rates (see. FIG. 25).

Example 15—Use of Peat as the Low-Rank Coal

Peat can be used as a feedstock to generate aerobic digestion products in accordance with the methods and procedures described herein. Peat contains a high organic matter content, with both humic and fulvic acids, as well as leonardite-degrading organisms.

Lambert Peat was found to contain $6.53 \times 10^5$ cfu/g of diverse leonardite degraders based on microbial growth on ALM plates. A system to enrich for leonardite degraders from a peat feedstock was generated. In this system, a 50/50 (weight/volume) mixture of Lambert Peat and System Product were incubated together for 48 hours, and then dewatered using a French press. The collected aqueous solution contained $7 \times 10^7$ cfu/mL leonardite degrading organisms based on microbial growth on ALM plates. This number of organisms constitutes a two-fold increase from what would have been expected from just the combination of Lambert Peat and System Product based on the original leonardite degrading community counts from these two feedstocks. This demonstrates that leonardite degraders were further enriched by incubation with peat and system product.

Example 16—Using E4/E6 Ratio to Monitor Leonardite Degradation

Solutions produced by the methods and processes described herein were subjected to determination of the E4/E6 ratio to demonstrate the degradation of leonardite and mostly high molecular weight organic acids (i.e. humic acids) to a greater concentration of lower molecular weight organic acids (i.e. fulvic acids) as a result of the methods and processes described in the present application.

The E4/E6 ratio is a measure of relative levels of aromaticity of a solution. Specifically, E4 is the absorbance of a solution measured on a spectrophotometer at 465 nm. E6 is the absorbance measured at 665 nm. The ratio of E4 to E6 is a standard metric for monitoring the change of aromaticity of a solution with humic acids.

TABLE 8

E4/E6 changes from working solution from reactor 1 and system product (output from reactor 4) for one embodiment of the methods and processes described herein. In addition measurements of the chelation efficiency are included (see Example 2 for discussion on chelation efficiency and chelation capacity).

| Solution measured | E4/E6 ratio* |
| --- | --- |
| Reactor 1 | 2.197 |
| System product | 4.988 |

*ratio is the average of eight replicates.

The decreasing aromaticity from working solution from system reactor 1 to system product (Table 8) correlates to decreasing molecular weight of organic acid groups and demonstrates the breakdown of humic acids (i.e. high molecular weight organic acids) to fulvic acids (i.e. lower molecular weight organic acids) due to the actions of the leonardite degrading microorganisms in this system.

E4/E6 has also been used to monitor and compare shake flask solutions with variations in the addition of microbial stock solution or type of phosphorus source.

TABLE 9

Summary of results from a shake flask experiment meant to simulate the conditions for methods and processes for producing aerobic digestion products from a low-rank coal substrate in the reactor system. Specifically, alkaline-treated leonardite, rock phosphate, yeast and water were added to the shake flasks. The test variable in this experiment was adding the microbial stock solution or not adding the microbial stock solution as a source of exogenous leonardite degrading bacteria.

| Treatments | Leonardite degrading bacteria (CFU/mL) | | pH | | E4/E6 ratio | |
| --- | --- | --- | --- | --- | --- | --- |
| | Day 0 | Day 8 | Day 0 | Day 14 | Day 0 | Day 14 |
| With microbial stock solution | $4.75 \times 10^4$ | $1.52 \times 10^8$ | 7.3 | 7.2 | 3.48 | 6.00 |
| Without microbial stock solution | $2.23 \times 10^3$ | $\geq 1.00 \times 10^6$ | 7.6 | 8.3 | 4.26 | 6.87 |

What is claimed is:

1. A method of digesting a low-rank coal substrate in a multistage bioreactor system, the method comprising
   (a) combining a low-rank coal substrate, water, and rock phosphate to form an aqueous mixture;
   (b) digesting the low-rank coal substrate by incubating the aqueous mixture in a first bioreactor;
   (c) transferring at least a portion of the aqueous mixture from the first bioreactor to a second bioreactor;
   (d) further digesting the low-rank coal substrate by incubating the aqueous mixture in the second bioreactor, wherein the digesting of (b) and (d) produces digestion products of the low-rank coal substrate and the incubating of (b) and (d) produces a consortium of microbes capable of digesting low-rank coal; and
   (e) collecting the digestion products of (b) or (d), wherein the digestion products of (b) or (d) comprise humic acids and fulvic acids; and
   wherein the first bioreactor and second bioreactor are part of the multistage bioreactor system comprising two or more interconnected bioreactors.

2. The method of claim 1, wherein the aqueous mixture further comprises yeast.

3. The method of claim 1, wherein the consortium of microbes comprises microbes present in the low-rank coal substrate at the time of the combining.

4. The method of claim 1, wherein the consortium of microbes comprise microbes present in the rock phosphate at the time of the combining.

5. The method of claim 1, wherein the consortium of microbes comprises species from one or more of the following genera: *Shinella*, *Sphingomonas*, *Camelimonas*, *Sphingopyxis*, *Acinetobacter*, *Microbacterium*, *Methylocystis*, or *Pseudorhodoplanes*.

6. The method of claim 1, wherein the digestion products of the low-rank coal substrate are produced by microbes present in the low-rank coal substrate at the time of the combining.

7. The method of claim 1, wherein the low-rank coal substrate comprises leonardite.

8. The method of claim 7, further comprising pretreating the leonardite with an alkaline solution before the combining.

9. The method of claim 1, wherein the first bioreactor and the second bioreactor are fluidized bed bioreactors.

10. The method of claim 9, wherein the fluidized bed bioreactors comprise pumps or stirrers that circulate particles of the low-rank coal substrate and the rock phosphate within the first bioreactor and the second bioreactor.

11. The method of claim 1, wherein the aqueous mixture is maintained under aerobic conditions during the incubating of (b) and (d).

12. The method of claim 1, wherein the first bioreactor and the second bioreactor are connected by a transfer line.

13. The method of claim 1, wherein the transferring is performed continuously.

14. The method of claim 13, wherein volumes of liquid within the first bioreactor and the second bioreactor, respectively, are maintained constant.

15. The method of claim 14, further comprising continuously transferring the aqueous mixture from the second bioreactor to a third bioreactor.

16. The method of claim 15, further comprising continuously transferring the aqueous mixture from the third bioreactor to a fourth bioreactor.

17. The method of claim 1, further comprising recovering the digestion products by separating a supernatant phase from a floc phase, wherein the supernatant phase comprises aerobic digestion products and the floc phase comprises solids and dense humic substances.

18. The method of claim 17, wherein the separating comprises separation by gravity in a settling tank, or by centrifugation.

19. The method of claim 1, wherein the digestion products comprise organic acids, low-rank coal derivatives, primary and secondary microbial metabolites, or a combination thereof.

20. The method of claim 1, wherein the incubating of (b) is continued until a preselected E4/E6 ratio is attained, a preselected zeta potential is attained, a preselected chelation capacity is attained, or a combination thereof.

21. The method of claim 1, wherein the low-rank coal substrate has a particle size of 0.001 mm to 0.1 mm.

22. The method of claim 1, wherein additional yeast is incorporated into the aqueous mixture at least once during the incubating of (b).

23. The method of claim 1, further comprising incorporating an exogenous microbial stock solution into the aqueous mixture.

24. The method of claim 1, wherein the digestion products comprise between about 0.5-30% humic acids.

25. The method of claim 8, wherein the alkaline solution has a concentration of potassium hydroxide of 0.05M or less.

26. The method of claim 1, wherein the digestion products comprise fatty acid esters, alcohols, phenols, amines, long-chain alkanes and alkenes, or phthalates.

\* \* \* \* \*